US012606611B2

(12) United States Patent
Hunsperger et al.

(10) Patent No.: US 12,606,611 B2
(45) Date of Patent: Apr. 21, 2026

(54) ANTIBODIES WHICH SPECIFICALLY BIND TO DENGUE VIRUS SEROTYPE 4 (DENV4) NON-STRUCTURAL PROTEIN 1 (NS1) AND METHODS OF USE THEREOF TO DETECT A DENV4 INFECTION

(71) Applicant: The United States of America, as represented by the Secretary, Department of Health & Human Services, Rockville, MD (US)

(72) Inventors: Elizabeth Anne Hunsperger, Fort Collins, CO (US); Tesfaye Gelanew Taye, San Juan, PR (US)

(73) Assignee: The United States of America, as represented by the Secretary, Department of Health & Human Services, Bethesda, MD (US)

( * ) Notice: Subject to any disclaimer, the term of this patent is extended or adjusted under 35 U.S.C. 154(b) by 967 days.

(21) Appl. No.: 17/583,936

(22) Filed: Jan. 25, 2022

(65) Prior Publication Data

US 2022/0144921 A1 May 12, 2022

Related U.S. Application Data

(63) Continuation-in-part of application No. 16/310,964, filed as application No. PCT/US2017/038703 on Jun. 22, 2017, now Pat. No. 11,407,818.

(60) Provisional application No. 62/353,690, filed on Jun. 23, 2016.

(51) Int. Cl.
| | |
|---|---|
| *C07K 16/10* | (2006.01) |
| *G01N 33/569* | (2006.01) |

(52) U.S. Cl.
CPC .......... *C07K 16/1081* (2013.01); *C07K 16/10* (2013.01); *G01N 33/56983* (2013.01); *G01N 2333/185* (2013.01); *G01N 2800/26* (2013.01)

(58) Field of Classification Search
CPC ................ C07K 16/1081; C07K 16/10; G01N 33/56983; G01N 2333/185; G01N 2800/26; G01N 2469/10
See application file for complete search history.

(56) References Cited

FOREIGN PATENT DOCUMENTS

WO      2015/196192      12/2015

OTHER PUBLICATIONS

Paul, WE (1993) Fundamental Immunology, 3rd ed. Raven Press, NY, Chap. 9, pp. 292-295.*

Rudikoff, S et al. (1982) Proc. Natl. Acad. Sci. USA, 79:1979-1983 (doi: 10.1073/pnas.79.6.1979).*
Colman, PM (1994) Research in Immunology, Elsevier, NY, 145(1):33-36.*
Bendig. M. M. (1995) Methods: A Companion to Methods in Enzymology, 8:83-93.*
MacCallum et al. (Oct. 11, 1996) J. Mol. Biol., 262(5):732-745. (doi: 10.1006/jmbi.1996.0548).*
Casset et al (2003) Biochemical and Biophysical Research Communications, 307:198-205. (doi:10.1016/S0006-291X(03)01131-8).*
Chen et al. (1995) EMBO J., 14(12):2784-2794. (doi: 10.1002/j.1460-2075.1995.tb07278.x).*
Kebaneilwe Lebani: "Antibody Discovery for Development of a Serotyping Dengue Virus NS1 Capture Assay",9,Jan. 1, 2014(Jan. 1, 2014), pp. 1-201, XP055405444 Retrieved from the Internet: URL:https://espace.library.uq.sdu.au/data/.
Christopher Bruce Howard: "Identification of Epitopes on the Dengue Virus Type 4 Envelope Glycoprotein Involved in Neutralisation by Antibodies A thesis submitted in 2006 for a Doctor of Philosophy degree" Jan. 1, 2006 Jan. 1, 2006), XP055190400, Retrieved from the Internet: URL:http://eprints.qut.edu.au/16401/1/Christopher Howard fhesis.pdf.
Chunya Puttikhunt et al: The development of a novel serotyping-NS1-ELISA to identify serotypes of dengue virus, Journal of Clinical Virology, Elsevier, Amsterdam, NL, vol. 50, No. 4,Jan. 3, 2011 Jan. 3, 2011), pp. 314-319, XP028163154.
Diego Allonso et al: "Polyclonal antibodies against properly folded Dengue virus NS1 protein expressed nenable sensitive and early dengue diagnosis", Journal of Virological Methods, Elsevier BV, NL, vol. 175, No. 1, Apr. 27, 2011 (Apr. 27, 2011), pp. 109-116, XP028226728.
Inbal Sela-Culang et al: "The Structural Basis of Antibody-Antigen Recognition", Frontiers in Immunology, vol. 4, Jan. 1, 2013 (Jan. 1, 2013), XP055168305.
Kathryn Rozen-Gagnon et al: "Expression and immunoaffinity purification of recombinant dengue virus 2 NS1 protein as a cleavable SUMOstar fusion", Protein Expression and Purification, vol. 82, No. Nov. 11, 2011 (Nov. 11, 2011), pp. 20-25, XP028457966.
International Search Report issued in PCT/US2017/038703, dated Nov. 14, 2017.
Rudikoff, S et al. (1982) Proc. Natl. Acad. Sci. USA, 79:1979-1983.
Gelanew et al., "Development and characterization of serotype-specific monoclonal antibodies against the dengue virus-4 (DENV-4) non-structural protein (NS1)", Virology Journal (2018) 15:30, 12 pages.

* cited by examiner

*Primary Examiner* — Robert S Landsman
(74) *Attorney, Agent, or Firm* — Polsinelli PC

(57) ABSTRACT

The present disclosure relates to polypeptides that specifically bind to Dengue virus non-structural protein 1, including antibodies and fragments thereof. The antibody or antigen-binding fragment thereof may specifically bind Dengue virus (DENV) serotype 4 and include: a heavy chain variable region that comprises at least one CDR amino acid sequence selected from the group consisting of: SGYNWH, YIHYSGGTNYNPSLKS, RTGTVPFAY, SYVMH, YLNPYNDDTKYNEKFKG, and GPPYALDY. The present disclosure further relates to methods of producing the polypeptides of the present disclosure, methods of diagnosing DENV, and methods of treating a DENV infection.

16 Claims, 13 Drawing Sheets

Specification includes a Sequence Listing.

FIG. 2A                                                    FIG. 2B

SEQUENCE LISTING

```
<160> NUMBER OF SEQ ID NOS: 44

<210> SEQ ID NO 1
<211> LENGTH: 6
<212> TYPE: PRT
<213> ORGANISM: Mus musculus

<400> SEQUENCE: 1

Ser Gly Tyr Asn Trp His
1               5

<210> SEQ ID NO 2
<211> LENGTH: 16
<212> TYPE: PRT
<213> ORGANISM: Mus musculus

<400> SEQUENCE: 2

Tyr Ile His Tyr Ser Gly Gly Thr Asn Tyr Asn Pro Ser Leu Lys Ser
1               5                   10                  15

<210> SEQ ID NO 3
<211> LENGTH: 9
```

-continued

```
<212> TYPE: PRT
<213> ORGANISM: Mus musculus

<400> SEQUENCE: 3

Arg Thr Gly Thr Val Pro Phe Ala Tyr
1               5

<210> SEQ ID NO 4
<211> LENGTH: 5
<212> TYPE: PRT
<213> ORGANISM: Mus musculus

<400> SEQUENCE: 4

Ser Tyr Val Met His
1               5

<210> SEQ ID NO 5
<211> LENGTH: 17
<212> TYPE: PRT
<213> ORGANISM: Mus musculus

<400> SEQUENCE: 5

Tyr Leu Asn Pro Tyr Asn Asp Asp Thr Lys Tyr Asn Glu Lys Phe Lys
1               5                   10                  15

Gly

<210> SEQ ID NO 6
<211> LENGTH: 8
<212> TYPE: PRT
<213> ORGANISM: Mus musculus

<400> SEQUENCE: 6

Gly Pro Pro Tyr Ala Leu Asp Tyr
1               5

<210> SEQ ID NO 7
<211> LENGTH: 12
<212> TYPE: PRT
<213> ORGANISM: Mus musculus

<400> SEQUENCE: 7

Ser Val Ser Ser Ser Ile Ser Ser Ser Asn Leu His
1               5                   10

<210> SEQ ID NO 8
<211> LENGTH: 7
<212> TYPE: PRT
<213> ORGANISM: Mus musculus

<400> SEQUENCE: 8

Gly Thr Ser Asn Leu Ala Ser
1               5

<210> SEQ ID NO 9
<211> LENGTH: 9
<212> TYPE: PRT
<213> ORGANISM: Mus musculus

<400> SEQUENCE: 9

Gln Gln Trp Ser Ser Tyr Pro Leu Thr
1               5

<210> SEQ ID NO 10
<211> LENGTH: 11
```

-continued

```
<212> TYPE: PRT
<213> ORGANISM: Mus musculus

<400> SEQUENCE: 10

Arg Ala Ser Gln Asp Ile Ser Asn Tyr Leu Asn
1               5                   10

<210> SEQ ID NO 11
<211> LENGTH: 7
<212> TYPE: PRT
<213> ORGANISM: Mus musculus

<400> SEQUENCE: 11

Tyr Thr Ser Arg Leu His Ser
1               5

<210> SEQ ID NO 12
<211> LENGTH: 9
<212> TYPE: PRT
<213> ORGANISM: Mus musculus

<400> SEQUENCE: 12

Gln Gln Gly Asn Thr Leu Pro Arg Thr
1               5

<210> SEQ ID NO 13
<211> LENGTH: 118
<212> TYPE: PRT
<213> ORGANISM: Mus musculus

<400> SEQUENCE: 13

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Asn Trp His Trp Ile Arg Gln Phe Pro Gly Asn Lys Leu Glu Trp
        35                  40                  45

Met Gly Tyr Ile His Tyr Ser Gly Gly Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Arg Thr Gly Thr Val Pro Phe Ala Tyr Trp Gly Gln Gly Thr
            100                 105                 110

Leu Val Thr Val Ser Ala
        115

<210> SEQ ID NO 14
<211> LENGTH: 117
<212> TYPE: PRT
<213> ORGANISM: Mus musculus

<400> SEQUENCE: 14

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45
```

-continued

```
Gly Tyr Leu Asn Pro Tyr Asn Asp Asp Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Tyr Gly Pro Pro Tyr Ala Leu Asp Tyr Trp Gly Gln Gly Thr Ser
            100                 105                 110

Val Thr Val Ser Ser
        115
```

```
<210> SEQ ID NO 15
<211> LENGTH: 108
<212> TYPE: PRT
<213> ORGANISM: Mus musculus

<400> SEQUENCE: 15
```

```
Glu Ile Val Leu Thr Gln Ser Pro Ala Leu Met Ala Ala Ser Pro Gly
1               5                   10                  15

Glu Lys Val Thr Ile Thr Cys Ser Val Ser Ser Ser Ile Ser Ser Ser
                20                  25                  30

Asn Leu His Trp Tyr Gln Gln Lys Ser Glu Thr Ser Pro Lys Pro Trp
            35                  40                  45

Ile Tyr Gly Thr Ser Asn Leu Ala Ser Gly Val Pro Val Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Ser Tyr Pro
                85                  90                  95

Leu Thr Phe Gly Gly Gly Thr Lys Leu Glu Ile Lys
            100                 105
```

```
<210> SEQ ID NO 16
<211> LENGTH: 107
<212> TYPE: PRT
<213> ORGANISM: Mus musculus

<400> SEQUENCE: 16
```

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
                20                  25                  30

Leu Asn Trp Tyr Gln Gln Lys Pro Asp Gly Thr Val Thr Leu Leu Ile
            35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Arg
                85                  90                  95

Thr Phe Gly Gly Gly Thr Lys Leu Glu Ile Lys
            100                 105
```

```
<210> SEQ ID NO 17
<211> LENGTH: 32
<212> TYPE: DNA
<213> ORGANISM: Artificial Sequence
<220> FEATURE:
```

<223> OTHER INFORMATION: Synthetic construct

<400> SEQUENCE: 17
atacgtctct aggtgacacg ggttgtgcgg tg                                          32

<210> SEQ ID NO 18
<211> LENGTH: 30
<212> TYPE: DNA
<213> ORGANISM: Artificial Sequence
<220> FEATURE:
<223> OTHER INFORMATION: Synthetic construct

<400> SEQUENCE: 18
gcgtctagat taggccgata cctgtgattt                                            30

<210> SEQ ID NO 19
<211> LENGTH: 24
<212> TYPE: DNA
<213> ORGANISM: Artificial Sequence
<220> FEATURE:
<223> OTHER INFORMATION: Synthetic construct

<400> SEQUENCE: 19
ggattattca taccgtccca ccat                                                  24

<210> SEQ ID NO 20
<211> LENGTH: 26
<212> TYPE: DNA
<213> ORGANISM: Artificial Sequence
<220> FEATURE:
<223> OTHER INFORMATION: Synthetic construct

<400> SEQUENCE: 20
ctgggtgtag cgtcgtaagc taatac                                                26

<210> SEQ ID NO 21
<211> LENGTH: 354
<212> TYPE: DNA
<213> ORGANISM: Artificial Sequence
<220> FEATURE:
<223> OTHER INFORMATION: Synthetic construct

<400> SEQUENCE: 21
gatgtgcagc ttcaggagtc aggacctgac ctggtgaaac cttctcagtc actttcactc          60
acctgcactg tcactggcta ctccatcacc agtggttata actggcactg gatccggcag         120
tttccaggaa acaaactgga atggatgggc tacatacact acagtggtgg cactaactac         180
aacccatctc tcaaaagtcg aatctctatc actcgagaca catccaagaa ccagttcttc         240
ctgcagttga attctgtgac tactgaggac acagccacat attactgtgc aagaaggact         300
gggacggtcc cgtttgctta ctggggccaa gggactctgg tcactgtctc tgca              354

<210> SEQ ID NO 22
<211> LENGTH: 351
<212> TYPE: DNA
<213> ORGANISM: Artificial Sequence
<220> FEATURE:
<223> OTHER INFORMATION: Synthetic construct

<400> SEQUENCE: 22
gaggtccagc tgcagcagtc tggacctgag ctggtaaagc ctggggcttc agtgaagatg          60
tcctgcaagg cttctggata cacattcact agctatgtta tgcactgggt gaagcagaag         120
cctgggcagg gccttgagtg gattggatat cttaatcctt acaatgatga tactaagtac         180

-continued

```
aatgagaagt tcaaaggcaa ggccacactg acttcagaca aatcctccag cacagcctac      240
atggagctca gcagcctgac ctctgaggac tctgcggtct attactgtgc ctacggccct      300
ccctatgctt tggactactg gggtcaagga acctcagtca ccgtctcctc a               351

<210> SEQ ID NO 23
<211> LENGTH: 324
<212> TYPE: DNA
<213> ORGANISM: Artificial Sequence
<220> FEATURE:
<223> OTHER INFORMATION: Synthetic construct

<400> SEQUENCE: 23
gaaattgtgc tcacccagtc tccagcactc atggctgcat ctccagggga gaaggtcacc       60
atcacctgca gtgtcagctc aagtataagt tccagcaact tgcactggta ccagcagaag      120
tcagaaacct cccccaaacc ctggatttat ggcacatcca acctggcttc tggagtccct      180
gttcgcttca gtggcagtgg atctgggacc tcttattctc tcacaatcag cagtatggag      240
gctgaagatg ctgccactta ttactgtcaa cagtggagta gttacccact cacgttcgga      300
gggggaccaa gctggaaat aaaa                                             324

<210> SEQ ID NO 24
<211> LENGTH: 321
<212> TYPE: DNA
<213> ORGANISM: Artificial Sequence
<220> FEATURE:
<223> OTHER INFORMATION: Synthetic construct

<400> SEQUENCE: 24
gatatccaga tgacacagac tacatcctcc ctgtctgcct ctctgggaga cagagtcacc       60
atcagttgca gggcaagtca ggacattagc aattatttaa actggtatca gcagaaacca      120
gatggaactg ttacactcct gatctactac acatcaagat tacactcagg agtcccatca      180
aggttcagtg gcagtgggtc tggaacagat tattctctca ccattagcaa cctggagcaa      240
gaagatattg ccacttactt ttgccaacag ggtaatacgc ttcctcggac gttcggtgga      300
ggcaccaagc tggaaatcaa a                                               321

<210> SEQ ID NO 25
<211> LENGTH: 18
<212> TYPE: DNA
<213> ORGANISM: Artificial Sequence
<220> FEATURE:
<223> OTHER INFORMATION: Synthetic construct

<400> SEQUENCE: 25
agtggttata actggcac                                                    18

<210> SEQ ID NO 26
<211> LENGTH: 48
<212> TYPE: DNA
<213> ORGANISM: Artificial Sequence
<220> FEATURE:
<223> OTHER INFORMATION: Synthetic construct

<400> SEQUENCE: 26
tacatacact acagtggtgg cactaactac aacccatctc tcaaaagt                    48

<210> SEQ ID NO 27
<211> LENGTH: 27
<212> TYPE: DNA
```

<213> ORGANISM: Artificial Sequence
<220> FEATURE:
<223> OTHER INFORMATION: Synthetic construct

<400> SEQUENCE: 27
aggactggga cggtcccgtt tgcttac                                        27

<210> SEQ ID NO 28
<211> LENGTH: 24
<212> TYPE: DNA
<213> ORGANISM: Artificial Sequence
<220> FEATURE:
<223> OTHER INFORMATION: Synthetic construct

<400> SEQUENCE: 28
ggccctccct atgctttgga ctac                                          24

<210> SEQ ID NO 29
<211> LENGTH: 51
<212> TYPE: DNA
<213> ORGANISM: Artificial Sequence
<220> FEATURE:
<223> OTHER INFORMATION: Synthetic construct

<400> SEQUENCE: 29
tatcttaatc cttacaatga tgatactaag tacaatgaga agttcaaagg c            51

<210> SEQ ID NO 30
<211> LENGTH: 15
<212> TYPE: DNA
<213> ORGANISM: Artificial Sequence
<220> FEATURE:
<223> OTHER INFORMATION: Synthetic construct

<400> SEQUENCE: 30
agctatgtta tgcac                                                    15

<210> SEQ ID NO 31
<211> LENGTH: 36
<212> TYPE: DNA
<213> ORGANISM: Artificial Sequence
<220> FEATURE:
<223> OTHER INFORMATION: Synthetic construct

<400> SEQUENCE: 31
agtgtcagct caagtataag ttccagcaac ttgcac                             36

<210> SEQ ID NO 32
<211> LENGTH: 21
<212> TYPE: DNA
<213> ORGANISM: Artificial Sequence
<220> FEATURE:
<223> OTHER INFORMATION: Synthetic construct

<400> SEQUENCE: 32
ggcacatcca acctggcttc t                                             21

<210> SEQ ID NO 33
<211> LENGTH: 27
<212> TYPE: DNA
<213> ORGANISM: Artificial Sequence
<220> FEATURE:
<223> OTHER INFORMATION: Synthetic construct

<400> SEQUENCE: 33
caacagtgga gtagttaccc actcacg                                       27

<210> SEQ ID NO 34
<211> LENGTH: 33
<212> TYPE: DNA
<213> ORGANISM: Artificial Sequence
<220> FEATURE:
<223> OTHER INFORMATION: Synthetic construct

<400> SEQUENCE: 34
agggcaagtc aggacattag caattattta aac                                    33

<210> SEQ ID NO 35
<211> LENGTH: 27
<212> TYPE: DNA
<213> ORGANISM: Artificial Sequence
<220> FEATURE:
<223> OTHER INFORMATION: Synthetic construct

<400> SEQUENCE: 35
caacagggta atacgcttcc tcggacg                                           27

<210> SEQ ID NO 36
<211> LENGTH: 21
<212> TYPE: DNA
<213> ORGANISM: Artificial Sequence
<220> FEATURE:
<223> OTHER INFORMATION: Synthetic construct

<400> SEQUENCE: 36
tacacatcaa gattacactc a                                                 21

<210> SEQ ID NO 37
<211> LENGTH: 5
<212> TYPE: PRT
<213> ORGANISM: Mus musculus

<400> SEQUENCE: 37

Asp Thr Tyr Met His
1               5

<210> SEQ ID NO 38
<211> LENGTH: 17
<212> TYPE: PRT
<213> ORGANISM: Mus musculus

<400> SEQUENCE: 38

Tyr Leu Asn Pro Tyr Asn Asp Asp Thr Lys Tyr Asn Glu Lys Phe Lys Gly
1               5                   10                  15

<210> SEQ ID NO 39
<211> LENGTH: 17
<212> TYPE: PRT
<213> ORGANISM: Mus musculus

<400> SEQUENCE: 39

Gly Gly Ile Phe Tyr Tyr Tyr Gly Ser Ser Tyr Ser Tyr Ala Met Asp Tyr
1               5                   10                  15

<210> SEQ ID NO 40
<211> LENGTH: 12
<212> TYPE: PRT
<213> ORGANISM: Mus musculus

<400> SEQUENCE: 40

Thr Ala Ser Ser Ser Val Ser Ser Ser Tyr Leu His 1              5                    10

<210> SEQ ID NO 41
<211> LENGTH: 7
<212> TYPE: PRT
<213> ORGANISM: Mus musculus

<400> SEQUENCE: 41

Ser Thr Ser Asn Leu Ala Ser
1              5

<210> SEQ ID NO 42
<211> LENGTH: 9
<212> TYPE: PRT
<213> ORGANISM: Mus musculus

<400> SEQUENCE: 42

His Gln Tyr His Arg Ser Pro Tyr Thr
1              5

<210> SEQ ID NO 43
<211> LENGTH: 126
<212> TYPE: PRT
<213> ORGANISM: Mus musculus

<400> SEQUENCE: 43

Glu Val Gln Leu Gln Gln Ser Gly Ala Glu Leu Val Lys Pro Gly Ala
1              5                    10                   15

Ser Val Lys Leu Ser Cys Thr Ala Ser Gly Phe Asn Ile Lys Asp Thr
              20                   25                   30

Tyr Met His Trp Val Lys Gln Arg Pro Glu Gln Gly Leu Glu Trp Ile
          35                   40                   45

Gly Arg Ile Asp Pro Ala Asn Gly Asn Thr Gln Tyr Gly Pro Lys Phe
       50                   55                   60

Gln Gly Lys Ala Thr Ile Thr Ala Asp Thr Ser Ser Asn Thr Ala Tyr
65                   70                   75                   80

Leu Gln Leu Ser Ser Leu Thr Ser Glu Asp Thr Ala Val Tyr Tyr Cys
              85                   90                   95

Ala Arg Gly Gly Ile Phe Tyr Tyr Tyr Gly Ser Ser Tyr Ser Tyr Ala
          100                  105                  110

Met Asp Tyr Trp Gly Gln Gly Thr Ser Val Thr Val Ser Ser
          115                  120                  125

<210> SEQ ID NO 44
<211> LENGTH: 108
<212> TYPE: PRT
<213> ORGANISM: Mus musculus

<400> SEQUENCE: 44

Gln Ile Val Leu Thr Gln Ser Pro Ala Ile Met Thr Ala Ser Leu Gly
1              5                    10                   15

Glu Arg Val Thr Met Thr Cys Thr Ala Ser Ser Ser Val Ser Ser Ser
              20                   25                   30

Tyr Leu His Trp Tyr Gln Gln Lys Pro Gly Ser Ser Pro Lys Leu Trp
          35                   40                   45

Ile Tyr Ser Thr Ser Asn Leu Ala Ser Gly Val Pro Ala Arg Phe Ser
       50                   55                   60

Gly Ser Gly Ser Gly Thr Ser Tyr Ser Leu Thr Ile Ser Ser Met Glu
65                   70                   75                   80

```
Ala Glu Asp Ala Ala Thr Tyr Tyr Cys His Gln Tyr His Arg Ser Pro
             85                  90                      95

Tyr Thr Phe Gly Gly Gly Thr Lys Leu Glu Ile Lys
            100                 105
```

ANTIBODIES WHICH SPECIFICALLY BIND TO DENGUE VIRUS SEROTYPE 4 (DENV4) NON-STRUCTURAL PROTEIN 1 (NS1) AND METHODS OF USE THEREOF TO DETECT A DENV4 INFECTION

CROSS-REFERENCE TO RELATED APPLICATIONS

This application is a Continuation-in-Part of U.S. application Ser. No. 16/310,964 filed Dec. 18, 2018, now U.S. Pat. No. 11,407,818 issued Aug. 9, 2022, which is a 35 U.S.C. § 371 National Phase Application of International PCT Patent Application No. PCT/US2017/038703, filed Jun. 22, 2017, which application claims the benefit and priority to U.S. Provisional Patent Application No. 62/353,690, filed on 23 Jun. 2016 and entitled DENGUE VIRUS NON-STRUCTURAL PROTEIN 1 SPECIFIC BINDING POLYPEPTIDES AND METHODS OF USING THE SAME, the contents of each of which are hereby incorporated herein by reference in their entireties for all purposes.

GOVERNMENT FUNDING

Research supporting this application was carried out by the United States of America as represented by the Secretary, Department of Health and Human Services. This research was supported by the Intramural Research Program. The Government has certain rights in this invention.

SEQUENCE LISTING

In compliance with 37 C.F.R. § 1.52(e)(5), the sequence information contained in electronic file name: Sequence-_Listing_As_Filed.txt; size 15,012 bytes; and the date of creation: Jan. 12, 2022, is hereby incorporated herein by reference in its entirety.

BACKGROUND

1. Field

The present description relates to polypeptides, e.g., antibodies or an antigen-binding fragment thereof, methods of producing the same, and methods for the treatment and prevention of disease using compositions of the present disclosure.

2. Background

The four dengue virus serotypes (DENV-1 to DENV-4) are extremely important arthropod-borne flaviviruses in terms of morbidity and geographic distribution. Up to 400 million DENV infections occur every year, mostly in tropical and subtropical areas where vector mosquitos are abundant. Infection with any of the DENV may be asymptomatic or may lead to classic dengue fever or more severe dengue hemorrhagic fever (DHF) and dengue shock syndrome (DSS), which are increasingly common in the dengue endemic areas. Immunity to the same virus serotype (homotypic immunity) is life-long to that serotype. However, within 2-3 months after infection one is susceptible to other serotype.

Dengue is a serious disease of public importance with increasing worldwide spread. Dengue is caused by infection with any one of the four antigenically distinct dengue virus serotypes (DENV1-4). At the present, there is no efficacious vaccine and therapeutic agent. Current diagnosis of an acute DENV infection primarily relies on reverse transcriptase polymerase chain reaction (RT-PCR), a highly sophisticated test. To improve dengue case detection in dengue endemic countries a highly sensitive, specific, and simple rapid assay is needed to provide early support for patients and to accurately differentiate dengue from other acute febrile illnesses. DENV non-structural protein 1 (NS1) is a unique diagnostic marker for early detection of DENV because it is detected in the serum of DENV-infected patients as early as one day post onset of symptoms (DPO) to 18 DPO at concentrations up to 50 µg/mL.

NS1 is a highly conserved glycoprotein and possesses both group-specific and serotype-specific epitopes hence it has the potential to differentiate between DENV serotypes.

Rapid tests such as the NS1 enzyme-linked immunosorbent assay (ELISA) are commercially available for DENV with relatively good sensitivity and specificity. Several recent studies have critically evaluated the performance of the current commercially available NS1 ELISA kits by the DENV serotypes. However, results from these studies demonstrated that these kits are less sensitive for the detection of DENV4. Additionally, these commercial tests had decreased sensitivity in detecting secondary dengue infections, common in dengue endemic countries. Commercially available NS1 antigen (Ag) tests of PLATELIA™ (Bio-Rad®, Hercules, California, USA) and Dengue Early (PANBIO® Diagnostics, Brisbane, Australia), for example, have shown to have low sensitivity to DENV4 infections. In addition, Dengue Early test showed 19% sensitivity to DENV4. Furthermore, when comparing the sensitivities between all DENV serotypes, and PLATELIA™ test had the lowest sensitivity for DENV (58.3%). Collectively, the data establishes that there is a need for a new NS1 Ag detection test/assay with higher sensitivity for DENV4.

In order to improve the performance of NS1 Ag detection tests/assays with higher sensitivity for DENV4, it is important to understand why the current NS1 Ag detection tests failed to detect DENV4 infections effectively. Almost all of the present commercial NS1 Ag detection tests are based on cross-reactive anti-NS1 monoclonal antibodies (MAbs) to all four DENV serotypes. Several studies have shown the absence of significant amino acid sequence variation in the epitopes of serotype-cross-reactive MAbs. This is consistent with the observation of other studies that there was no link between the NS1 gene (amino acid) sequence variation and the poor performance of Dengue Early (PANBIO®) for DENV4 detection. Factors other than NS1 gene (and/or amino acid) sequence variation may impact the bio-accessibility and/or binding of the conserved epitopes to MAbs depending on the serotype. For example, the bio-accessibility of the conserved epitopes may vary according to the serotype/genotype when the NS1 protein is folded and assembled to form a NS1 hexamer. It is therefore conceivable to consider that the common linear epitopes targeted by MAbs of commercial NS1 tests could be only partially accessible (i.e., partially inaccessible) on the NS1 hexameric isoform of DENV4.

Another factor that could contribute to the poor sensitivity of NS1 Ag detection tests/assays for DENV4 is the low level expression of NS1 in DENV4-infected patients as compared to dengue patients infected with the DENV1, DENV2 and DENV3, although this is not yet properly investigated. Further, most of the anti-NS1 MAbs that have been developed so far and could be utilized as reagents for development of the current commercial serotype cross-reactive NS1 Ag detection tests were generated from native and/or recombinant(r) NS1 of DENV1 and DENV2 immunization. NS1 capture ELISAs specific to DENV4 might improve the detection of DENV4 cases worldwide. Additionally, the serotype-specific NS1 Ag test can offer an opportunity to identify DENV serotype. As such, there is a need for the development of new DENV4 serotype-specific NS1 antibodies and assays that can detect NS1 in the serum of DENV4-infected patients at the lowest possible detection limit (LOD).

Production of a properly-folded soluble NS1 protein appears to be crucial for the development of MAbs, which are reactive to epitopes that are accessible on hexameric NS1. However, rNS1 expressed in traditional expression system, e.g. *Escherichia coli*, often results in insoluble aggregates (inclusion bodies). Isolation and purification of proteins expressed in this way require solubilization in strong detergents, such as SDS and urea, which could also lead to denaturation of the target protein. Refolding of denatured protein is possible, but attaining the correct three-dimensional configuration of the protein is not always achieved or even possible. Expression of rNS1 in *Spodoptera frugiperda* (Sf) insect cell lines such as Sf9 and Sf21 using a baculovirus expression system has been utilized as an attractive alternative but, at least in the inventors' experience (unpublished data), the expressed rNS1 protein was insoluble and required solubilization and refolding, which involves multiple complex steps.

Therefore, a need exists for a DENV4 specific anti-NS1 antibody, especially an antibody directed to epitopes available on hexameric DENV4 NS1, and sensitive assays/tests directed to specifically detecting DENV4. In order to circumvent these problems, an expression system that generates soluble and stable rNS1 protein is required.

SUMMARY

The present disclosure relates to the surprising and unexpected discovery of antibodies that bind specifically to DENV4 NS1 (i.e., binds with high affinity relative to other DENV4 serotypes), methods of producing antibodies directed to multimeric (e.g., hexameric, DENV4 NS1), methods of detecting DENV4, and methods of treating and/or preventing DENV4 infections.

Thus, in certain aspects, the present disclosure provides antibodies and antigen-binding fragments thereof that bind specifically to Dengue virus serotype 4 (DENV4). In certain embodiments, the antibody or antigen binding fragment thereof comprises: a heavy chain variable region that comprises at least one CDR amino acid sequence selected from the group consisting of: SGYNWH (SEQ ID NO: 1), YIHYSGGTNYNPSLKS (SEQ ID NO: 2), RTGTVPFAY (SEQ ID NO: 3), SYVMH (SEQ ID NO: 4), YLNPYNDDT-KYNEKFKG (SEQ ID NO: 5), GPPYALDY (SEQ ID NO: 6), DTYMH (SEQ ID NO: 37), YLNPYNDDT-KYNEKFKG (SEQ ID NO: 38), and GGIFYYYGSSYS-YAMDY (SEQ ID NO: 39).

In certain embodiments, the fragment of the antibody is selected from the group consisting of a Fab fragment, a F(ab)', a F(ab)'$_2$ fragment, or a single-chain variable fragments (scFvs).

In some embodiments, the antibody or fragment thereof is specific for the DENV Non-structural protein 1 (NS1). In certain embodiments, the antibody or fragment thereof binds specifically to DENV4 NS1.

In other embodiments, the antibody or fragment thereof further comprises a light chain variable region that includes at least one CDR amino acid sequence selected from the group consisting of: SVSSSISSSNLH (SEQ ID NO: 7), GTSNLAS (SEQ ID NO: 8), QQWSSYPLT (SEQ ID NO: 9), RASQDISNYLN (SEQ ID NO: 10), YTSRLHS (SEQ ID NO: 11), QQGNTLPRT (SEQ ID NO: 12), TASSSVSS-SYLH (SEQ ID NO: 40), STSNLAS (SEQ ID NO: 41), and HQYHRSPYT (SEQ ID NO: 42).

In certain embodiments, the CDR amino acid sequence of the heavy chain variable region is selected from the group consisting of: SGYNWH (SEQ ID NO: 1), YIHYSGGTNYNPSLKS (SEQ ID NO: 2), and RTGTVP-FAY (SEQ ID NO: 3); and the CDR amino acid sequence of the light chain variable region is selected from the group consisting of: SVSSSISSSNLH (SEQ ID NO: 7), GTSN-LAS (SEQ ID NO: 8), and QQWSSYPLT (SEQ ID NO: 9).

In certain other embodiments, the CDR amino acid sequence of the heavy chain variable region is selected from the group consisting of: SYVMH (SEQ ID NO: 4), YLNPYNDDTKYNEKFKG (SEQ ID NO: 5), and GPPY-ALDY (SEQ ID NO: 6); and the CDR amino acid sequence of the light chain variable region is selected from the group consisting of: RASQDISNYLN (SEQ ID NO: 10), YTSRLHS (SEQ ID NO: 11), and QQGNTLPRT (SEQ ID NO: 12).

In particular embodiments, the heavy chain variable region comprises the amino acid sequence of.

```
                                        (SEQ ID NO: 13)
DVQLQESGPDLVKPSQSLSLTCTVTGYSITSGYNWHWIRQFPGNKLEWM

GYIHYSGGTNYNPSLKSRISITRDTSKNQFFLQLNSVTTEDTATYYCAR

RTGTVPFAYWGQGTLVTVSA,
```

```
                                        (SEQ ID NO: 14)
EVQLQQSGPELVKPGASVKMSCKASGYTFTSYVMHWVKQKPGQGLEWIG

YLNPYNDDTKYNEKFKGKATLTSDKSSSTAYMELSSLTSEDSAVYYCAY

GPPYALDYWGQGTSVTVSS,
or
```

```
                                        (SEQ ID NO: 43)
EVQLQQSGAELVKPGASVKLSCTASGFNIKDTYMHWVKQRPEQGLEWIG

RIDPANGNTQYGPKFQGKATITADTSSNTAYLQLSSLTSEDTAVYYCAR

GGIFYYYGSSYSYAMDYWGQGTSVTVSS.
```

In particular other embodiments, the light chain variable region comprises the amino acid sequence of:

```
                                        (SEQ ID NO: 15)
EIVLTQSPALMAASPGEKVTITCSVSSSISSSNLHWYQQKSETSPKPW

IYGTSNLASGVPVRFSGSGSGTSYSLTISSMEAEDAATYYCQQWSSYP

LTFGGGTKLEIK,
```

```
                                        (SEQ ID NO: 16)
DIQMTQTTSSLSASLGDRVTISCRASQDISNYLNWYQQKPDGTVTLLI

YYTSRLHSGVPSRFSGSGSGTDYSLTISNLEQEDIATYFCQQGNTLPR

TFGGGTKLEIK,
or
```

```
                                        (SEQ ID NO: 44)
QIVLTQSPAIMTASLGERVTMTCTASSSVSSSYLHWYQQKPGSSPKLW

IYSTSNLASGVPARFSGSGSGTSYSLTISSMEAEDAATYYCHQYHRSP

YTFGGGTKLEIK.
```

In yet other embodiment, the heavy chain variable region comprises the amino acid sequence of: DVQLQESGPDLVKPSQSLSLTCTVTGYSITSGYN-WHWIRQFPGNKLEWMGYIHYSGGTN YNPSLKSRISITRDTSKNQFFLQLNSVTTEDTATYY-CARRTGTVPFAYWGQGTLVTVSA (SEQ ID NO: 13); and the light chain variable region comprises the amino acid sequence of

```
                                      (SEQ ID NO: 15)
EIVLTQSPALMAASPGEKVTITCSVSSSISSSNLHWYQQKSETSPKPW

IYGTSNLASGVPVRFSGSGSGTSYSLTISSMEAEDAATYYCQQWSSYP

LTFGGGTKLEIK.
```

In some embodiments, the heavy chain variable region comprises the amino acid sequence of EVQLQQSGPEL-VKPGASVKMSCKASGYTFTSYVMHWVKQKPGQ-GLEWIGYLNPYNDD TKYNEKFKGKATLT-SDKSSSTAYMELSSLTSEDSAVYYCAYGPPYALDYW GQGTSVTV SS (SEQ ID NO: 14); and the light chain variable region comprises the amino acid sequence of

```
                                      (SEQ ID NO: 16)
DIQMTQTTSSLSASLGDRVTISCRASQDISNYLNWYQQKPDGTVTLLI

YYTSRLHSGVPSRFSGSGSGTDYSLTISNLEQEDIATYFCQQGNTLPR

TFGGGTKLEIK.
```

In some embodiments, the heavy chain variable region comprises the amino acid sequence of EVQLQQSGAEL-VKPGASVKLSCTASGFNIKDTYMHWVKQRPEQ-GLEWIGRIDPANGNT QYGPKFQGKATITADTSSN-TAYLQLSSLTSEDTAVYYCARGGIFYYYGSSYSYAM DYW GQGTSVTVSS (SEQ ID NO: 43); and the light chain variable region comprises the amino acid sequence of

```
                                      (SEQ ID NO: 16)
DIQMTQTTSSLSASLGDRVTISCRASQDISNYLNWYQQKPDGTVTLLI

YYTSRLHSGVPSRFSGSGSGTDYSLTISNLEQEDIATYFCQQGNTLPR

TFGGGTKLEIK.
```

In some embodiments, the heavy chain variable region comprises the amino acid sequence of EVQLQQSGPEL-VKPGASVKMSCKASGYTFTSYVMHWVKQKPGQ-GLEWIGYLNPYNDD TKYNEKFKGKATLT-SDKSSSTAYMELSSLTSEDSAVYYCAYGPPYALDYW GQGTSVTV SS (SEQ ID NO: 14); and the light chain variable region comprises the amino acid sequence of

```
                                      (SEQ ID NO: 44)
QIVLTQSPAIMTASLGERVTMTCTASSSVSSSYLHWYQQKPGSSPKLW

IYSTSNLASGVPARFSGSGSGTSYSLTISSMEAEDAATYYCHQYHRSP

YTFGGGTKLEIK.
```

In an embodiment, the antibody is 3H7A9, 6D4B10, or 8A6F2.

In some embodiments, antibody 3H7A9 comprises the light chain variable region comprising the CDR sequences of RASQDISNYLN (SEQ ID NO: 10), YTSRLHS (SEQ ID NO: 11), and QQGNTLPRT (SEQ ID NO: 12), and the heavy chain variable region comprising the CDR sequences of DTYMH (SEQ ID NO: 37), YLNPYNDDTKYNEKFKG (SEQ ID NO: 38), and GGIFYYYGSSYSYAMDY (SEQ ID NO: 39). In an embodiment, antibody 3H7A9 comprises the light chain variable region comprising the sequence of DIQMTQTTSSLSASLGDRVTISCRASQDIS-NYLNWYQQKPDGTVTLLIYYTSRLHSGVPS RFSGSGSGTDYSLTISNLEQEDIATYFCQQGNTL-PRTFGGGTKLEIK (SEQ ID NO: 16) and the heavy chain variable region comprising the sequence of

```
                                      (SEQ ID NO: 43)
EVQLQQSGAELVKPGASVKLSCTASGFNIKDTYMHWVKQRPEQGLEWI

GRIDPANGNTQYGPKFQGKATITADTSSNTAYLQLSSLTSEDTAVYYC

ARGGIFYYYGSSYSYAMDYWGQGTSVTVSS.
```

In some embodiments, antibody 6D4B10 comprises the heavy chain variable region comprising the CDR sequences of SYVMH (SEQ ID NO: 4), YLNPYNDDTKYNEKFKG (SEQ ID NO: 5), and GPPYALDY (SEQ ID NO: 6) and the light chain variable region comprising the CDR sequences of TASSSVSSSYLH (SEQ ID NO: 40), STSNLAS (SEQ ID NO: 41), and HQYHRSPYT (SEQ ID NO: 42). In an embodiment, antibody 6D4B10 comprises the heavy chain variable region comprising the sequence of EVQLQQSG-PELVKPGASVKMSCKASGYTFT-SYVMHWVKQKPGQGLEWIGYLNPYNDD TKYNEKFKGKATLTSDKSSSTAYMELSSLTSED-SAVYYCAYGPPYALDYWGQGTSVTV SS (SEQ ID NO: 14) and the light chain variable region comprising the sequence of

```
                                      (SEQ ID NO: 44)
QIVLTQSPAIMTASLGERVTMTCTASSSVSSSYLHWYQQKPGSSPKLW

IYSTSNLASGVPARFSGSGSGTSYSLTISSMEAEDAATYYCHQYHRSP

YTFGGGTKLEIK.
```

In some embodiments, antibody 8A6F2 comprises the heavy chain variable region comprising the CDR sequences of SGYNWH (SEQ ID NO: 1), YIHYSGGTNYNPSLKS (SEQ ID NO: 2), and RTGTVPFAY (SEQ ID NO: 3) and the light chain variable region comprising the CDR sequences of SVSSSISSSNLH (SEQ ID NO: 7), GTSNLAS (SEQ ID NO: 8), QQWSSYPLT (SEQ ID NO: 9). In an embodiment, antibody 8A6F2 comprises the heavy chain variable region comprising the sequence of DVQLQESGPDLVKP-SQSLSLTCTVTGYSITSGYNWHWIRQFPGN-KLEWMGYIHYSGGTN YNPSLKSRISITRDTSKNQF-FLQLNSVTTEDTATYYCARRTGTVPFAYWGQGTLVTV-SA (SEQ ID NO: 13) and the light chain variable region comprises the amino acid sequence of

```
                                      (SEQ ID NO: 15)
EIVLTQSPALMAASPGEKVTITCSVSSSISSSNLHWYQQKSETSPKPW

IYGTSNLASGVPVRFSGSGSGTSYSLTISSMEAEDAATYYCQQWSSYP

LTFGGGTKLEIK.
```

In an additional embodiment, the antibody fragment includes an antigen-binding site/region from an antibody selected from the group consisting of 3H7A9, 6D4B10 or 8A6F2.

In an additional aspect, the description provides a hybridoma that expresses an antibody selected from the group consisting of 3H7A9, 6D4B10, 8A6F2, or a fragment thereof that includes an antigen-binding site/region from an antibody selected from the group consisting of 3H7A9, 6D4B10 or 8A6F2, respectively.

An antibody or antigen-binding fragment thereof that binds specifically to Dengue virus serotype 4 (DENV4), wherein the antibody is: 8A6F2 or the antigen-binding fragment comprises at least at least one heavy chain or light chain CDR amino acid sequence from an antigen-binding site/region of 8A6F2; 3H7A9 or the antigen-binding fragment comprises at least at least one heavy chain or light chain CDR amino acid sequence from an antigen-binding site/region of 3H7A9; or 6D4B10 or the antigen-binding fragment comprises at least at least one heavy chain or light chain CDR amino acid sequence from an antigen-binding site/region of 6D4B10.

An additional aspect of the present disclosure provides a pharmaceutical composition. The composition comprises the antibody (or an antigen-binding fragment thereof) of the present disclosure and a pharmaceutically acceptable carrier.

Another aspect of the present disclosure provides a method of diagnosing or detecting a DENV4 infection. The method comprises: contacting a sample from a patient with the antibody (or an antigen-binding fragment thereof) of present disclosure; detecting the binding of NS1, wherein detection of DENV4 NS1 is indicative of a patient that is positive for DENV4 infection. In certain embodiments, the antibody is a labeled antibody or detected by a labeled antibody. In certain embodiments, the method further includes the step of quantifying the binding of the antibody to NS1 of DENV4. In certain embodiments, the method further includes the step of diagnosing the patient as having or not having a DENV4 infection. In certain embodiments the method further includes the step of administering an effective amount of a treatment effective for ameliorating at least one symptom of DENV4 infection.

In some embodiments, contacting the blood sample comprises: contacting the blood sample to an immobilized antibody (or an antigen-binding fragment thereof) of the present disclosure; and contacting the antibody retained DENV4 virion with a second antibody (or an antigen-binding fragment thereof) of the present disclosure. In an embodiment, the immobilized antibody (or the fragment thereof) and the second antibody (or the fragment thereof) are different antibodies or fragments thereof.

In other embodiments, the secondary antibody or a fragment thereof is linked to a detectable label. For example, the detectable label may be selected from the group consisting of an enzyme, biotin, streptavidin, a radioactive molecule, and an immunofluorescent protein or dye. In certain embodiments, when the detectable label is biotin or streptavidin, the method further comprises contacting a complex comprising a NS1 and the labeled antibody with a detection molecule that comprises streptavidin or biotin, respectively, linked to an immunofluorescent protein or dye, or an enzyme.

In further embodiments, the antibody or fragment thereof is linked to a detectable label and optionally a bead, particle, or nanoparticle. In an embodiment, the bead, particle, or nanoparticle is a magnetic bead.

In certain embodiments, the method further comprises separating a complex comprising NS1 and the labeled antibody or fragment thereof via the bead, particle or nanoparticle for detecting the binding of NS1. In an embodiment, the sample comprises a blood or a tissue sample.

A further aspect of the present disclosure provides a method of treating a DENV4 infection in a subject. The method comprises: administering to a subject in the need thereof an effective amount of the antibody (or a fragment thereof) of the present disclosure or the pharmaceutical composition of the present disclosure, wherein the administering is effective at treating the infection.

In an embodiment, the antibody (or antigen-binding fragment thereof) is a humanized antibody or antigen-binding fragment thereof.

Additional embodiments relate to a method for preventing or treating dengue virus infection or a symptom thereof in a mammal including providing to the mammal a prophylactically or therapeutically effective amount of the composition of any of the embodiments disclosed herein. This method can involve identifying a mammal in need of an agent that prevents or treats dengue virus infection or a symptom thereof. The identification can be by clinical evaluation or evaluation by diagnostic approach. Some embodiments relate to measuring a marker of dengue virus infection or a symptom thereof in said mammal. The measurement can be a measurement of viral load in the mammal.

An additional aspect of the present disclosure provides a method of producing/making a DENV NS1 specific antibody or fragment thereof. The method comprises: providing a nucleic acid expressing DENV NS1 fusion protein with a solubility and stability tag; producing a multimeric DENV NS1 complex; and immunizing an animal with the multimeric DENV NS1 complex, wherein immunizing the animal produces an antibody specific to the DENV NS1. For example, the animal may be a chicken, a goat, a guinea pig, a hamster, a horse, a mouse, a rat, or a sheep. The multimeric DENV NS1 complex may comprise 2, 3, 4, 5, 6, or more DENV NS1 fusion proteins.

In some embodiments, the method further comprises preparing at least one hybridoma from spleen cells of the immunized animal.

In additional embodiments, the solubility and stability tag includes a secretion signal.

In certain embodiments, the solubility and stability tag is a small ubiquitin-like modifier (SUMO) and/or the secretion signal is gp67.

In other particular embodiments, providing the nucleic acid expressing DENV NS1 fusion protein comprises inserting the Dengue virus NS1 into a vector comprising the solubility and stability tag and optionally, the secretion signal.

In an embodiment, the DENV NS1 is a DENV4 NS1.

In other embodiments, producing the multimeric DENV NS1 complex is performed with a eukaryotic expression system. In a particular embodiment, the eukaryotic expression system may be a baculovirus expression system or a vaccinia virus expression system.

In certain embodiments, the producing a multimeric DENV NS1 complex may include a host cell comprising a vector that expresses a serotype specific DENV NS1 antibody. In another embodiment, the host cell can be a eukaryotic cell, such as a Chinese hamster ovary (CHO) cell, a NS0 murine myeloma cell, or a human embryonic retinal cell, PER.C6® human cell, an insect cell line, Sf9, or Sf21.

In further embodiment, producing a multimeric DENV NS1 complex comprises infecting eukaryotic cells with a baculovirus expressing the DENV NS1 fusion protein.

In some embodiments, the baculovirus expressing the DENV NS1 fusion protein is prepared by at least one of: transforming a bacteria with a vector comprising the DENV NS1 fusion protein; selecting a vector-transformed bacteria; extracting/purifying the vector from the vector-transformed bacteria; transforming a bacteria comprising a baculovirus shuttle vector; selecting a bacteria with a recombinant DENV NS1 fusion protein-baculovirus vector; extracting/ purifying the recombinant DENV NS1 fusion protein-baculovirus vector; transfecting a eukaryotic cell with the recombinant DENV NS1 fusion protein-baculovirus vector; or collecting cell culture supernatant comprising the baculovirus expressing the DENV NS1 fusion protein.

In other embodiments, immunizing the animal with the multimeric DENV NS1 complex includes at least one of: administering the multimeric DENV NS1 complex to the animal at least two times; isolate at least one primed spleen cell from the animals; fusing the primed spleen cell with a myeloma cell; or selecting a hybridoma cell expressing the antibody specific to the DENV NS1.

In a particular embodiment, the method further comprises humanizing the antibody specific for DENV NS1.

In another embodiment, the method further comprises treating the antibody specific for DENV NS1 thereby producing a fragment thereof. In an embodiment, treating comprises contacting the antibody specific for DENV NS1 with an agent selected from the group consisting of (i) pepsin, (ii) papain, and (iii) pepsin and β-mercaptoethanol.

Other embodiments relate to a vector comprising the nucleic acid of the peptide of embodiments disclosed herein. Further embodiments relate to a host cell comprising the vector of embodiments disclosed herein.

Additional embodiments also relate to a cell expressing the antibody (or fragment thereof) of the present disclosure.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating an embodiment of the invention and are not to be construed as limiting the invention.

DETAILED DESCRIPTION

Figure 1:
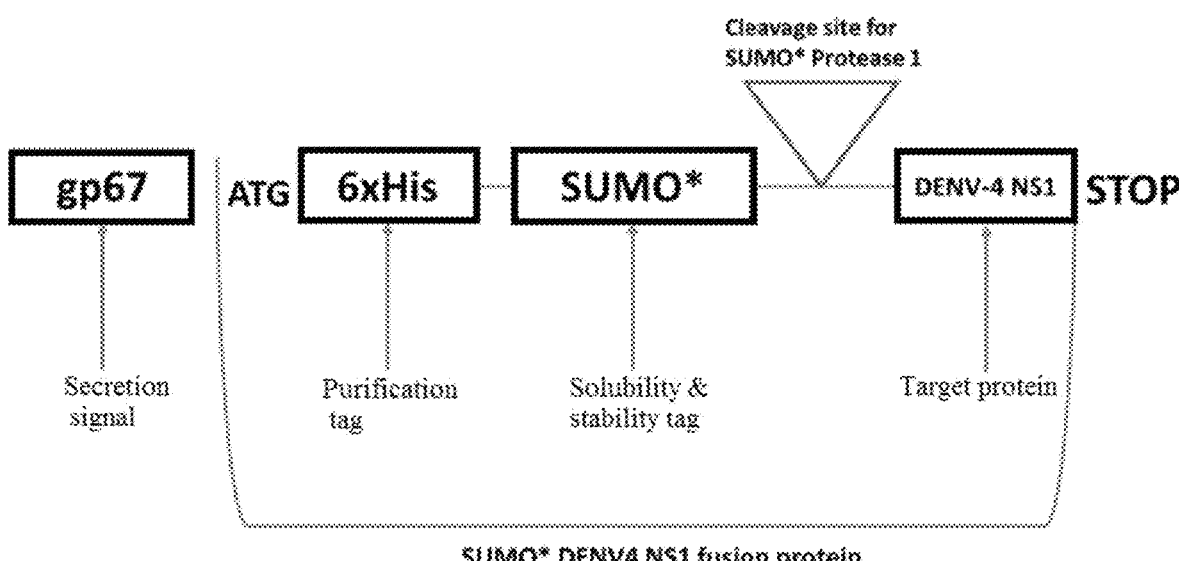
FIG. 1. SUMO*-NS1 fusion gene construct produced in accordance with the present disclosure.

As described herein, the composition or polypeptides of the present disclosure bind specifically to DENV4 NS1 (i.e., bind with high affinity relative to other DENV serotypes), treat and/or prevent a DENV4 infection, ameliorate the systems of a DENV4 infection, or any combination thereof, and therefore, the compositions and/or polypeptides of the present disclosure represent a novel therapeutic intervention for the treatment and/or prevention of, for example, DENV4 infections and tissue damage/injury caused therefrom.

Unless otherwise defined, all technical and scientific terms used herein have the same meaning as commonly understood by one of ordinary skill in the art to which this disclosure belongs. See, e.g., Singleton P and Sainsbury D., in Dictionary of Microbiology and Molecular Biology 3rd ed., J. Wiley & Sons, Chichester, New York, 2001. All publications, patent applications, patents, and other references mentioned herein are incorporated by reference in their entireties. In the case of conflict, the present specification, including definitions, will control. In addition, the examples are illustrative only and not intended to be limiting.

Where a range of values is provided, it is understood that each intervening value, to the tenth of the unit of the lower limit unless the context clearly dictates otherwise (such as in the case of a group containing a number of amino acids in which case each amino acid number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

The following terms are used to describe the present invention. In instances where a term is not specifically defined herein, that term is given an art-recognized meaning by those of ordinary skill applying that term in context to its use in describing the present invention.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The phrases "pharmaceutically or pharmacologically acceptable" refer to molecular entities and compositions that do not produce an adverse, allergic or other undesirable reaction when administered to an animal, or a human, as appropriate.

The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects, one or more of the present compounds described herein, are co-administered in combination with at least one additional bioactive agent, especially including an antiviral, pain reliever, and/or a palliative agent. In particularly preferred aspects, the co-administration of compounds results in synergistic activity and/or therapy, including antiviral and/or pain relief activity.

The term "amino acid side chain" refers to a moiety attached to the α-carbon in an amino acid. For example, the amino acid side chain for alanine is methyl, the amino acid side chain for phenylalanine is phenylmethyl, the amino acid side chain for cysteine is thiomethyl, the amino acid side chain for tyrosine is 4-hydroxyphenylmethyl, etc. Other non-naturally occurring amino acid side chains are also included for example, those that occur in nature (e.g., an amino acid metabolite) or those that are made synthetically (e.g., an alpha di-substituted amino acid).

The term polypeptide encompasses two or more naturally occurring or synthetic amino acids linked by a covalent bond (e.g., an amide bond). Polypeptides as described herein include full length proteins (e.g., fully processed proteins), as well as shorter amino acids sequences (e.g., fragments of naturally occurring proteins or synthetic polypeptide fragments).

Throughout the present specification and claims, the numbering of the residues in an immunoglobulin heavy chain is that of the EU index as in Kabat et al., Sequences of Proteins of Immunological Interest, 5th Ed. Public Health Service, National Institutes of Health, Bethesda, Md. (1991). The "EU index as in Kabat" refers to the residue numbering of the human IgG1 EU antibody.

The term "homology" is defined as the percentage of residues in a modified amino acid sequence that are identical after aligning the sequences and introducing gaps, if necessary, to achieve the maximum percent homology. Methods and computer programs for the alignment are well known in the art. One such computer program is "ClustalW, which is available, for example, on the world-wide web at ebi.ac.uk/clustalw.

An "amino acid modification" refers to a change in the amino acid sequence of a predetermined amino acid sequence. Exemplary modifications include an amino acid substitutions, insertions and/or deletions. The preferred amino acid modification herein is a conservative substitution.

An "amino acid substitution" refers to the replacement of at least one existing amino acid residue in a predetermined amino acid sequence with another different "replacement" amino acid residue. The replacement residue or residues may be "naturally occurring amino acid residues" (i.e., encoded by the genetic code) and selected from the group consisting of alanine (Ala); arginine (Arg); asparagine (Asn); aspartic acid (Asp); cysteine (Cys); glutamine (Gln); glutamic acid (Glu); glycine (Gly); histidine (His); isoleucine (Leu): leucine (Leu); lysine (Lys); methionine (Met); phenylalanine (Phe); proline (Pro); serine (Ser); threonine (Thr); tryptophan (Trp); tyrosine (Tyr); and valine (Val). Preferably, the replacement residue is not cysteine. Substitution with one or more non-naturally occurring amino acid residues is also encompassed by the definition of an amino acid substitution herein. A "non-naturally occurring amino acid residue" refers to a residue, other than those naturally occurring amino acid residues listed above, which is able to covalently bind adjacent amino acid residues(s) in a polypeptide chain. Examples of non-naturally occurring amino acid residues include norleucine, ornithine, norvaline, homoserine and other amino acid residue analogues.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

An "amino acid insertion" refers to the incorporation of at least one amino acid into a predetermined amino acid sequence.

An "amino acid deletion" refers to the removal of at least one amino acid residue from a predetermined amino acid sequence.

"Hinge region" is generally defined as stretching from Glu216 to Pro230 of human IgG1. Hinge regions of other IgG isotypes may be aligned with the IgG1 sequence by placing the first and last cysteine residues forming inter-heavy chain S—S bonds in the same positions.

The term "binding domain" refers to the region of a polypeptide that binds to another molecule.

The term "antibody" is used in the broadest sense and specifically covers monoclonal antibodies (including full length monoclonal antibodies), polyclonal antibodies, multi-specific antibodies (e.g., bispecific antibodies), and antibody fragments so long as they exhibit the desired biological activity.

"Antibody fragments" (i.e., an antigen-binding fragment of an antibody), as defined for the purpose of the present invention, comprise a portion of an intact antibody, generally including the antigen binding or variable region of the intact antibody and optionally the Fc region of an antibody. Examples of antibody fragments include linear antibodies; single-chain antibody molecules (e.g., scFv); F(ab')$_2$ fragments; Fab' fragments; and multi-specific antibodies formed from antibody fragments. The antibody fragments may retain at least part of the hinge and optionally the $C_H1$ region of an IgG heavy chain. The antibody fragments may retain the entire constant region of an IgG heavy chain, and include an IgG light chain.

The term "Fc region" is used to define a C-terminal region of an immunoglobulin heavy chain. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The Fc region of an immunoglobulin generally comprises two constant domains, $C_H2$ and $C_H3$.

The term "F(ab) fragment" is defined as a fragment of an immunoglobulin molecule that comprises the variable regions of a light chain and a heavy chain. That is, a Fab fragment is a monovalent antigen binding structure of an immunoglobulin without the Fc portion, and which results from the treatment of an immunoglobulin with papain.

The term "F(ab)' fragment" is defined as a fragment of an immunoglobulin molecule that comprises the variable regions of a light chain and a heavy chain. That is, the fragment is monovalent and most of the Fc portion is removed, which can be achieved through the treatment of an immunoglobulin molecule with pepsin and β-mercaptoethanol.

The term "F(ab')$_2$ fragment" is defined as a fragment of an immunoglobulin molecule that comprises two F(ab) fragments and a portion of the hinge region. That is, most of the Fc portion is removed, which can be achieved through the treatment of an immunoglobulin molecule with pepsin.

The term "single-chain variable fragments" (scFvs) is defined as a polypeptide engineered to comprise the variable regions (i.e., the antigen-binding domains) of a light immunoglobulin chain and a heavy immunoglobulin chain. The light chain and heavy chain can be joined by flexible linker sequence.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein 1975 *Nature* 256:495, or may be made by recombinant DNA methods. The "monoclonal antibodies" may also be isolated from phage antibody libraries.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

"Humanized" forms of non-human (e.g., murine) antibodies are chimeric antibodies that contain minimal sequence derived from non-human immunoglobulin. For the most part, humanized antibodies are human immunoglobu-lins (recipient antibody) in which residues from a hyper-variable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin.

The term "hypervariable region" when used herein refers to the amino acid residues of an antibody that are responsible for antigen-binding. The hypervariable region comprises amino acid residues from a "complementarity determining region" or "CDR" (i.e., residues 24-34 (L1), 50-56 (L2) and 89-97 (L3) in the light chain variable domain and 31-35 (H1), 50-65 (H2) and 95-102 (H3) in the heavy chain variable domain and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain). "Framework" or "FR" residues are those variable domain residues other than the hypervariable region residues as herein defined.

An "isolated" polypeptide is one that has been identified and separated and/or recovered from a component of its natural environment. Contaminant components of its natural environment are materials that would interfere with diag-nostic or therapeutic uses for the polypeptide, and may include enzymes, hormones, and other proteinaceous or nonproteinaceous solutes. In preferred embodiments, the polypeptide will be purified (1) to greater than 95% by weight of polypeptide as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver stain. Isolated polypeptide includes the polypeptide in situ within recombinant cells since at least one component of the polypeptide's natural environment will not be present. Ordinarily, however, isolated polypep-tides will be prepared by at least one purification step.

The term "patient" or "subject" is used throughout the specification to describe an animal, preferably a human or a domesticated animal, to whom treatment, including prophy-lactic treatment, with the compositions according to the present disclosure is provided. For treatment of those infec-tions, conditions or disease states which are specific for a specific animal such as a human patient, the term patient refers to that specific animal, including a domesticated animal such as a dog or cat or a farm animal such as a horse, cow, sheep, etc. In general, in the present disclosure, the term patient refers to a human patient unless otherwise stated or implied from the context of the use of the term.

By "effective amount" is meant the amount required to ameliorate the symptoms of a disease relative to an untreated patient. The effective amount of active compound(s), com-position, or component which, when used within the context of its intended use, effects an intended use. The therapeutic treatment of a disease varies depending upon the manner of administration, the age, body weight, and general health of the subject. Ultimately, the attending physician or veterinar-ian will decide the appropriate amount and dosage regimen. Such amount is referred to as an "effective" amount. The term effective subsumes all other effective amount or effec-tive concentration terms, which are otherwise described or used in the present application.

As used herein, "treatment", "treat", and "treating", and the like refers to both therapeutic treatment and prophylactic or preventative measures. Those in need of treatment include those already with the disorder, as well as those in which the disorder is to be prevented. As such, these terms refer to reducing or ameliorating a disorder and/or symptoms asso-ciated therewith. It will be appreciated that, although not precluded, treating a disorder or condition does not require that the disorder, condition or symptoms associated there-with be completely eliminated.

As used herein, "ameliorate", "ameliorating", or the like refers to decreasing, suppressing, attenuating, diminishing, arresting, or stabilizing the development or progression of a disease.

A "disorder" is any condition that would benefit from treatment with the polypeptide of the present disclosure. This includes chronic and acute disorders or diseases includ-ing those pathological conditions that predispose the mam-mal to the disorder in question. In one embodiment, the disorder is a viral infection (e.g., a dengue virus disease such as that which is caused by DENV4).

As used herein, the term "dengue virus disease" means any disease caused, directly or indirectly, by one of the four serotypes of a dengue virus, which is a flavivirus. Dengue is an acute febrile disease characterized by sudden onset, with headache, fever, prostration, joint and muscle pain, lymph-adenopathy, and a rash that appears simultaneously with a temperature rise. A second phase of temperature rise may appear following an afebrile period. Dengue hemorrhagic fever/dengue shock syndrome is an acute disease occurring primarily in children characterized by an abrupt febrile onset followed by hemorrhagic manifestations and circulatory collapse.

The word "label" when used herein refers to a detectable compound or composition that is conjugated directly or indirectly to the polypeptide. The label may itself be detect-able (e.g., radioisotope labels or fluorescent labels) or, in the case of an enzymatic label, may catalyze chemical alteration of a substrate compound or composition that is detectable.

An "isolated" nucleic acid molecule is a nucleic acid molecule that is identified and separated from at least one contaminant nucleic acid molecule with which it is ordinar-ily associated in the natural source of the polypeptide nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the polypeptide where, for example, the nucleic acid molecule is in a chromosomal location different from that of natural cells. The term "isolated" nucleic acids can mean: (1) amplified in vitro by, for example, polymerase chain reac-tion (PCR); (ii) recombinantly produced by cloning; (iii) purified, as by cleavage and gel separation; or (iv) synthe-sized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

As used herein with respect to polypeptides, the term "substantially pure" means that the polypeptides are essentially free of other substances with which they may be found in nature or in vivo systems to an extent practical and appropriate for their intended use. In particular, the polypeptides are sufficiently pure and are sufficiently free from other biological constituents of their host cells so as to be useful in, for example, generating antibodies, sequencing, or producing pharmaceutical preparations. By techniques well known in the art, substantially pure polypeptides may be produced in light of the nucleic acid and amino acid sequences disclosed herein. Because a substantially purified polypeptide of the invention may be admixed with a pharmaceutically acceptable carrier in a pharmaceutical preparation, the polypeptide may comprise only a certain percentage by weight of the preparation. The polypeptide is nonetheless substantially pure in that it has been substantially separated from the substances with which it may be associated in living systems.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification and selection of cells which have been transformed or transfected with the vector. Markers include, for example, genes encoding proteins which increase or decrease either resistance or sensitivity to antibiotics or other compounds, genes which encode enzymes whose activities are detectable by standard assays known in the art (e.g., B-galactosidase or alkaline phosphatase), and genes which visibly affect the phenotype of transformed or transfected cells, hosts, colonies or plaques. Preferred vectors are those capable of autonomous replication and expression of the structural gene products present in the DNA segments to which they are operably joined.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, synthetic oligonucleotide adaptors or linkers are used in accordance with conventional practice.

As used herein, the expressions "cell," "cell line," and "cell culture" are used interchangeably and all such designations include progeny. Thus, the words "transformants", "transformed cells", "transfectants", and "transfected cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed/transfected cell are included. Where distinct designations are intended, it will be clear from the context.

The term "molecular complex" when used herein refers to the relatively stable structure that forms when two or more heterologous molecules (e.g., polypeptides) bind (preferably noncovalently) to one another. The preferred molecular complex herein is an immune complex.

"Immune complex" refers to the relatively stable structure that forms when at least one target molecule and at least one polypeptide of the present disclosure bind to one another forming a larger molecular weight complex. Examples of immune complexes are antigen-antibody aggregates.

The term "target molecule" refers to a molecule, usually a polypeptide, which is capable of being bound by a heterologous molecule and has one or more binding sites for the heterologous molecule. The term "binding site" refers to a region of a molecule to which another molecule can bind.

Aspects of the present disclosure provide an antibody or an antigen-binding fragment thereof that specifically binds Dengue virus serotype 4 (DENV4), wherein the antibody or an antigen-binding fragment thereof comprises: a heavy chain variable region that comprises at least one CDR amino acid sequence selected from the group consisting of: SGYNWH (SEQ ID NO: 1), YIHYSGGTNYNPSLKS (SEQ ID NO: 2), RTGTVPFAY (SEQ ID NO: 3), SYVMH (SEQ ID NO: 4), YLNPYNDDTKYNEKFKG (SEQ ID NO: 5), GPPYALDY (SEQ ID NO: 6), DTYMH (SEQ ID NO: 37), YLNPYNDDTKYNEKFKG (SEQ ID NO: 38), and GGI-FYYYGSSYSYAMDY (SEQ ID NO: 39).

In certain embodiments, the antigen-binding fragment is selected from the group consisting of a Fab fragment, a F(ab)', a F(ab)'$_2$ fragment, or a single-chain variable fragments (scFvs).

In a particular embodiment, the CDR amino acid sequences of the heavy chain variable region are SGYNWH (SEQ ID NO: 1), YIHYSGGTNYNPSLKS (SEQ ID NO: 2), and RTGTVPFAY (SEQ ID NO: 3). In another particular embodiment, the CDR amino acid sequences of the heavy chain variable region are SYVMH (SEQ ID NO: 4), YLNPYNDDTKYNEKFKG (SEQ ID NO: 5), and GPPY-ALDY (SEQ ID NO: 6). In another particular embodiment, the CDR amino acid sequences of the heavy chain variable region are DTYMH (SEQ ID NO: 37), YLNPYNDDT-KYNEKFKG (SEQ ID NO: 38), and GGIFYYYGSSYS-YAMDY (SEQ ID NO: 39).

In some embodiments, the antibody or an antigen-binding fragment thereof is specific for the Non-structural protein 1 (NS1).

In other embodiments, the antibody or an antigen-binding fragment thereof further comprises a light chain variable region that includes at least one CDR amino acid sequence selected from the group consisting of: SVSSSISSSNLH (SEQ ID NO: 7), GTSNLAS (SEQ ID NO: 8), QQWSSY-PLT (SEQ ID NO: 9), RASQDISNYLN (SEQ ID NO: 10), YTSRLHS (SEQ ID NO: 11), QQGNTLPRT (SEQ ID NO: 12), TASSSVSSSYLH (SEQ ID NO: 40), STSNLAS (SEQ ID NO: 41), and HQYHRSPYT (SEQ ID NO: 42).

In a particular embodiment, the CDR amino acid sequences of the light chain variable region are SVSSSIS-SSNLH (SEQ ID NO: 7), GTSNLAS (SEQ ID NO: 8), and QQWSSYPLT (SEQ ID NO: 9). In another particular embodiment, the CDR amino acid sequences of the light chain variable region are RASQDISNYLN (SEQ ID NO: 10), YTSRLHS (SEQ ID NO: 11), and QQGNTLPRT (SEQ ID NO: 12). In another particular embodiment, the CDR amino acid sequences of the light chain variable region are TASSSVSSSYLH (SEQ ID NO: 40), STSNLAS (SEQ ID NO: 41), and HQYHRSPYT (SEQ ID NO: 42).

In certain embodiments, the CDR amino acid sequence of the heavy chain variable region is selected from the group consisting of: SGYNWH (SEQ ID NO: 1), YIHYSGGTNYNPSLKS (SEQ ID NO: 2), and RTGTVP-FAY (SEQ ID NO: 3); and the CDR amino acid sequence of the light chain variable region is selected from the group consisting of: SVSSSISSSNLH (SEQ ID NO: 7), GTSN-LAS (SEQ ID NO: 8), and QQWSSYPLT (SEQ ID NO: 9). For example, the antibody or an antigen-binding fragment thereof may include the CDR amino acid sequences of the heavy chain variable region are SGYNWH (SEQ ID NO: 1), YIHYSGGTNYNPSLKS (SEQ ID NO: 2), and RTGTVP-FAY (SEQ ID NO: 3), and the CDR amino acid sequences of the light chain variable region are SVSSSISSSNLH (SEQ ID NO: 7), GTSNLAS (SEQ ID NO: 8), and QQWSSYPLT (SEQ ID NO: 9).

In certain other embodiments, the CDR amino acid sequence of the heavy chain variable region is selected from the group consisting of: SYVMH (SEQ ID NO: 4), YLNPYNDDTKYNEKFKG (SEQ ID NO: 5), and GPPY-ALDY (SEQ ID NO: 6); and the CDR amino acid sequence of the light chain variable region is selected from the group consisting of: RASQDISNYLN (SEQ ID NO: 10), YTSRLHS (SEQ ID NO: 11), and QQGNTLPRT (SEQ ID NO: 12). For example, the antibody or an antigen-binding fragment thereof may include the CDR amino acid sequences of the heavy chain variable region are SYVMH (SEQ ID NO: 4), YLNPYNDDTKYNEKFKG (SEQ ID NO: 5), and GPPYALDY (SEQ ID NO: 6), and the CDR amino acid sequences of the light chain variable region are RASQDISNYLN (SEQ ID NO: 10), YTSRLHS (SEQ ID NO: 11), and QQGNTLPRT (SEQ ID NO: 12).

In certain other embodiments, the CDR amino acid sequence of the heavy chain variable region is selected from the group consisting of: SYVMH (SEQ ID NO: 4), YLNPYNDDTKYNEKFKG (SEQ ID NO: 5), and GPPY-ALDY (SEQ ID NO: 6); and the CDR amino acid sequence of the light chain variable region is selected from the group consisting of: TASSSVSSSYLH (SEQ ID NO: 40), STSN-LAS (SEQ ID NO: 41), and HQYHRSPYT (SEQ ID NO: 42). For example, the antibody or an antigen-binding fragment thereof may include the CDR amino acid sequences of the heavy chain variable region are SYVMH (SEQ ID NO: 4), YLNPYNDDTKYNEKFKG (SEQ ID NO: 5), and GPPYALDY (SEQ ID NO: 6), and the CDR amino acid sequences of the light chain variable region are TASSSVSS-SYLH (SEQ ID NO: 40), STSNLAS (SEQ ID NO: 41), and HQYHRSPYT (SEQ ID NO: 42).

In certain other embodiments, the CDR amino acid sequence of the heavy chain variable region is selected from the group consisting of: DTYMH (SEQ ID NO: 37), YLNPYNDDTKYNEKFKG (SEQ ID NO: 38), and GGI-FYYYGSSYSYAMDY (SEQ ID NO: 39); and the CDR amino acid sequence of the light chain variable region is selected from the group consisting of: RASQDISNYLN (SEQ ID NO: 10), YTSRLHS (SEQ ID NO: 11), and QQGNTLPRT (SEQ ID NO: 12). For example, the antibody or an antigen-binding fragment thereof may include the CDR amino acid sequences of the heavy chain variable region are DTYMH (SEQ ID NO: 37), YLNPYNDDT-KYNEKFKG (SEQ ID NO: 38), and GGIFYYYGSSYS-YAMDY (SEQ ID NO: 39), and the CDR amino acid sequences of the light chain variable region are RASQDIS-NYLN (SEQ ID NO: 10), YTSRLHS (SEQ ID NO: 11), and QQGNTLPRT (SEQ ID NO: 12).

In particular embodiments, the heavy chain variable region comprises the amino acid sequence of:

```
                                    (SEQ ID NO: 13)
DVQLQESGPDLVKPSQSLSLTCTVTGYSITSGYNWHWIRQFPGNKLEW

MGYIHYSGGTNYNPSLKSRISITRDTSKNQFFLQLNSVTTEDTATYYC

ARRTGTVPFAYWGQGTLVTVSA, (SEQ ID NO: 14)
EVQLQQSGPELVKPGASVKMSCKASGYTFTSYVMHWVKQKPGQGLEWI

GYLNPYNDDTKYNEKFKGKATLTSDKSSSTAYMELSSLTSEDSAVYYC

AYGPPYALDYWGQGTSVTVSS,
or
                                    (SEQ ID NO: 43)
EVQLQQSGAELVKPGASVKLSCTASGFNIKDTYMHWVKQRPEQGLEWI

GRIDPANGNTQYGPKFQGKATITADTSSNTAYLQLSSLTSEDTAVYYC

ARGGIFYYYGSSYSYAMDYWGQGTSVTVSS.
```

In particular other embodiments, the light chain variable region comprises the amino acid sequence of:

```
                                    (SEQ ID NO: 15)
EIVLTQSPALMAASPGEKVTITCSVSSSISSSNLHWYQQKSETSPKPWI

YGTSNLASGVPVRFSGSGSGTSYSLTISSMEAEDAATYYCQQWSSYPLT

FGGGTKLEIK,
```

-continued (SEQ ID NO: 16)
DIQMTQTTSSLSASLGDRVTISCRASQDISNYLNWYQQKPDGTVTLLIY

YTSRLHSGVPSRFSGSGSGTDYSLTISNLEQEDIATYFCQQGNTLPRTF

GGGTKLEIK,
or (SEQ ID NO: 44)
QIVLTQSPAIMTASLGERVTMTCTASSSVSSSYLHWYQQKPGSSPKLWI

YSTSNLASGVPARFSGSGSGTSYSLTISSMEAEDAATYYCHQYHRSPYT

FGGGTKLEIK.

In yet other embodiment, the heavy chain variable region comprises the amino acid sequence of DVQLQESGPDLVKPSQSLSLTCTVTGYSITSGYN-WHWIRQFPGNKLEWMGYIHYSGGTN YNPSLKSRISITRDTSKNQFFLQLNSVTTEDTATYY-CARRTGTVPFAYWGQGTLVTVSA (SEQ ID NO: 13); and the light chain variable region comprises the amino acid sequence of (SEQ ID NO: 15)
EIVLTQSPALMAASPGEKVTITCSVSSSISSSNLHWYQQKSETSPKPWI

YGTSNLASGVPVRFSGSGSGTSYSLTISSMEAEDAATYYCQQWSSYPLT

FGGGTKLEIK.

In some embodiments, the heavy chain variable region comprises the amino acid sequence of EVQLQQSGPEL-VKPGASVKMSCKASGYTFTSYVMHWVKQKPGQ-GLEWIGYLNPYNDD TKYNEKFKGKATLT-SDKSSSTAYMELSSLTSEDSAVYYCAYGPPYALDYW GQGTSVTV SS (SEQ ID NO: 14); and the light chain variable region comprises the amino acid sequence of (SEQ ID NO: 16)
DIQMTQTTSSLSASLGDRVTISCRASQDISNYLNWYQQKPDGTVTLLIY

YTSRLHSGVPSRFSGSGSGTDYSLTISNLEQEDIATYFCQQGNTLPRTF

GGGTKLEIK.

In some embodiments, the heavy chain variable region comprises the sequence of EVQLQQSGPELVKP-GASVKMSCKASGYTFTSYVMHWVKQKPGQGLEWI-GYLNPYNDD TKYNEKFKGKATLT-SDKSSSTAYMELSSLTSEDSAVYYCAYGPPYALDYW GQGTSVTV SS (SEQ ID NO: 14) and the light chain variable region comprises the sequence of (SEQ ID NO: 44)
QIVLTQSPAIMTASLGERVTMTCTASSSVSSSYLHWYQQKPGSSPKLWI

YSTSNLASGVPARFSGSGSGTSYSLTISSMEAEDAATYYCHQYHRSPYT

FGGGTKLEIK.

In an embodiment, the heavy light chain variable region comprises the sequence of EVQLQQSGAELVKP-GASVKLSCTASGFNIKDTYMHWVKQRPEQGLEWI-GRIDPANGNT QYGPKFQGKATITADTSSNTAY-LQLSSLTSEDTAVYYCARGGIFYYYGSSYSYAMDYW GQGTSVTVSS (SEQ ID NO: 43) and the light chain variable region comprises the sequence of (SEQ ID NO: 16)
DIQMTQTTSSLSASLGDRVTISCRASQDISNYLNWYQQKPDGTVTLLIY

YTSRLHSGVPSRFSGSGSGTDYSLTISNLEQEDIATYFCQQGNTLPRTF

GGGTKLEIK.

In an embodiment, the antibody is 3H7A9, 6D4B10, or 8A6F2.

Antibody 3H7A9 comprises the light chain variable region comprising the CDR sequences of RASQDISNYLN (SEQ ID NO: 10), YTSRLHS (SEQ ID NO: 11), and QQGNTLPRT (SEQ ID NO: 12), and the heavy chain variable region comprising the CDR sequences of DTYMH (SEQ ID NO: 37), YLNPYNDDTKYNEKFKG (SEQ ID NO: 38), and GGIFYYYGSSYSYAMDY (SEQ ID NO: 39). In an embodiment, antibody 3H7A9 comprises the light chain variable region comprising the sequence of DIQMTQTTSSLSASLGDRVTISCRASQDIS-NYLNWYQQKPDGTVTLLIYYTSRLHSGVPS RFSGSGSGTDYSLTISNLEQEDIATYFCQQGNTL-PRTFGGGTKLEIK (SEQ ID NO: 16) and the heavy light chain variable region comprising the sequence of (SEQ ID NO: 43)
EVQLQQSGAELVKPGASVKLSCTASGFNIKDTYMHWVKQRPEQGLEWIG

RIDPANGNTQYGPKFQGKATITADTSSNTAYLQLSSLTSEDTAVYYCAR

GGIFYYYGSSYSYAMDYWGQGTSVTVSS.

Antibody 6D4B10 comprises the light chain variable region comprising the CDR sequences of SYVMH (SEQ ID NO: 4), YLNPYNDDTKYNEKFKG (SEQ ID NO: 5), and GPPYALDY (SEQ ID NO: 6) and the heavy chain variable region comprising the CDR sequences of TASSSVSSSYLH (SEQ ID NO: 40), STSNLAS (SEQ ID NO: 41), and HQYHRSPYT (SEQ ID NO: 42). In an embodiment, antibody 6D4B10 comprises the heavy chain variable region comprising the sequence of EVQLQQSGPELVKP-GASVKMSCKASGYTFTSYVMHWVKQKPGQGLEWI-GYLNPYNDD TKYNEKFKGKATLT-SDKSSSTAYMELSSLTSEDSAVYYCAYGPPYALDYW GQGTSVTV SS (SEQ ID NO: 14) and the light chain variable region comprising the sequence of (SEQ ID NO: 44)
QIVLTQSPAIMTASLGERVTMTCTASSSVSSSYLHWYQQKPGSSPKLWI

YSTSNLASGVPARFSGSGSGTSYSLTISSMEAEDAATYYCHQYHRSPYT

FGGGTKLEIK.

Antibody 8A6F2 comprises the light chain variable region comprising the CDR sequences of SGYNWH (SEQ ID NO: 1), YIHYSGGTNYNPSLKS (SEQ ID NO: 2), and RTGTVPFAY (SEQ ID NO: 3) and the heavy chain variable region comprising the CDR sequences of SVSSSISSSNLH (SEQ ID NO: 7), GTSNLAS (SEQ ID NO: 8), QQWSSY-PLT (SEQ ID NO: 9). In an embodiment, antibody 8A6F2 comprises the heavy chain variable region comprising the sequence of DVQLQESGPDLVKP-SQSLSLTCTVTGYSITSGYNWHWIRQFPGN-KLEWMGYIHYSGGTN YNPSLKSRISITRDTSKNQF-FLQLNSVTTEDTATYYCARRTGTVPFAYWGQGTLV TVSA (SEQ ID NO: 13) and the light chain variable region comprises the amino acid sequence of (SEQ ID NO: 15)

EIVLTQSPALMAASPGEKVTITCSVSSSISSSNLHWYQQKSETSPKPWI

YGTSNLASGVPVRFSGSGSGTSYSLTISSMEAEDAATYYCQQWSSYPLT

FGGGTKLEIK.

In an additional embodiment, the antibody fragment includes an antigen-binding site/region from an antibody selected from the group consisting of 3H7A9, 6D4B10 or 8A6F2.

In an additional aspect, the description provides a hybridoma that expresses an antibody selected from the group consisting of 3H7A9, 6D4B10, 8A6F2, or a fragment thereof that includes an antigen-binding site/region from an antibody selected from the group consisting of 3H7A9, 6D4B10 or 8A6F2, respectively.

An antibody or antigen-binding fragment thereof that binds specifically to Dengue virus serotype 4 (DENV4), wherein the antibody is: 8A6F2 or the antigen-binding fragment comprises at least at least one heavy chain or light chain CDR amino acid sequence from an antigen-binding site/region of 8A6F2; 3H7A9 or the antigen-binding fragment comprises at least at least one heavy chain or light chain CDR amino acid sequence from an antigen-binding site/region of 3H7A9; or 6D4B10 or the antigen-binding fragment comprises at least at least one heavy chain or light chain CDR amino acid sequence from an antigen-binding site/region of 6D4B10. For example, the antigen-binding fragment may comprise the heavy chain variable region of 8A6F2 and/or the light chain variable region of 8A6F2.

An additional aspect of the present disclosure provides a pharmaceutical composition. The composition comprises the antibody (or an antigen-binding fragment thereof) of the present disclosure and a pharmaceutically acceptable carrier.

Another aspect of the present disclosure provides a method of diagnosing or detecting a DENV4 infection. The method comprises: contacting a sample from a patient with the antibody (or an antigen-binding fragment thereof) of present disclosure; detecting the binding of NS1, wherein detection of DENV4 NS1 is indicative of a patient that is positive for DENV4 infection. In certain embodiments, the antibody is a labeled antibody or detected by a labeled antibody. In certain embodiments, the method further includes the step of quantifying the binding of the antibody to NS1 of DENV4. In certain embodiments, the method further includes the step of diagnosing the patient as having or not having a DENV4 infection. In certain embodiments the method further includes the step of administering an effective amount of a treatment effective for ameliorating at least one symptom of DENV4 infection.

In some embodiments, contacting the blood sample comprises: contacting the blood sample to an immobilized antibody or an antigen-binding fragment thereof of the present disclosure; and contacting the antibody retained DENV4 virion with a second antibody or an antigen-binding fragment thereof of the present disclosure. In an embodiment, the immobilized antibody (or an antigen-binding fragment thereof) and the second antibody (or an antigen-binding fragment thereof) are different antibodies.

In other embodiments, the secondary antibody (or an antigen-binding fragment thereof) is linked to (e.g., chemically or covalent linked to) a detectable label. For example, the detectable label may be selected from the group consisting of an enzyme, biotin, streptavidin, a radioactive molecule, and/or an immunofluorescent protein or dye. In certain embodiments, when the detectable label is biotin or streptavidin, the method further comprises contacting a complex comprising a NS1 and the labeled antibody with a detection molecule that comprises streptavidin or biotin, respectively, linked to an immunofluorescent protein or dye or an enzyme.

In further embodiments, the antibody (or an antigen-binding fragment thereof) is linked to (e.g., chemically or covalent linked to) a detectable label and optionally a bead, particle, or nanoparticle. In an embodiment, the bead, particle, or nanoparticle is a magnetic bead.

In certain embodiments, the method further comprises separating a complex comprising NS1 and the labeled antibody (or an antigen-binding fragment thereof) via the bead, particle or nanoparticle for detecting the binding of NS1. In an embodiment, the sample comprises a blood or a tissue sample.

A further aspect of the present disclosure provides a method of treating a DENV4 infection in a subject. The method comprises: administering to a subject in the need thereof an effective amount of the antibody (or an antigen-binding fragment thereof) of the present disclosure or the pharmaceutical composition of the present disclosure, wherein the administering is effective at treating the infection.

In an embodiment, the antibody (or antigen-binding fragment thereof) is a humanized antibody or antigen-binding fragment thereof.

Other embodiments relate to a vector comprising the nucleic acid of the peptide of embodiments disclosed herein. Further embodiments relate to a host cell comprising the vector of embodiments disclosed herein.

Additional embodiments also relate to a cell (e.g., bacterial cells or eukaryotic cells, including hybridomas) expressing the antibody (or fragment thereof) of the present disclosure.

An additional aspect of the present disclosure provides a method of producing/making a DENV NS1 specific antibody or fragment thereof. The method comprises: providing a nucleic acid expressing DENV NS1 fusion protein with a solubility and stability tag; producing a multimeric DENV NS1 complex; and immunizing an animal with the multimeric DENV NS1 complex, wherein immunizing the animal produces an antibody specific to the DENV NS1. For example, the animal may be a chicken, a goat, a guinea pig, a hamster, a horse, a mouse, a rat, or a sheep. The multimeric DENV NS1 complex may comprise 2, 3, 4, 5, 6, or more DENV NS1 fusion proteins.

In some embodiments, the method further comprises preparing at least one hybridoma from spleen cells of the immunized animal. The hybridoma produces the DENV NS1 specific antibody.

In other embodiments, the method further comprises expressing the DENV NS1 specific antibody in a host cell. The host cell may comprise a nucleic acid that encodes the DENV NS1 specific antibody. The nucleic acid may be operably linked to a transcription regulatory sequence or control sequences. In some additional embodiment, the nucleic acid includes at least one sequence selected from the group consisting of SEQ ID NOS: 21-36. In another embodiment, the nucleic acid is comprised within an expression vector.

In additional embodiments, the solubility and stability tag includes a secretion signal.

In certain embodiments, the solubility and stability tag is a small ubiquitin-like modifier (SUMO) and/or the secretion signal is gp67.

In other particular embodiments, providing the nucleic acid expressing DENV NS1 fusion protein comprises inserting the Dengue virus NS1 into a vector comprising the solubility and stability tag and optionally, the secretion signal.

In an embodiment, the DENV NS1 is a DENV4 NS1.

In other embodiments, producing the multimeric DENV NS1 complex is performed with a eukaryotic expression system. For example, the eukaryotic expression system may be a baculovirus expression system or a vaccinia virus expression system. The producing a multimeric DENV NS1 complex may include a host cell comprising a vector that expresses a serotype specific DENV NS1 antibody. For example, the host cell can be a eukaryotic cell, such as a Chinese hamster ovary (CHO) cell, a NS0 murine myeloma cell, a human embryonic retinal cell, PER.C6® human cell (LONZA), an insect cell line, Sf9, or Sf21.

In further embodiment, producing a multimeric DENV NS1 complex comprises infecting eukaryotic cells with a baculovirus expressing the DENV NS1 fusion protein.

In some embodiments, the baculovirus expressing the DENV NS1 fusion protein is prepared by at least one of: transforming a bacteria (e.g., DH5α™ E. coli) with a vector (e.g., pl-secSUMO*) comprising the DENV NS1 fusion protein; selecting a vector-transformed bacteria; extracting/ purifying the vector from the vector-transformed bacteria; transforming a bacteria comprising a baculovirus shuttle vector (e.g., DH10BAC™ E. coli); selecting a bacteria with a recombinant DENV NS1 fusion protein-baculovirus vector; extracting/purifying the recombinant DENV NS1 fusion protein-baculovirus vector; transfecting a eukaryotic cell (e.g. a mammalian cell, or insect cell, e.g., Sf9 or Sf21) with the recombinant DENV NS1 fusion protein-baculovirus vector; or collecting cell culture supernatant comprising the baculovirus expressing the DENV NS1 fusion protein.

In other embodiments, immunizing the animal with the multimeric DENV NS1 complex includes at least one of: administering the multimeric DENV NS1 complex to the animal at least two times (e.g., 1, 2, 3, 4, 5, 6, 7, 8, 9, or 10 administrations); isolate at least one primed spleen cell from the animals; fusing the primed spleen cell with a myeloma cell (e.g., a mouse myeloma cell or a rat myeloma cell); or selecting a hybridoma cell expressing the antibody specific to the DENV NS1.

In a particular embodiment, the method further comprises humanizing the antibody specific for DENV NS1.

In another embodiment, the method further comprises treating the antibody specific for DENV NS1 thereby producing a fragment thereof. In an embodiment, treating comprises contacting the antibody specific for DENV NS1 with an agent selected from the group consisting of (i) pepsin, (ii) papain, and (iii) pepsin and β-mercaptoethanol.

Other embodiments relate to a vector comprising the nucleic acid of the polypeptide of the present disclosure. Further embodiments relate to a host cell comprising the vector of the present disclosure. For example, the nucleic acid of the polypeptide (which can be included in a in a host cell for expression) can include a heavy chain variable region sequence selected from the group consisting of: GATGTGCAGCTTCAG-GAGTCAGGACCTGACCTGGTGAAACCTTCTCAGT-CACTTTCA CTCACCTGCACTGTCACTGGCTACTC-CATCACCAGTGGTTATAACTGGCACTGGATC CGGCAGTTTCCAGGAAACAAACTGGAATG-GATGGGCTACATACACTACAGTGGTGG CACTAAC-TACAACCCATCTCTCAAAAGTCGAATCTCTAT-CACTCGAGACACATCCAA GAACCAGTTCTTCCTGCAGTTGAATTCTGTGAC-TACTGAGGACACAGCCACATATTA CTGTGCAAGAAGGACTGGGACGGTCCCGTTTGCT-TACTGGGGCCAAGGGACTCTGGT CACTGTCTCTGCA (SEQ ID NO: 21) and GAGGTCCAGCTGCAGCAGTCTGGACCT-GAGCTGGTAAAGCCTGGGGCTTCAGTGAA GATGTCCTGCAAGGCTTCTGGATACACATT-CACTAGCTATGTTATGCACTGGGTGAA GCAGAAGCCTGGGCAGGGCCTTGAGTGGATTGGA-TATCTTAATCCTTACAATGATGA TACTAAGTACAAT-GAGAAGTTCAAAGGCAAGGCCACACTGACTTCA-GACAAATCCT CCAGCACAGCCTACATG-GAGCTCAGCAGCCTGACCTCT-GAGGACTCTGCGGTCTATT ACTGTGCC-TACGGCCCTCCCTATGCTTTGGACTACTGGGGTCA AGGAACCTCAGTCA CCGTCTCCTCA (SEQ ID NO: 22), which results in amino acid sequences SEQ ID NOS: 13 and 14.

In other embodiments, the nucleic acid of the polypeptide can include a light chain variable region sequence selected from the group consisting of GAAATTGTGCT-CACCCAGTCTCCAGCACTCATGGCTG-CATCTCCAGGGGAGAAGGTC ACCAT-CACCTGCAGTGTCAGCTCAAGTATAAGTTCCAGCA ACTTGCACTGGTACCAG CAGAAGTCAGAAACCTCCCCCAAACCCTGGATT-TATGGCACATCCAACCTGGCTTCT GGAGTCCCTGTTCGCTTCAGTGGCAGTG-GATCTGGGACCTCTTATTCTCTCACAATCA GCAGTATGGAGGCTGAAGATGCTGCCACTTAT-TACTGTCAACAGTGGAGTAGTTACC CACT-CACGTTCGGAGGGGGGACCAAGCTGGAAATAAAA (SEQ ID NO: 23) and GATATCCAGATGACACAGACTA-CATCCTCCCTGTCTGCCTCTCTGGGAGACAGAGTC ACCATCAGTTGCAGGGCAAGTCAGGACATT-AGCAATTATTTAAACTGGTATCAGCAG AAACCA-GATGGAACTGTTACACTCCTGATCTACTACACAT-CAAGATTACACTCAGGA GTCCCATCAAGGTTCAGTGGCAGTGGGTCTG-AACAGATTATTCTCTCACCATTAGC AACCTG-GAGCAAGAAGATATTGCCACTTACTTTTGC-CAACAGGGTAATACGCTTCCT CGGACGTTCGGTGGAGGCACCAAGCTGGAAAT-CAAA (SEQ ID NO: 24), which results in amino acid sequences SEQ ID NOS: 15 and 16.

In another embodiment, the nucleic acid of the polypeptide includes a heavy chain variable region selected from the group consisting of AGTGGTTATAACTGGCAC (SEQ ID NO: 25), TACATACACTACAGTGGTGGCACTAACTA-CAACCCATCTCTCAAAAGT (SEQ ID NO: 26), AGGACTGGGACGGTCCCGTTTGCTTAC (SEQ ID NO: 27), GGCCCTCCCTATGCTTTGGACTAC (SEQ ID NO: 28), TATCTTAATCCTTACAATGATGATACTAAGTA-CAATGAGAAGTTCAAAGGC (SEQ ID NO: 29), and AGCTATGTTATGCAC (SEQ ID NO: 30). In other embodiments, the nucleic acid of the polypeptide includes a light chain variable region selected from the group consisting of AGTGTCAGCT-CAAGTATAAGTTCCAGCAACTTGCAC (SEQ ID NO: 31), GGCACATCCAACCTGGCTTCT (SEQ ID NO: 32), CAACAGTGGAGTAGTTACCCACTCACG (SEQ ID NO: 33), AGGGCAAGTCAGGACATTAGCAATTATTTAAAC (SEQ ID NO: 34), CAACAGGGTAATACGCTTCCTCGGACG (SEQ ID NO: 35), and TACACATCAAGATTACACTCA (SEQ ID NO: 36).

Additional embodiments also relate to a cell (e.g., bacterial cells or eukaryotic cells, including hybridomas) expressing the antibody (or fragment thereof) of the present disclosure.

Production of Antibodies

A description follows as to exemplary techniques for the production of the antibodies used in accordance with embodiments disclosed herein.

(i) Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 µg or 5 µg of the protein or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(ii) Monoclonal Antibodies

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

For example, the monoclonal antibodies may be made using the hybridoma method first described by Kohler and Milstein 1975 *Nature* 256:495, or may be made by recombinant DNA methods.

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59 103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are SP-2, SP 2/0, or X63-Ag8-653 cells available from the American Type Culture Collection, Manassas, VA USA. Human myeloma and mouse-human heteromyeloma cell lines also have been described for the production of human monoclonal antibodies (Brodeur et al., Monoclonal Antibody Production Techniques and Applications, pp. 51 63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA). The binding affinity of the monoclonal antibody can, for example, be determined by the Scatchard analysis of Munson et al., Anal. Biochem., 107: 220 (1980).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional antibody purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells.

The DNA also may be modified, for example, by substituting the coding sequence for human heavy chain and light chain constant domains in place of the homologous murine sequences, or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

(iii) Humanized Antibodies

Methods for humanizing non-human antibodies have been described in the art. Preferably, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al., Nature, 321:522 525 (1986)), by substituting hypervariable region sequences for the corresponding sequences of a human antibody. Accordingly, such "humanized" antibodies are chimeric antibodies wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence that is closest to that of the rodent is then accepted as the human framework region (FR) for the humanized antibody. Another method uses a particular framework region derived from the consensus sequence of all human antibodies of a particular subgroup of light or heavy chains. The same framework may be used for several different humanized antibodies.

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

The present application also contemplates affinity matured antibodies, which antibodies bind antigen. The parent antibody may be a human antibody or a humanized antibody. The affinity matured antibody preferably binds to antigen with an affinity superior to that of the parent antibody.

Various forms of the humanized or affinity matured antibody are contemplated. For example, the humanized or affinity matured antibody may be an antibody fragment. Alternatively, the humanized or affinity matured antibody may be an intact antibody, such as an intact IgG1 or IgG2b antibody.

(iv) Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production.

For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge.

As discussed above, human antibodies may also be generated by in vitro activated B cells.

(v) Antibody Fragments

Various techniques have been developed for the production of antibody fragments. Traditionally, these fragments were derived via proteolytic digestion of intact antibodies. However, these fragments can now be produced directly by recombinant host cells. For example, the antibody fragments can be isolated from the antibody phage libraries discussed above.

(vi) Bispecific Antibodies

Bispecific antibodies are antibodies that have binding specificities for at least two different epitopes. Methods for making bispecific antibodies are known in the art. Traditional production of full length bispecific antibodies is based on the coexpression of two immunoglobulin heavy chain-light chain pairs, where the two chains have different specificities. Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low.

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, $C_H2$, and $C_H3$ regions. It is preferred to have the first heavy-chain constant region ($C_H1$) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation.

According to another approach, the interface between a pair of antibody molecules can be engineered to maximize the percentage of heterodimers that are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells. Heteroconjugate antibodies may be made using any convenient cross-linking methods. Suitable cross-linking agents are well known in the art, along with a number of cross-linking techniques.

Antibodies with more than two valencies are contemplated. For example, trispecific antibodies can be prepared.

(vii) Other Amino Acid Sequence Modifications

Amino acid sequence modification(s) of the antibodies described herein are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid changes also may alter post-translational processes of the antibody, such as changing the number or position of glycosylation sites.

A useful method for identification of certain residues or regions of the antibody that are preferred locations for mutagenesis is called "alanine scanning mutagenesis". Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody a polypeptide that increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in Table 1 under the heading of "preferred substitutions". If such substitutions result in a change in biological activity, then more substantial changes, denominated "exemplary substitutions" in Table 1, or as further described below in reference to amino acid classes, may be introduced and the products screened.

TABLE 1

| Amino Acid Substitutions | | |
| --- | --- | --- |
| Original Residue | Exemplary Substitutions | Preferred Substitutions |
| Ala (A) | Val, Leu, Ile | Val |
| Arg (R) | Lys, Gln, Asn | Lys |
| Asn (N) | Gln, His, Asp, Lys, Arg | Gln |
| Asp (D) | Glu, Asn | Glu |
| Cys (C) | Ser, Ala | Ser |
| Gln (Q) | Asn, Glu | Asn |
| Glu (E) | Asp, Gln | Asp |
| Gly (G) | Ala | Ala |
| His (H) | Asn, Gln, Lys, Arg | Arg |
| Ile (I) | Leu, Val, Met, Ala, Phe, norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala, Tyr | Tyr |
| Pro (P) | Ala | Ala |
| Ser (S) | Thr | Thr |
| Thr (T) | Ser | Ser |
| Trp (W) | Tyr, Phe | Tyr |
| Tyr (Y) | Trp, Phe, Thr, Ser | Phe |
| Val (V) | Ile, Leu, Met, Phe, Ala, norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

hydrophobic: norleucine, met, ala, val, leu, ile;

neutral hydrophilic: cys, ser, thr;

acidic: asp, glu;

basic: asn, gln, his, lys, arg;

residues that influence chain orientation: gly, pro; and aromatic: trp, tyr, phe.

Non-conservative substitutions will entail exchanging a member of one of these classes for another class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

To increase the serum half-life of the antibody, one may incorporate a salvage receptor binding epitope into the antibody. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule. The next section describes approaches to design and generate immunoadhesins.

Pharmaceutical Formulations

Prophylactic or therapeutic formulations of the antibodies used in accordance with embodiments disclosed herein are prepared for storage by mixing an antibody having the desired degree of purity with optional pharmaceutically acceptable carriers, excipients or stabilizers (Remington's Pharmaceutical Sciences, 18$^{th}$ ed., 1990, Mack Publishing Co., Easton, PA), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorchinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being prevented or treated, preferably those with complementary activities that do not adversely affect each other. For example, it may be desirable to further provide antibodies that bind to other targets (e.g., an antibody that binds a different epitope). Alternatively, or additionally, the composition may further comprise antiviral agent(s) or pain reliever(s), such as analgesics. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin micropheres, microemulsions, nano-particles and nanocapsules) or in macroemulsions. Such techniques are disclosed in Remington's Pharmaceutical Sciences, 18th ed., 1990, Mack Publishing Co., Easton, PA.

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinyl-alcohol)), polylactides, copolymers of L-glutamic acid and γ ethyl-L-glutamate, non-degradable ethylene-vinyl acetate, degradable lactic acid-glycolic acid copolymers such as the LUPRON DEPOT™ (injectable micropheres composed of lactic acid-glycolic acid copolymer and leuprolide acetate), and poly-D-(–)-3-hydroxybutyric acid. The formulations to be used for in vivo administration must be sterile. This is readily accomplished by filtration through sterile filtration membranes. The following section describes alternative, non-therapeutic uses for the polypeptide of embodiments disclosed herein.

Non-Therapeutic Uses for the Polypeptide

The polypeptide may be useful in diagnostic assays, e.g., for detecting expression of an antigen of interest in specific cells, tissues, or serum. For diagnostic applications, the polypeptide typically will be labeled with a detectable moiety. Radioisotopes, such as $^{35}$S, $^{14}$C, $^{125}$I, $^{3}$H, and $^{131}$I are available. The polypeptide can be labeled with the radioisotope using the techniques described in Current Protocols in Immunology, Volumes 1 and 2, Coligen et al., Ed. Wiley-Interscience, New York, N.Y., 1991, for example, and radioactivity can be measured using scintillation counting. Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the polypeptide using the techniques disclosed in Current Protocols in Immunology, supra, for example. Fluorescence can be quantified using a fluorimeter. In addition, various enzyme-substrate labels are available. The enzyme generally catalyzes a chemical alteration of the chromogenic substrate that can be measured using various techniques. For example, the enzyme may catalyze a color change in a substrate, which can be measured spectrophotometrically. Alternatively, the enzyme may alter the fluorescence or chemiluminescence of the substrate. The chemiluminescent substrate becomes electronically excited by a chemical reaction and may then emit light that can be measured (using a chemiluminometer, for example) or donates energy to a fluorescent acceptor. Examples of enzymatic labels include luciferases (e.g., firefly luciferase and bacterial luciferase, luciferin, 2,3-dihydrophthalazinediones, malate dehydrogenase, urease, peroxidase such as horseradish peroxidase (HRPO), alkaline phosphatase, [ß-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like.

Sometimes, the label is indirectly conjugated with the polypeptide. The skilled artisan will be aware of various techniques for achieving this. For example, the polypeptide can be conjugated with biotin and any of the three broad categories of labels mentioned above can be conjugated with avidin, or vice versa. Biotin binds selectively to avidin and thus, the label can be conjugated with the polypeptide in this indirect manner. Alternatively, to achieve indirect conjugation of the label with the polypeptide, the polypeptide is conjugated with a small hapten (e.g., digoxigenin) and one of the different types of labels mentioned above is conjugated with an anti-hapten polypeptide (e.g., anti-digoxigenin antibody). Thus, indirect conjugation of the label with the polypeptide can be achieved. In another embodiment, the polypeptide need not be labeled, and the presence thereof can be detected using a labeled antibody that binds to the polypeptide.

The polypeptide of embodiments disclosed herein may be employed in any known assay method, such as competitive binding assays, direct and indirect sandwich assays (e.g., ELISA), immunoprecipitation assays, immunohistochemistry, and/or flow cytometry. The polypeptide may also be used for in vivo diagnostic assays. Generally, the polypeptide is labeled with a radionuclide (such as $^{111}$In, $^{99}$Tc, $^{14}$C, $^{131}$I, $^{125}$I, $^{3}$H, $^{32}$P or $^{35}$S) so that the antigen or cells expressing it can be localized using immunoscintiography.

In Vivo Uses for the Polypeptide

It is contemplated that the polypeptide of embodiments disclosed herein may be used for the prophylaxis or treatment of a mammal, e.g. a patient suffering from, or predisposed to, a disease or disorder that could benefit from administration of the polypeptide of the present disclosure.

The polypeptide of the present disclosure can be administered by any suitable means, including parenteral, subcutaneous, intraperitoneal, intrapulmonary, and intranasal. Parenteral infusions include intramuscular, intravenous, intraarterial, intraperitoneal, or subcutaneous administration. In addition, the polypeptide is suitably administered by pulse infusion, particularly with declining doses of the polypeptide. Preferably the dosing is given by injections, most preferably intravenous or subcutaneous injections, depending in part on whether the administration is brief or chronic.

For the prevention or treatment of disease, the appropriate dosage of the polypeptide of the present disclosure will depend on the type of disease to be prevented or treated, the severity and course of the disease, whether the polypeptide of the present disclosure is administered for preventive or therapeutic purposes, previous prophylaxis and therapy, the patient's clinical history and response to the polypeptide of the present disclosure, and the discretion of the attending physician. The polypeptide of the present disclosure is suitably administered to the patient at one time or over a series of treatments.

For passive immunization with an antibody, about 1 μg/kg to 15 mg/kg (e.g., 0.1 20 mg/kg) of the polypeptide of the present disclosure is an initial candidate dosage for administration to the patient, whether, for example, by one or more separate administrations, or by continuous infusion. A typical daily dosage might range from about 1 μg/kg to 100 mg/kg or more, depending on the factors mentioned above. For repeated administrations over several days or longer, depending on the condition, the prophylaxis or treatment is sustained until a desired suppression or modification of disease symptoms occurs. However, other dosage regimens may be useful. The progress of this therapy is easily monitored by conventional techniques and assays.

The composition comprising a polypeptide of the present disclosure will be formulated, dosed, and administered in a fashion consistent with good medical practice. Factors for consideration in this context include the particular disorder being prevented or treated, the particular mammal being treated, the clinical condition of the individual patient, the cause of the disorder, the site of delivery of the agent, the method of administration, the scheduling of administration, and other factors known to medical practitioners. The "prophylactically or therapeutically effective amount" of the polypeptide to be administered will be governed by such considerations, and is the minimum amount necessary to prevent, ameliorate, or treat a disease or disorder. The polypeptide of the present disclosure need not be, but is optionally formulated with one or more agents currently used to prevent or treat the disease in question. The effective amount of such other agents depends on the amount of polypeptide present in the formulation, the type of disorder or treatment, and other factors discussed above. These are generally used in the same dosages and with administration routes as used hereinbefore or about from 1 to 99% of the heretofore employed dosages.

The following examples provide illustrations of some of the embodiments described herein but are not intended to limit invention.

EXAMPLES

Materials and Methods of the Examples

Preparation of NS1 Antigen from DENV-Infected Vero Cells. DENV infected Vero cell culture supernatant was produced from each of the four DENV serotypes was produced as previously described (Gelanew, Poole-Smith, and Hunsperger 2015) with a slight modification. Briefly, Vero cells (ATCC®, Manassas, Virginia, USA) were infected at a multiplicity of infection (MOI)=0.1 and grown in M199 medium (GIBCO®/Life Technologies, Grand Island, New York, USA) supplemented with 5% super low IgG FBS (INVITROGEN™, Carlsbad, CA, USA) and 1% gentamicin (GIBCO®, Grand Island, New York, USA), 1% penicillin-streptomycin (GIBCO®, Grand Island, New York, USA), 3% sodium bicarbonate (GIBCO®, Grand Island, New York, USA). In order to avoid cell lysis, and thereby the release of proteolytic enzymes into the culture medium, DENV-infected Vero cells were monitored every day for cytopathic effect (CPE), and culture supernatants were harvested and filtered on day 3 or 4 post infection at approximately 50% CPE. The same procedure was followed for control antigen from mock-infected Vero cells. Culture medium was concentrated (about 3×) by using AMICON®, CENTRICON®-30K (Millipore, Billerica, Massachusetts, USA) and treated with SIGMAFAST™ protease inhibitor cocktail (SIGMA-ALDRICH®, St. Louis, MO, USA). The presence of secreted native NS1 in these culture supernatants was confirmed using a serotype-cross-reactive Dengue Early NS1 ELISA (PANBIO® Diagnostics, Brisbane, Australia). Thereafter, these culture supernatants were stored at −80° C. until use.

Cloning DENV4 NS1 into pl-secSUMO* Vector. Total viral RNA was isolated from viral seeds of DENV4 (H421, a prototype strain) infected C6/36 cells (*Aedes albopictus* cell line, ATCC®) using the QIAAMP® Viral RNA Mini kit (QIAGEN®, Gaithersburg, MD, USA), and a complimentary DNA (cDNA) of DENV4 NS1 gene was reverse transcribed using SUPER SCRIPT™ III one step reverse transcriptase polymerase chain reaction (RT PCR) kit (INVITROGEN™, Carlsbad, CA, USA) and paired primers (forward: 5'-

ATACGTCTCTAGGTGACACGGGTTGTGCGGTG-3'; SEQ ID NO: 17) and (reverse; 5'-

GCGTCTAGATTAGGCCGATACCTGTGATTT-3; SEQ ID NO: 18), according to manufacturer's instructions. These primers were designed to introduce restriction sites for BmsBI and XbaI in order to clone the full length of DENV4 NS1 gene into a directional pl-secSUMO* cloning vector (LifeSensors, Malvern, PA). Prior to primer design, the complete absence of BmsBI and XbaI restriction sites in the full-length of DENV4 NS1 gene sequence was confirmed using a NEBcutter V2.0 (nc2.neb.com/NEBcutter2/).

The underlined nucleotide sequences in the forward and reverse primers represent the actual first codons, and the complementary sequence to the last codons of the DENV4 NS1 gene, respectively. At the 5' end of the forward primer, ATA was added to enhance the efficacy of BmsBI digestions of the PCR product. The sequence CGTCTCT was added as a BmsBI restriction cleavage site for the insertion of NS1 into the multiple cloning sites of the pl-secSUMO* vector, and GGT represented the last codon of the SUMO* tag. In the 5' end of the reverse primer, GCG was added to enhance the efficacy of XbaI restriction digest of the PCR product end, TCTAGA was added to serve as an XbaI restriction cleavage site for the insertion of NS1 into the multiple cloning site of the pl-secSUMO* vector, and TTA represented a reverse complement of a stop codon.

The generated amplicons were visualized by gel electrophoresis with 1% low melting point agarose (LMPA; INVITROGEN™, Calsbad, CA, USA), and the appropriated band was excised, and purified using a QIAQUICK® Gel Extraction Kit (QIAGEN®, Gaithersburg, MD, USA) and double restriction enzyme digested with BmsBI and XbaI (New England BIOLABS® Ipswich, Massachusetts, USA). Since the optimal temperatures and buffers for these two restriction enzymes are different, a two-step restrictions digest was performed. First, amplicons were digested with XbaI at 37° C. for 1 hour, the solution was then centrifuged at 10,000×g for 30 minutes, and the supernatant discarded. The DNA pellet obtained was washed twice with an ice cold 70% ethanol, air dried, and re-suspended in Milli-Q® water. The re-suspended DNA pellet was digested with BsmBI for 1 hour at 55° C. Then pl-secSUMO* plasmids were linearized with BsmBI in order to generate two overhang ends which are complementary to the double-digested PCR product ends. Both the double-digested PCR products and linearized plasmids were then visualized on a 2% LMPA gel. The appropriate bands were excised, purified as described above, and ligated overnight at 16° C. using T4 DNA Ligase (INVITROGEN™, Calsbad, California, USA) with a 3:1 ratio of double-restricted amplicons (NS1 gene) to linearized pl-secSUMO* plasmids. The ligated solution was then immediately transformed into chemically competent DH5a *E. coli* cells (INVITROGEN™, Calsbad, CA, USA) per the transformation protocol described in Panavas et al. (2009). Positive DH5a *E. coli* clones with recombinant SUMO*-NS1 gene were then selected by colony PCR using forward primer polH (described below) and the reverse primer described above. Additionally, to verify the integrity of the NS1 gene, recombinant plasmid DNAs isolated from PCR-positive clones using QIAPREP® Skin Miniprep Kit (QIAGEN®, Gaithersburg, Maryland, USA) were sequenced in both directions using two external primers (polH, 5'-GGAT-TATTCATACCGTCCCACCAT-3' (SEQ ID NO: 19) and Tn7, 5'-CTGGGTGTA GCGTCGTAAGCTAATAC-3' (SEQ ID NO: 20)). Plasmid DNAs with SUMO*-NS1 fusion constructs were then transformed into chemically competent DH10bac *E. coli* cells (INVITROGEN™, Calsbad, CA, USA) according to the transformation protocol described in Panavas et al. (2009). Positive clones were selected by blue and white screening assay followed by colony PCR. Then Bacmid DNA was isolated from positive clones using QIAprep® Spin Miniprep Kit (QIAGEN®, Gaithersburg, MD, USA), and sequenced for integrity in both direction using primer pair polH and Tn7. The isolated Bacmid DNAs were stored at 4° C. until use.

Expression of SUMO*-DENV4 NS1 Fusion Protein in Sf21 Cells. SUMO*-NS1 fusion protein was expressed in *Spodoptera frugiperda* (Sf) 21 cells (INVITROGEN™, Calsbad, CA, USA). Briefly, Sf21 cells were transfected using 3 μg of bacmid DNA for high titer viral stock production, which was later used to infect of these cells at an MOI=1. Because pl-secSUMO* plasmid contain an upstream gp67 secretion signal of the SUMO* fusion which could result in secretion of the SUMO*-rNS1 into the cell culture medium (FIG. 1), only culture supernatant of Sf21 cells was harvested on day 3 post infection. The culture supernatants (containing soluble SUMO*-NS1 fusion protein) was concentrated (5×) and then purified by immobilized metal affinity chromatography (IMAC) under native conditions. The purity, as well as the molecular size, of the fusion protein was determined by Coomassie blue stained 12% SDS-PAGE gel (INVITROGEN™, Calsbad, California, USA) under both reducing and non-reducing conditions, and confirmed by western blot assay. Proper folding of the SUMO* tagged DENV-4 rNS1 protein was confirmed by commercial serotype cross-reactive Dengue Early (PANBIO® Diagnostics, Brisbane, Australia), which comprises MAbs reactive to the native hexameric NS1 in serum samples of dengue patients.

Western blot analysis. Fused protein of SUMO*-DENV-4 NS1 and unfused DENV4 rNS1 protein at concentrations of 2 μg or 100 ng were separated using NUPAGE® NOVEX™12% SDS-PAGE gel (Life Technologies™ Corporation, Carlsbad, CA, USA) under non-reduced, heat-denatured or non-denatured conditions. Protein size discrimination was determined with Molecular Weight (MW) Standards (116, 66, 45, 31, and 21 kDa) and MAGIC-MARK™ XP Protein standards (20-220 kDa, Invitrogen™, Calsbad, California, USA). For western blot analysis the proteins were transferred to 0.22 μm nitrocellulose membranes (Invitrogen™, Calsbad, California, USA), blocked overnight at room temperature (RT) in 5% NFDM in phosphate buffered saline (PBS) with 0.05% Tween20 (NFDM-PBST). For SUMO*-DENV-4 NS1 protein analysis by western blot, the membrane was incubated with anti-HisTag. For the characterization of MAbs elicited for SUMO*-DENC4-NS1, the nitrocellulose membranes were incubated with the primary MAbs that were produced against the fusion protein. Following the incubation with primary antibody (i.e., the generated MAbs), a secondary anti-mouse peroxidase detector antibody diluted at 1:10,000 (KPL, Gaithersburg, Maryland, USA) was used. The substrate SUPERSIGNAL™ West Pico solution (PIERCE™/THERMO SCIENTIFIC™, Rockford, IL, USA) was used to detect proteins.

Mice Immunization and Isolation of Anti-DENV4 NS1 MAbs Secreting Hybridoma Clones. The immunization and production of hybridoma clones were performed by Custom Antibody Generation Services (Celtein Biosciences, LLC; Monroe, Ohio, USA) using our SUMO*-DENV4 NS1 fusion protein. To produce anti-NS1 MAb-secreting hybridoma clones, female BALB/c mice (6-8 weeks) were immunized with purified soluble SUMO*-DENV4 NS1 fusion protein in complete Freud's adjuvant followed by four boosts with incomplete Freund's adjuvant with 14 day intervals between boosts. Four days after the last boost, primed spleen cells were isolated aseptically from mice with the highest titer against SUMO*-DENV4 NS1 fusion protein and unfused DENV4 rNS1 (expressed in mammalian cells). These primed spleen cells were then fused with SP2/0 cells as previously described (Kohler and Milstein, 1975). To select desired MAb secreting hybridomas, culture supernatant from each clone was evaluated by iELISA using both SUMO*-DENV4 NS1 fusion protein and unfused DEN4 rNS1 protein and fixed cell based ELISA as described previously in Gelanew et al. (2015). Further, the hybridoma culture supernatants were also screened against recombinant SUMO protein by iELISA.

MAb Production, Purification, and Characterization. MAb production from positive hybridoma clones (3H7A9, 6D4B10, and 8A6F2) was carried out using a CELLINE™ 1000 System bioreactor (BD™ Biosciences; Sparks, MD, USA) according to the manufacturer's instructions and as per protocols described in Gelanew et al. (2015). Purification MAb was done using VIVAPURE® MAXIPREP Protein G Spin Columns (Satorius™ Stedim, Bohemia, NY, USA) per the manufacturer's instructions. MAbs were characterized using fixed cell ELISA and iELISA as previously described (Gelanew, Poole-Smith, and Hunsperger 2015).

MAbs isotypes were determined using a Mouse MAbs Isotyping kit (Pierce™/Thermo Scientific™, Rockford, IL, USA) according to the manufacturer's instructions. Purified and dialyzed MAbs were biotinylated with a spacer arm biotin (NHS-PEG$_4$-Biotin) using EZ-LINK™ NHS-PEG4-Biotinylation Kit (PIERCE™/THERMO SCIENTIFIC™, Rockford, IL, USA).

Epitope Mapping by Competition ELISA. In order to determine whether the MAbs recognize the same epitope or distinct epitopes on the DENV4 NS1, a competition ELISA was performed as described in Gelanew et al. (2015).

Sequencing the Antigen Binding Sites of MAbs. Sequencing the antigen binding sites (the variable regions of light ($V_L$) and heavy ($V_H$) chains) of the three MAbs were performed by customer service (GenScript, NJ, USA) in order to determine the identity of the MAbs. Five single colonies with the correct variable light chain and heavy chain genes of each hybridoma clones was sequenced. After performing a multiple sequence alignment of the five peptide sequences using ClustalW2 (ebi.ac.uk), a consensus sequence for both the $V_L$ and the $V_H$ of each hybridoma clone was obtained. Finally, multiple alignments were performed among $V_L$ consensus sequences and $V_H$ consensus sequences to determine the identity of binding region of the three complementarity determining regions (CDR1, CDR2, and CDR3) of MAbs.

Development of DENV4 Specific NS1 Capture ELISA. NS1 capture ELISAs were developed by utilizing two of the best MAbs as a capture and a detector antibodies. In order to determine the optimal capture/detector pair for the detection of DENV4 NS1 antigen, each MAbs was tested either as a capture or a detector antibody. The optimal concentrations of capture and detector antibodies were determined by checkerboard titration ELISA. Microtiter plates were coated with MAb 8A6F2 (100 µl/well) diluted in bicarbonate buffer (pH 9.6) at a concentration of 10 µg/mL and incubated overnight at 4° C. The next day, excess unbound capture MAb was removed, and thereafter, the microtiter plates were blocked with 200 µl/well of 5% NFDM or 2% bovine serum albumin (BSA) (w/v). After a 45 minute incubation, the microtiter plates were washed 3× with PBST. Thereafter, 100 µl/ml of rNS1 antigen (0.5 µg/ml) and serum sample diluted 1:1 in PBST was added and incubated at 37° C. for 60 minutes. Following the incubation and three washes with PBST, 100 µl/well of biotinylated MAb 6D4B10 diluted at 1:2000 in PBST was added and incubated for 1 hour at 37° C. After 3 washes with PBST, 100 µl/well of peroxidase-conjugated streptavidin was added. The microtiter plates were then incubated at 37° C. for 30-60 minutes. After 5 washes with PBST, the reaction was visualized by adding 100 µl/well of 3,3',5,5'-Tetramethylbenzidine (TMB) liquid substrate and incubating at RT in the dark for 15 minutes. The reaction was then stopped with 100 µl/well of TBM stop solution. The optical density (OD) was measured at 450 nm on ELISA ELx800™ microplate reader (BioTek®, Vermont, USA). Each sample was tested in triplicate.

Testing Culture Supernatants from DENV1-4 Infected Vero Cells and rNS1 of Flaviviruses. The serotype-specificity of the above described NS1 capture ELISA was examined using culture supernatants obtained from DENV-infected Vero cells and commercially available rNS1 of Flaviviruses, including all four DENV serotypes and expressed in mammalian cell line (NativeAntigen, Oxfordshire, UK). The presence of NS1 in the culture supernatants was pre-confirmed using Dengue Early (PANBIO® Diagnostics, Brisbane, Australia).

Figure 2:
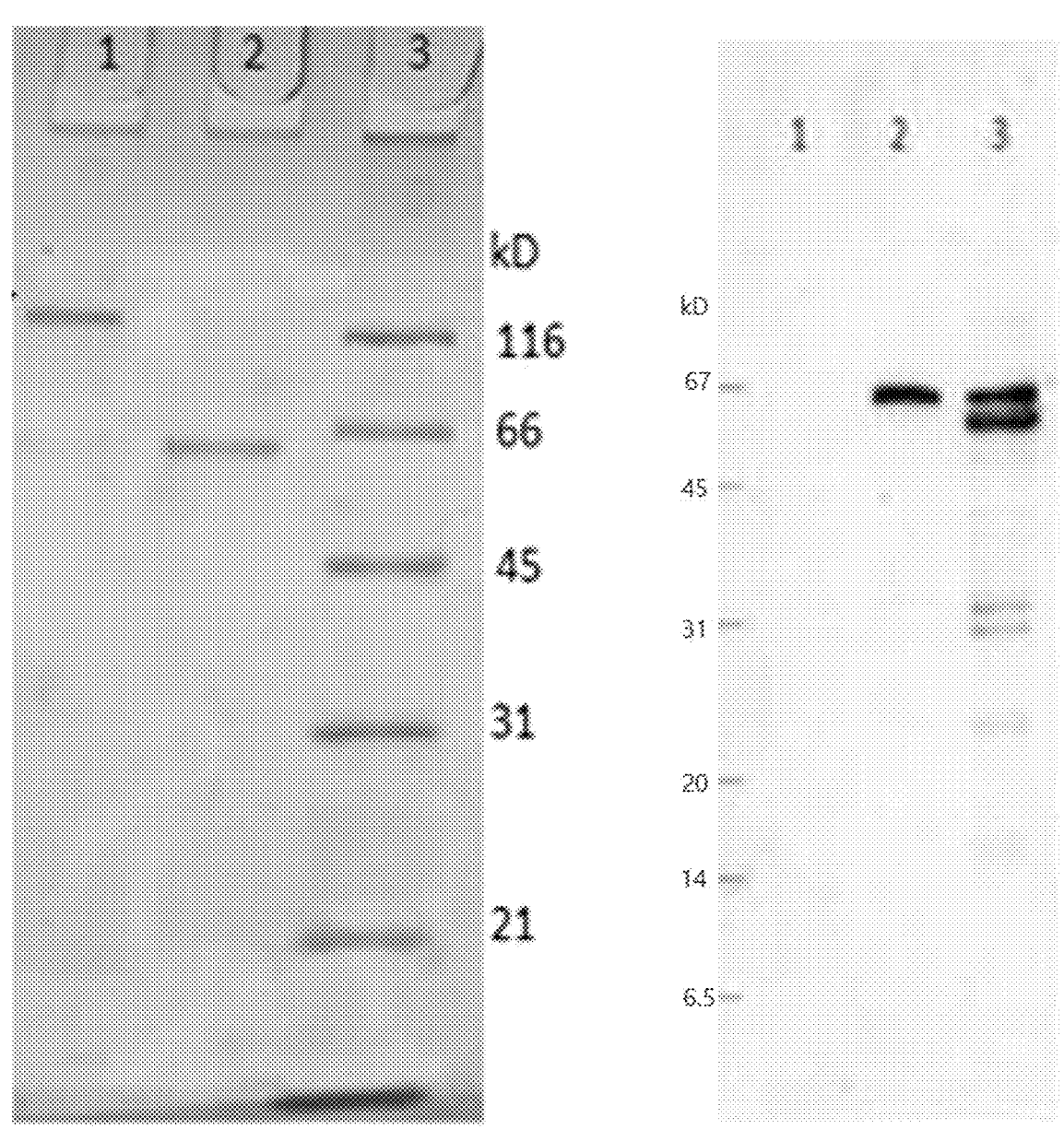
FIGS. 2A and 2B. SUMO*-NS1 fusion protein expression analysis in Coomassie-blue stained 12% SDS-PAGE gel is shown in FIG. 2A. Lane 1: SUMO-NS1 under non-reducing conditions; Lane 2: SUMO-NS1 under reducing conditions; and Lane 3: MW of markers in kDa. Western blot of SUMO*-DENV4 NS1 protein using anti-his antibody is shown in FIG. 2B. Lane1: Molecular Marker; Lane2: secreted NS1; Lane 3: cell lysate of solubilized of SUMO*-DENV4 NS1

SUMO*-DENV4 NS1 Fusion Protein Expressed was the Correct Conformation of DENV NS1. Affinity purified SUMO*-DENV4 NS1 fusion protein expressed in Sf21 cells appeared as a monomer (approximately 62 kDa) and a dimer (approximately 120 kDa) on reduced and non-reduced 12% SDS-PAGE, respectively (FIG. 2A). The expected sizes of monomeric and dimeric native DENV4 NS1 expressed in mammalian cells are 48 kDa and 80 kDa, respectively (Flamand et al. 1999). Considering the molecular weight of the SUMO* tag, which is about 11.5 kDa, the observed sizes on SDS-PAGE matched the expected sizes of monomeric and dimeric DENV4 NS1, respectively. Also, the appearance of a single band on SDS-PAGE (FIG. 2B) confirmed the purity of the SUMO*-NS1 fusion protein. The correct conformation of the expressed and purified protein was confirmed by commercial cross-serotype reactive Dengue Early NS1 capture ELISA (Panbio® Diagnostics, Brisbane, Australia). SUMO tag is cleavable from the target, DENV4 rNS1 using SUMO protease without leaving no extraneous residues attached to the target protein. Despite this we used SUMO*-DENV rNS1 fusion protein for immunization of mice. Our strategy has an advantage over immunization with cleaved DENV4 NS1 because it avoids the time and effort required to cleave the SUMO* tag from DENV4 NS1. In addition, it reduces the loss of protein during cleavage and re-purification steps to remove the SUMO* tag.

Characteristics of DENV-4 Monoclonal Antibodies. A total of six MAb-secreting hybridoma clones were isolated from SUMO*-DENV4 rNS1 fusion protein primed splenocytes with Sp2/0 cells. A combination of three methods: western blot assay, iELISA and cell-based ELISA were used to select hybridoma clones that could secret MAbs reactive to DENV NS1. Three MAbs designated hereafter as 3H7A9, 6D4B10, and 8A6F2 had reactivity to DENV4 rNS1, but not to the SUMO* tag. Also, these three MAbs did not cross-react with any of rNS1s from the other three heterologous DENV serotypes and other related Flaviviruses (Yellow Fever Virus (YFV) and West Nile Virus (WNV)). The remaining three MAbs 10H10B5, 10H8F7, and 4B6C10 were found to be specific to the SUMO* tag (Table 2, FIG. 3, FIG. 4 and FIG. 5). This result was expected since the mice were immunized with SUMO*-DENV4 rNS1 fusion protein, and the relative size of the SUMO* tag, approximately 11.5 kDa. The light-chain and heavy-chain isotypes of the six MAbs, including those which are DENV4 serotype-specific, were IgG2b and K, respectively. Competition ELISA results (data not shown) in combination with result from sequencing the three complementarity determining regions (CDR1, CDR2, and CDR3) of MAbs (Supplement Figure) revealed that our three DENV4 NS1 serotype-specific MAbs are distinct with different binding regions on the DENV4 NS1.

Figure 3:
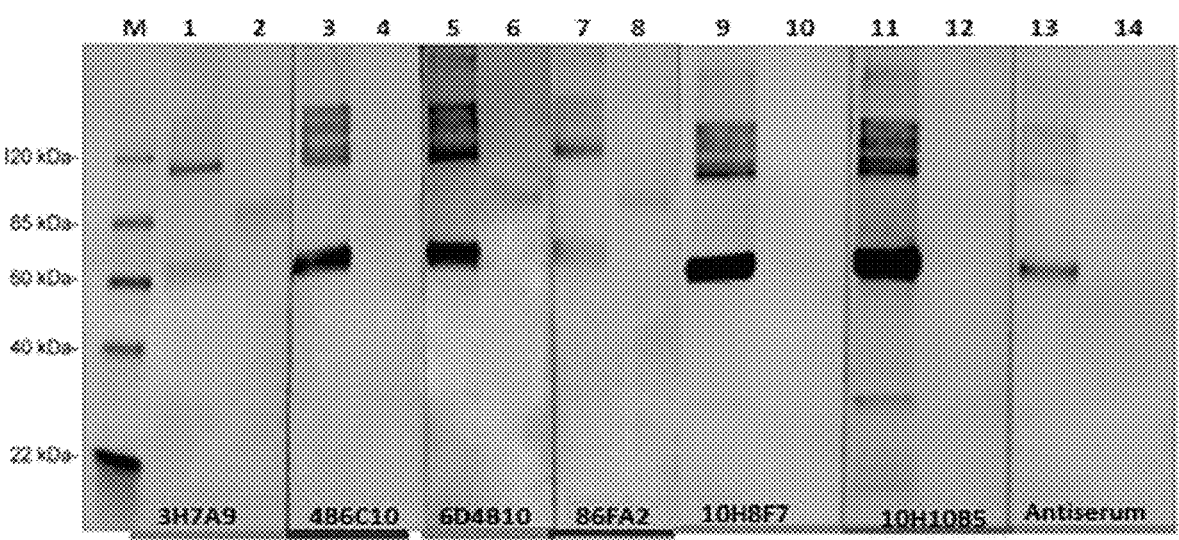
FIG. 3. Western blot assay to determine the reactivity of hybridoma supernatants to SUMO*-NS1 fusion protein, as well as unfused rNS1 protein. M: molecular markers; Lanes 1 and 2: 3H7A9; Lanes 3 and 4: 4B6C10; Lanes 5 and 6: 6D4B10; Lanes 7 and 8: 8A6F2; Lanes 9 &10: 10H8F7; Lanes 11 and 12: 10H10B5; and Lanes 13 and 14: Antiserum of mouse ME 1:100, reactivity to SUMO*-DENV NS1 fusion protein and unfused DENV rNS1, respectively.
Figure 4A:
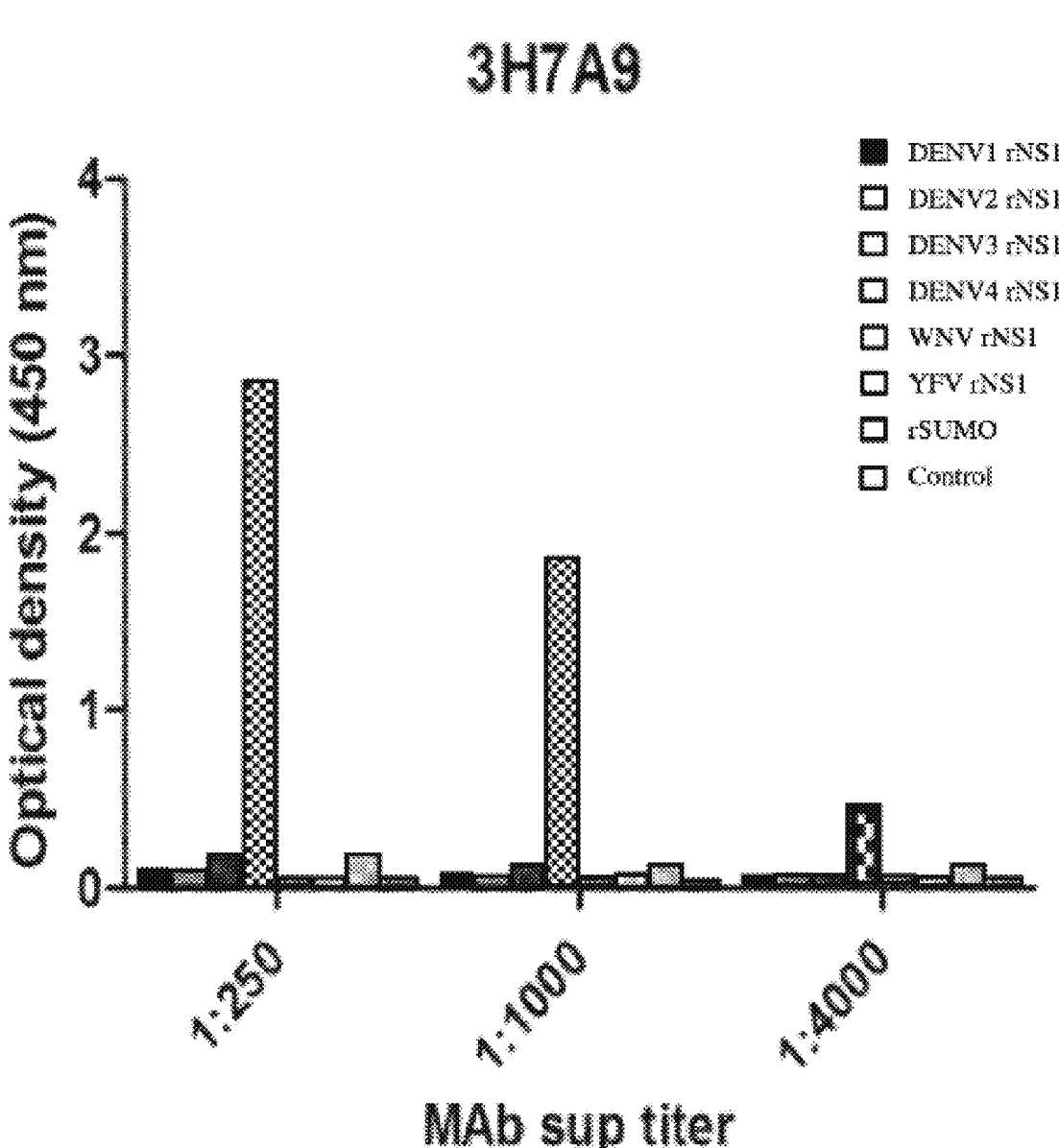
FIGS. 4A, 4B, 4C, and 4D. Serotype-specificity of Monoclonal antibodies (MAbs 3H7A9, 8A6F2, 6D4B10 and 10H10B5) for DENV4 as determined by iELISA. The bars show mean optical density at 450 nm, which measures MAb reactivity to NS1s from all four DENV4 serotypes and other flaviviruses such as Yellow Fever Virus (YFV) and West Nile Virus (WNV) as well as the SUMO protein that was used as a tag of solubility and stability to the fusion DENV4 rNS1 protein (FIG. 1). MAbs 3H7A9 (FIG. 4A), 6D4B10 (FIG. 4B), and 8A6F2 (FIG. 4C) represent anti-NS1 MAbs specific to DENV4. MAb 10H10B5 (FIG. 4D), which is reactive to SUMO*, represents one of the three undesirable MAbs generated from immunization of SUMO*-DENV4 rNS1 fusion protein, and was included as a control. The OD value for DENV4-serotype MAbs against rNS1 of other flaviviruses and recombinant SUMO protein is below 0. In contrast, MAbs reactive only to SUMO protein, e.g. 10H10B5, did not show any reactivity to rNS1 of any of the flaviviruses.
Figure 4B:
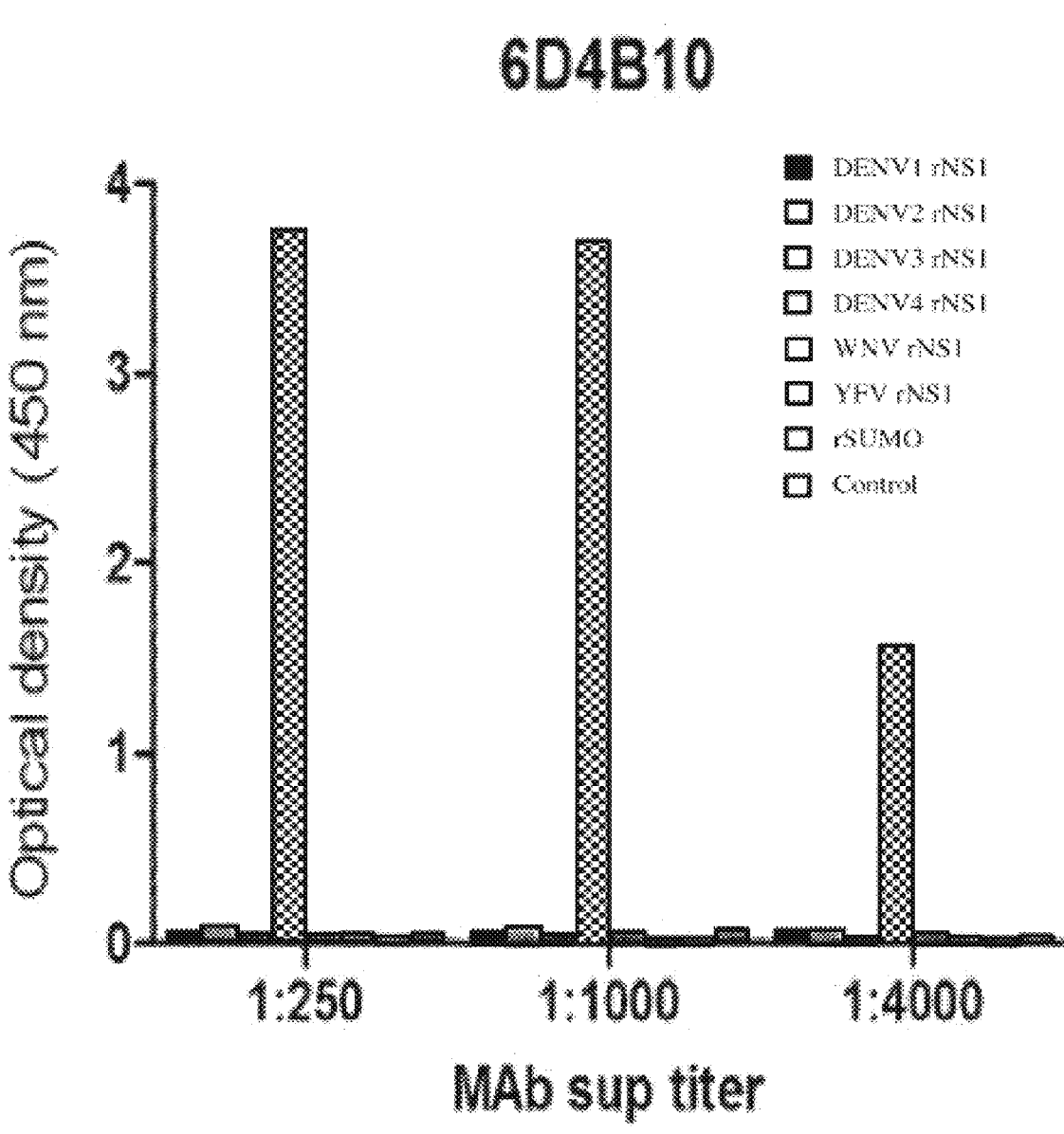
Figure 4C:
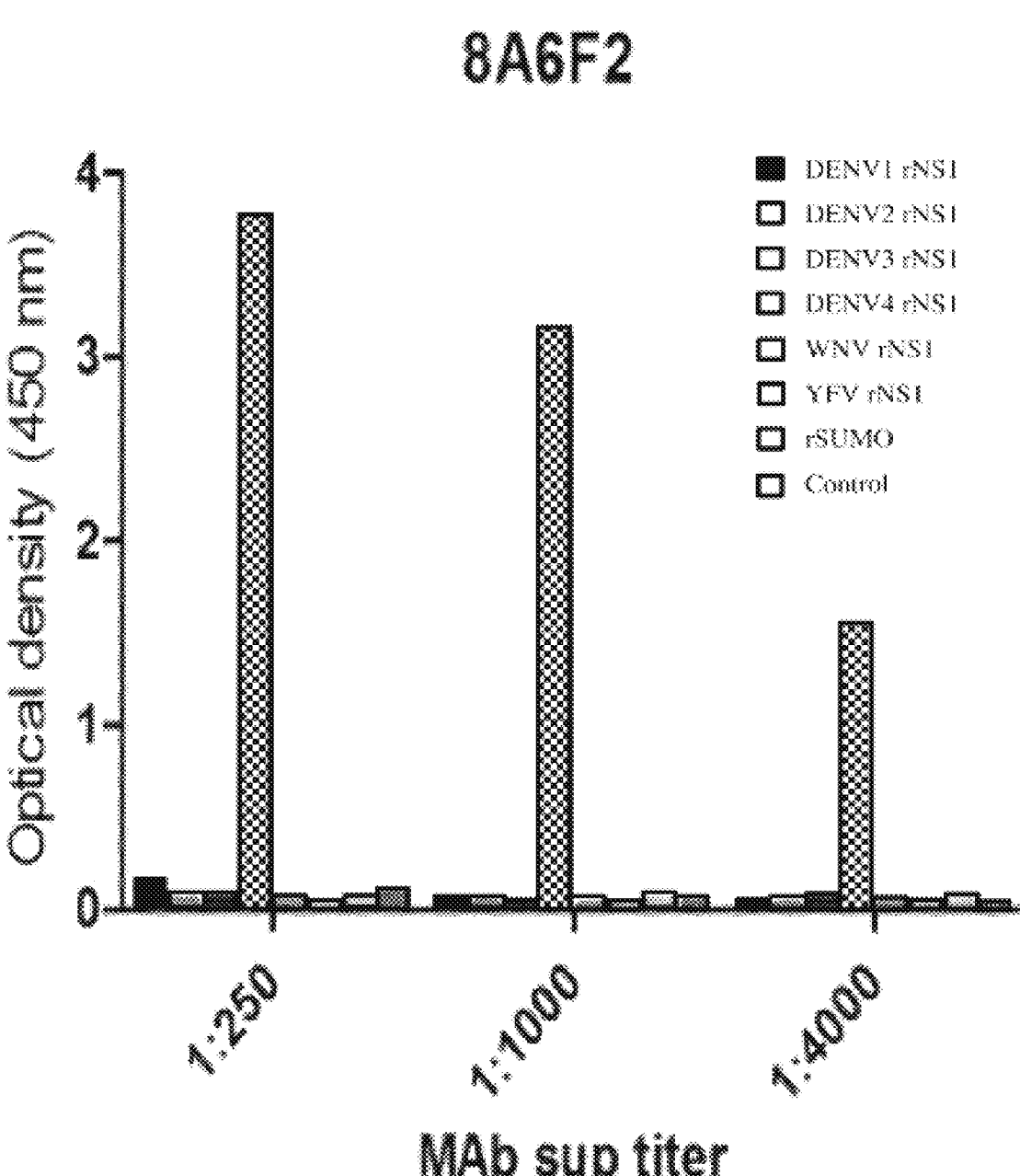
Figure 4D:
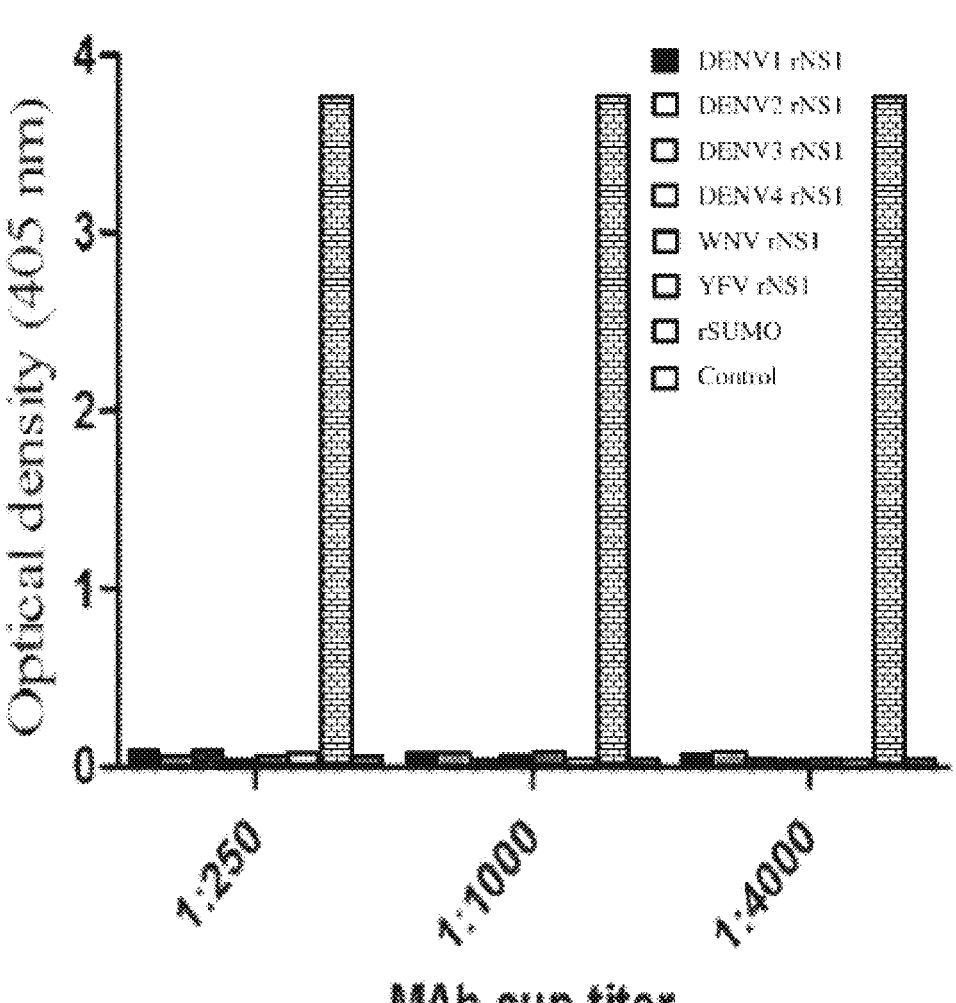
Figure 5A:
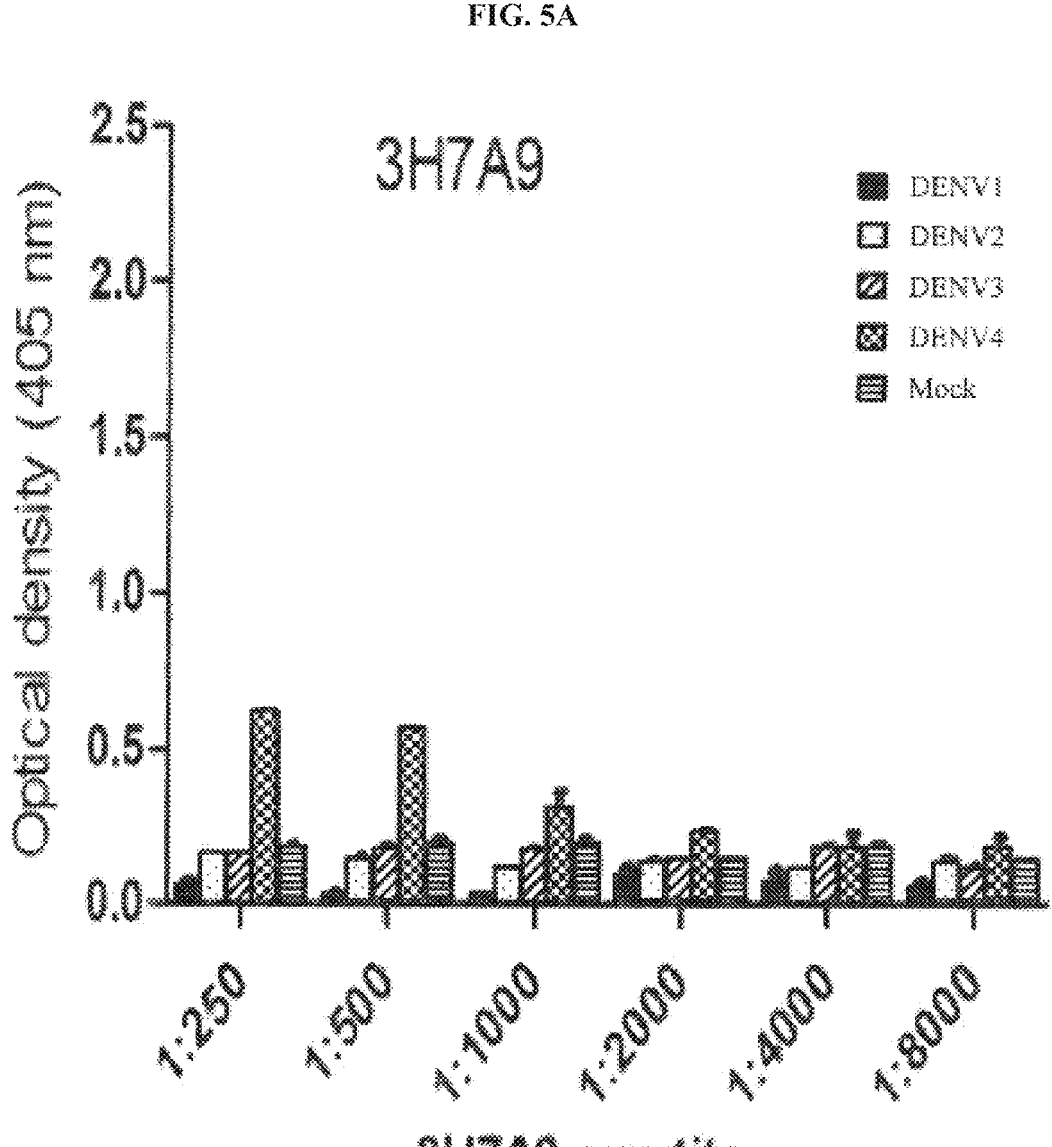
FIGS. 5A, 5B, 5C, and 5D. DENV4 serotype-specificity of MAbs 3H7A9, 8A6F2, 6D4B10 and 10H10B5 as determined by cell-based ELISA. The bars show mean optical density at 450 nm that measures MAb's reactivity to dimeric NS1 expressed on DENV1-4-infected Vero cells. Mock-infected Vero cells were included as a control.
Figure 5B:
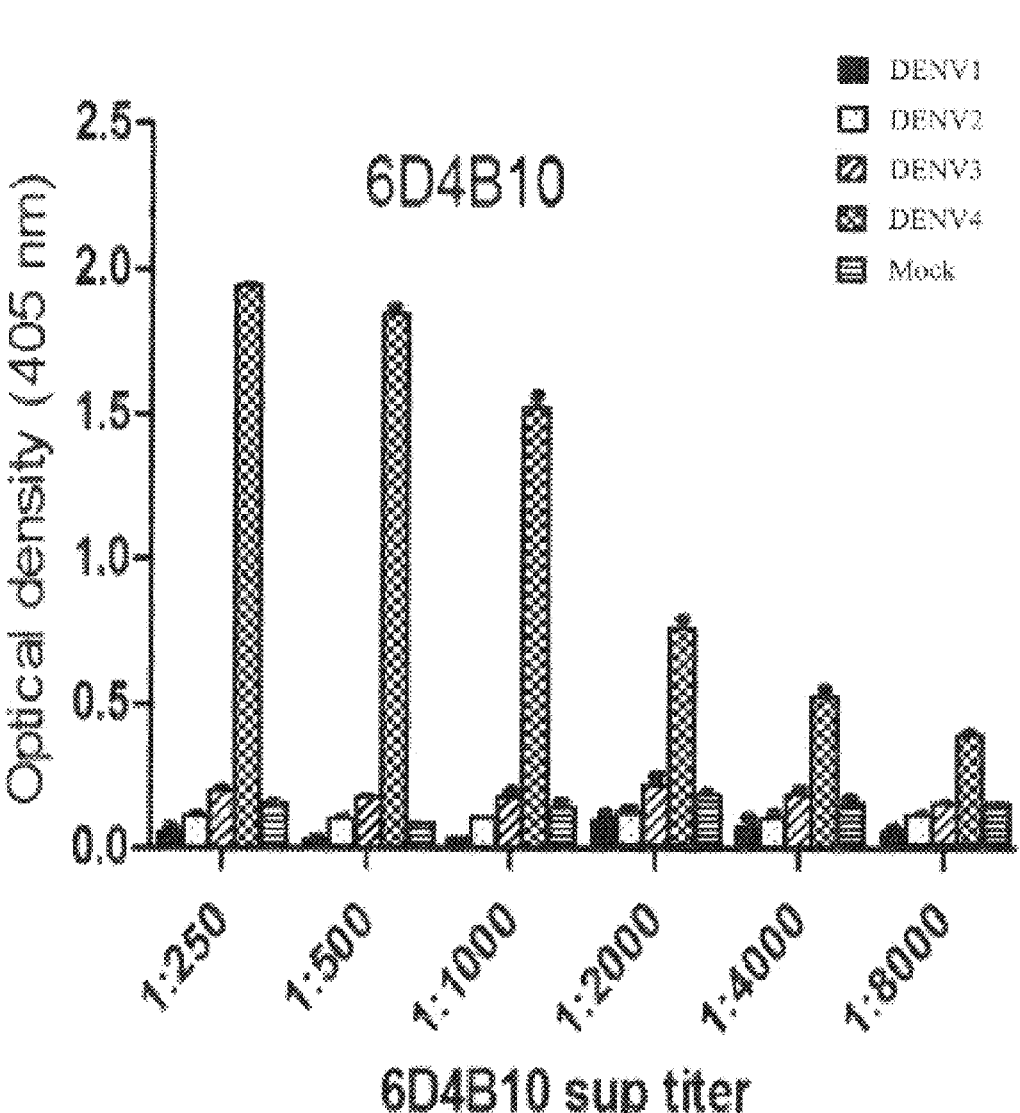
Figure 5C:
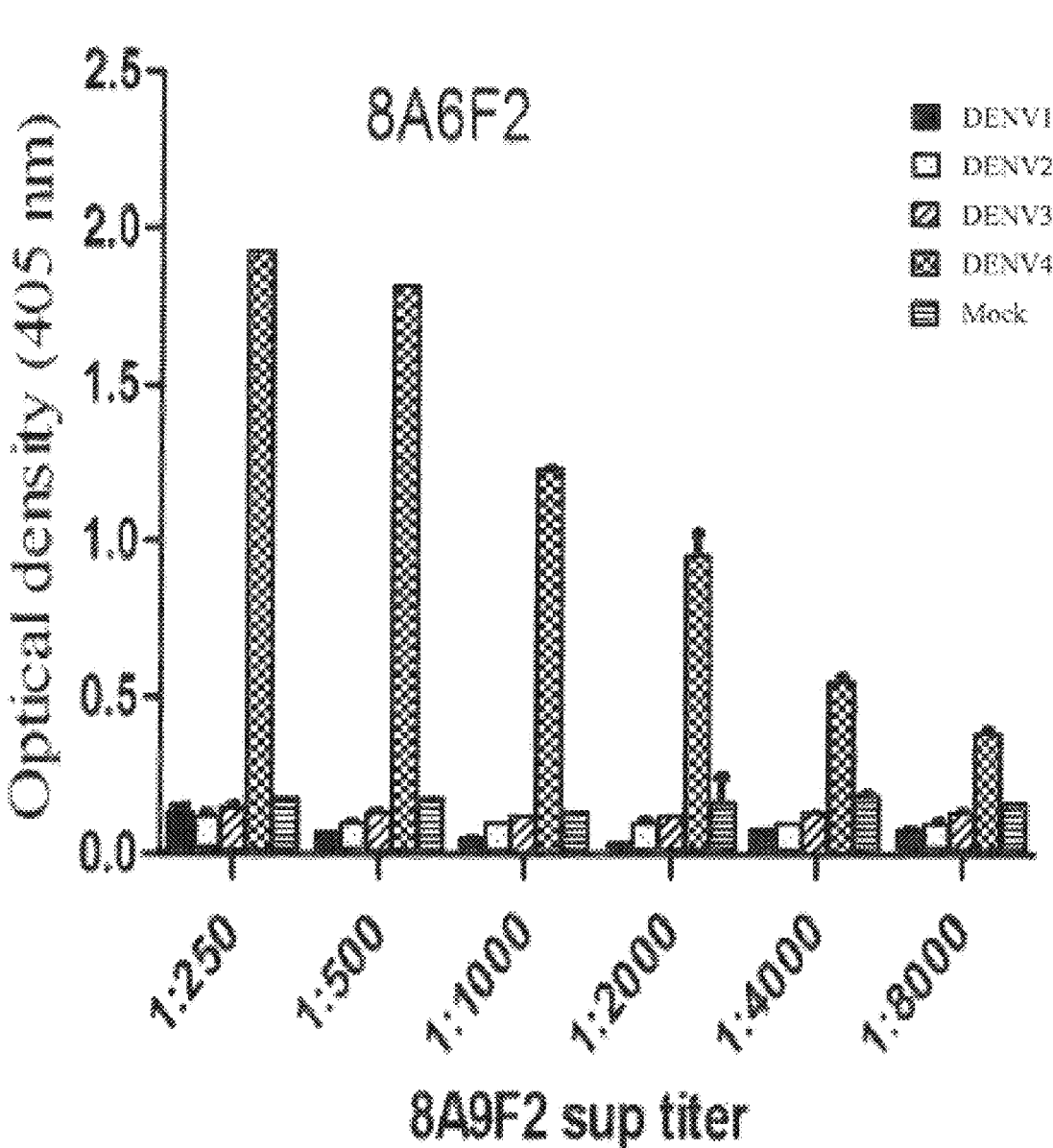
Figure 5D:
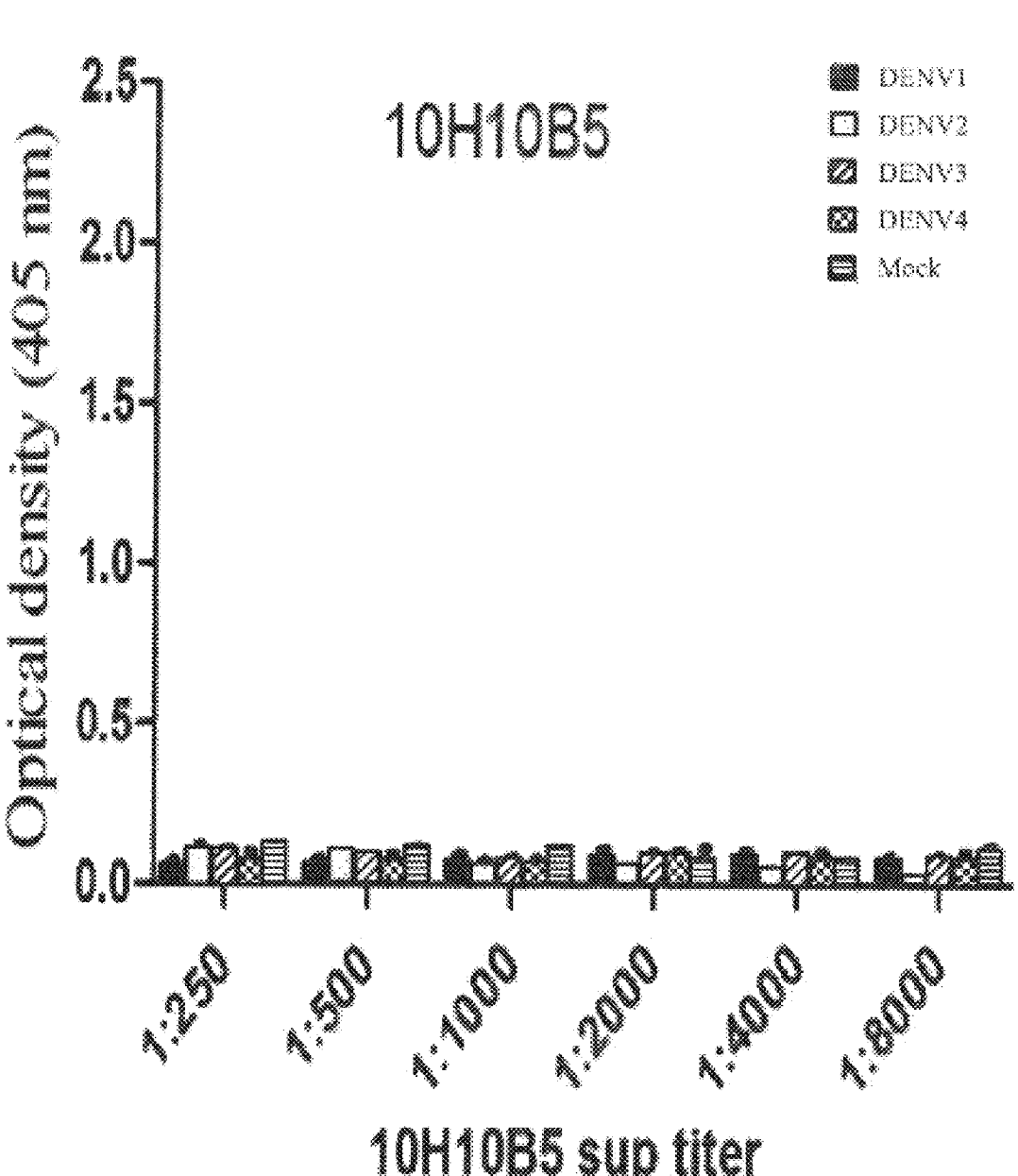

Anti-DENV4 Monoclonal Antibodies were DENV4 Specific and Bind to Monomeric, Dimeric, and Hexameric DENV4 NS1 Isoforms. DENV4 serotype specificity of MAbs (3H7A9, 6D4B10, and 8A6F2) was demonstrated in fixed cell-based ELISA and in iELISA using both cell culture supernatants from DENV1-DENV4 infected Vero cells culture and rNS1s of DENV1 (Native Antigen Company, Oxfordshire, UK). (Table 2 and 3). Western blot analysis of supernatants from the six clones after SDS-PAGE separation of SUMO*-DENV4 rNS1 protein, as well as unfused DENV4 rNS1s, revealed that the binding affinity of the three MAbs (3H7A9, 6D4B10, and 8A6F2) was to the linear epitopes on both monomeric and dimeric DENV4 NS1 isoforms (FIG. 3). Additionally, these MAbs exhibited reactivity to supernatants from DENV4-infected Vero cell culture, suggesting that the linear epitopes targeted by these three MAbs could also present on hexameric DENV4 NS1. Results from these three assays, including the Western blot analysis, indicate that the MAbs are capable of recognizing/binding to all three DENV4 NS1 isoforms (monomeric, dimeric and hexameric) (Table 2, Table 3, and FIG. 3). MAbs Serotype-Specificity.

TABLE 2

Isotype, epitope, and iELISA results of six anti-DENV4 monoclonal antibodies

| | | | iELISA (reactivity MAbs to different recombinant proteins) | | | | | | | |
|---|---|---|---|---|---|---|---|---|---|---|
| MAb | Isotype | Epitope | rNS DENV1 | rNS1 DENV2 | rNS1 DENV3 | rNS1 DENV4 | rNS1 WNV | rNS1 YFV | SUMO | SUMO*-NS1 fusion protein |
| 10H8F7 | IgG2b/K | Linear | − | − | − | − | − | − | + | + |
| 4B6C10 | IgG2b/K | Linear | − | − | − | − | − | − | + | + |
| 3H7A9 | IgG2b/K | Linear | − | − | − | + | − | − | − | + |
| 8A6F2 | IgG2b/K | Linear | − | − | − | + | − | − | − | + |
| 10H10B5 | IgG2b/K | Linear | − | − | − | − | − | − | + | + |
| 6D4B10 | IgG2b/K | Linear | − | − | − | + | − | − | − | + | rNS1 = recombinant non-structural protein 1
DENV = dengue viruses
SUMO = small-ubiquitin-like modifier
YFV = Yellow Fever Virus
WNV = West Nile Virus

TABLE 3

Monoclonal antibody reactivity to native
DENV1-4 NS1 in cell based ELISA and iELISA

| | Reactivity to native NS1 | | | | | | | |
|---|---|---|---|---|---|---|---|---|
| | Cell-Based ELISA (NS1 on surface infected Vero cells) | | | | iELISA (NS1 in Vero cell culture supernatant) | | | |
| MAb | DENV1 | DENV2 | DENV3 | DENV4 | DENV1 | DENV2 | DENV3 | DENV4 |
| 10H8F7 | − | − | − | − | − | − | − | − |
| 4B6C10 | − | − | − | − | − | − | − | − |
| 3H7A9 | − | − | − | + | − | − | − | + |
| 8A6F2 | − | − | − | + | − | − | − | + |
| 10H10B5 | − | − | − | − | − | − | − | − |
| 6D4B10 | − | − | − | + | − | − | − | + |

Figure 6A:
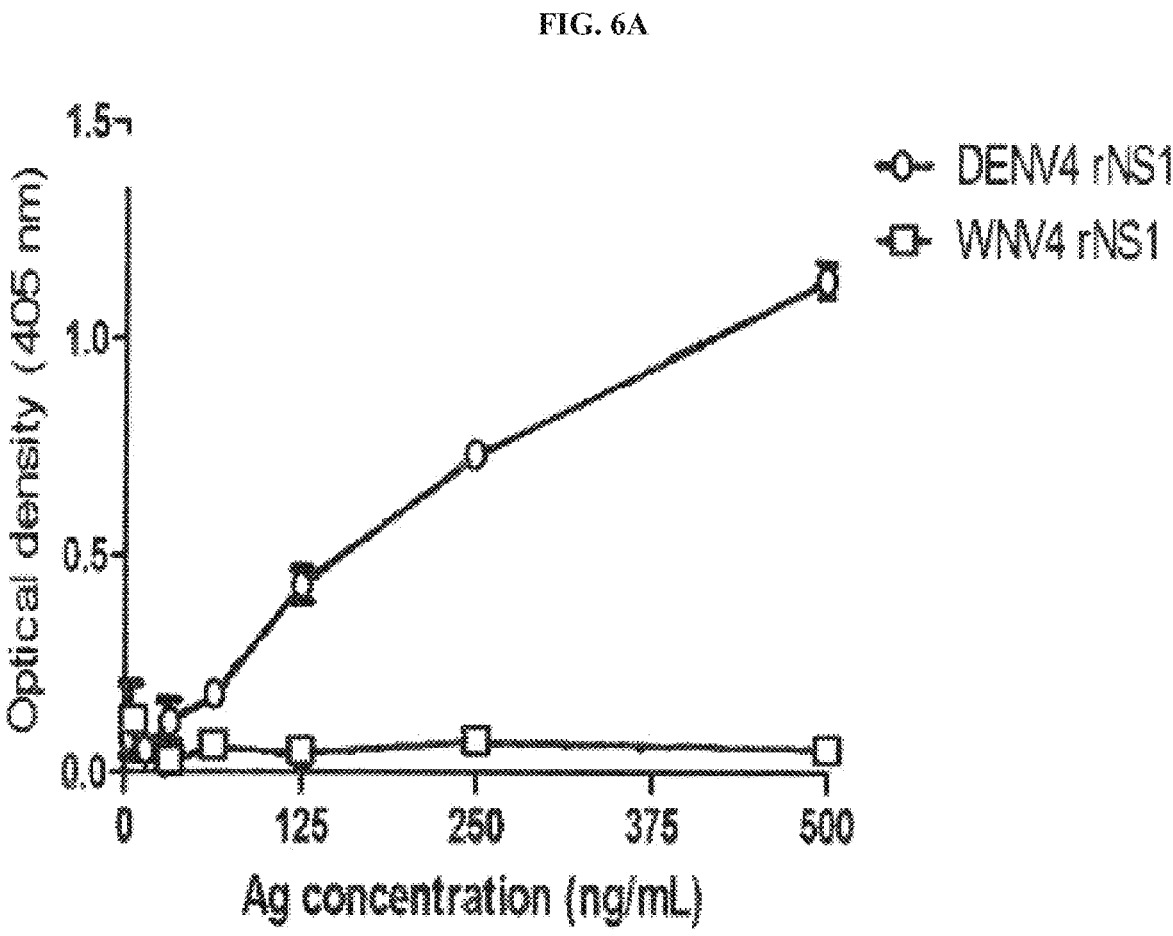
FIGS. 6A and 6B. Analysis of capture/detector MAbs pairs for the development of DENV4 serotype specific NS1 capture ELISA. The curves represent limit of detection (LOD) curves for matched pairs of MAbs of the present disclosure: 6A) 8A6F2/biotinylated 6D4B10, and 6B) 6D4B10/biotinylated 8A6F2. The optical density (OD) values at 450 nm were obtained at various concentration of DENV4 rNS1 with optimal concentrations for the coating antibody, 10 μg/ml; capture antibody, 1:2000 dilution; and streptavidin-tagged horseradish peroxidase (HRP-SP), 1:2000 dilution. West Nile Virus was used as the control.
Figure 6B:
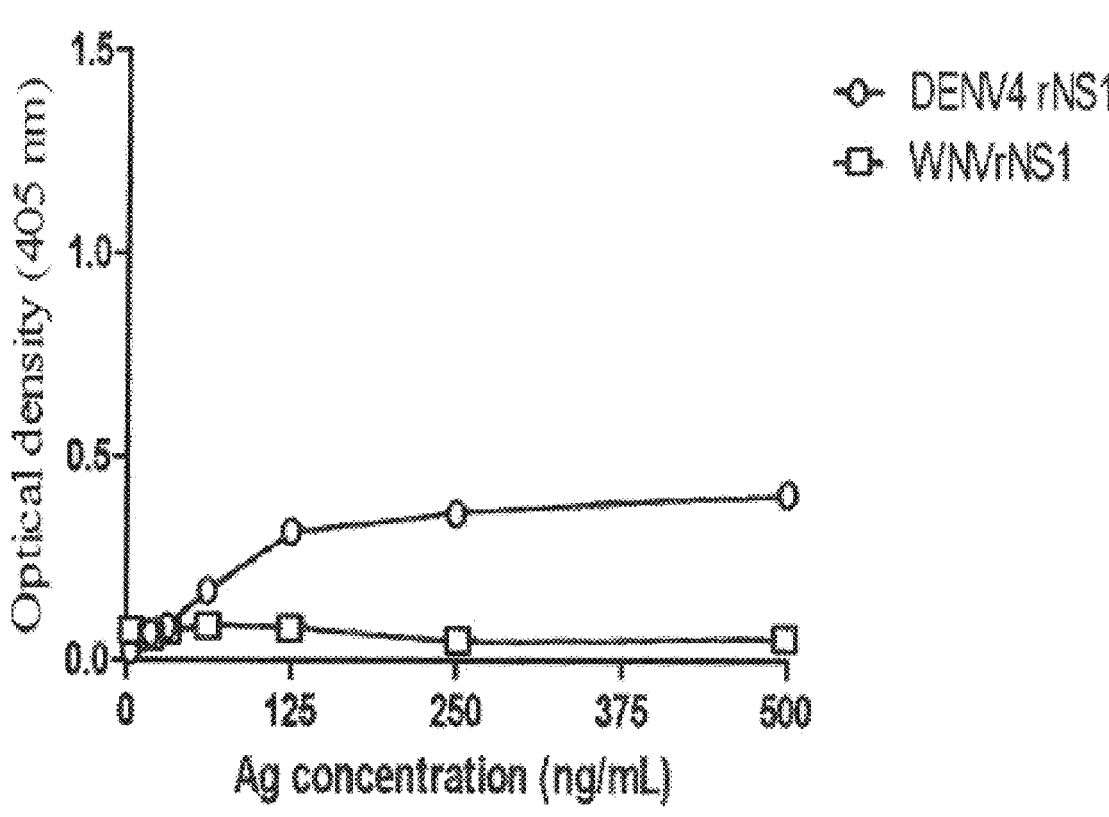

DENV NS1 Capture ELISA is Specific to DENV4. Results from competition ELISA (data not shown) confirmed that the three MAbs 3H7A9, 6D4B10, and 8A6F2 recognized distinct epitopes on DENV4 NS1, indicating a pair of these MAbs may be able to be used to develop new NS1 (e.g., DENV4 NS1) specific detection tests/assays. However, Mab 3H7A9 had a lower relative affinity (FIG. 4) and was not utilized for development of the NS1 capture assay of the present disclosure. Thus, only MAbs 6D4B10 and 8A6F2 were utilized to develop the NS1 capture ELISA. Based on the limit of detection (LOD) curves, shown in FIG. 6, a matched pair 8A6F2/biotinylated 6D4B10 had the lowest LOD while a matched pair 6D4B10/B-8A6F2 was not robust to capture and/or detect DENV4 rNS1 even at a higher concentration (FIG. 6B). Those matched MAbs pairs that did not perform well could be due to, but in no way limited to: (i) the denaturation/random orientation of 6D4B10 as a result of direct binding to the microtiter plate, (ii) biotin molecules might have bound on the antigen binding region of 8A6F2, or (iii) a combination of (i) and (ii). Nevertheless, result from a direct ELISA (data not shown), in which microtiter plate-wells were coated overnight with DENV4 rNS1, and bound antigen was detected by biotinylated 8A6F2, suggest that the loss of antigen-antibody binding in an NS1 capture ELISA based on match pair 6D4B10/biotinylated 8A6F2 was not linked to the biotinlyation.

Determination of the best working concentration of capture and detection was done by checkerboard titration and the optimal concentrations for coating MAb 8A6F2 and detection MAb biotinylated 6D4B10 were found to be 10 µg/mL and 1:2000 dilution, respectively.

After optimization of the NS1 capture ELISA specific to DENV4, the ELISA's utility was established and validate using culture supernatants obtained from DENV1-4 infected Vero cells. As expected, only culture supernatants from DENV4-infected Vero cells showed reactivity whereas culture supernatants from the other three DENV serotypes-infected Vero cell showed no reactivity.

Discussion of the Examples. DENV4 NS1 was expressed using SUMO fusion technology in Sf21 insect cells. The Examples here demonstrate that DENV NS1 protein SUMO* expression was superior to *E. coli* and standard baculovirus antigen expression because SUMO* tagged DENV4 rNS1 was secreted as a soluble molecule in culture medium. Furthermore, the purified SUMO* tagged DENV NSA1 did not require a complex multi-step process to solubilize and refold the expressed DENV NS1. To the inventor's knowledge, this is the first report regarding a successful expression of soluble and stable DENV4 NS1 with correct folding through the use of SUMO fusion technology. The present application demonstrates the utility of purified SUMO*-DENV rNS1 for the generation of MAbs that could be used to develop immunodiagnostic tests for Dengue.

Production of a properly-folded soluble NS1 protein appears to be crucial for the development of MAbs, which are reactive to epitopes on hexameric NS1. Isolation and purification of proteins expressed in *E. coli*, require solubilization in harsh detergents (e.g., SDS and urea), which denatures the target protein and require complex refolding processes. DENV NS1 expression in *E. coli* often resulted in insoluble aggregates (i.e., inclusion bodies). Even though it is possible to attain the correct 3-D configuration of the denatured protein following refolding, there is no guarantee this will occur. Expression of rNS1 in Sf insect cell lines, such as Sf9 and SF21, using a baculovirus expression system has been utilized, but in the inventor's experience (unpublished data), the expressed rNS1 protein also remained insoluble, and required solubilization and refolding.

The present disclosure provides six Mab-secreting hybridomas reactive to the SUMO*-DENV4 NS1 fusion protein were generated, of which three were reactive to the SUMO* tag, thereby indicating that the tag is highly immunogenic. The remaining three MAbs (3H7A9, 6D4B10, and 8A6F2) were found to be DENV4 serotype-specific.

Serotype-specific anti-DENV NS1 MAbs is crucial for the development of NS1 test/assay that detects dengue virus infection early (e.g., early in the course of Dengue illness) and simultaneously determines the infected DENV serotype. The MAbs (3H7A9, 6D4B10 and 8A6F2) developed in the present disclosure are highly specific to DENV4, as demonstrated by two different methods, cell-based ELISA, and iELISA. Of the three serotype-specific MAbs developed, 6D4B10 and 8A6F2 show higher affinity to the hexameric DENV4 rNS1 and dimeric DENV4 NS1 expressed in Vero cells. Additionally, the Western blot assay results under reducing conditions demonstrated that the reactivity to monomeric DENV rNS1 was with lower affinity.

A competition ELISA was performed to determine if the three MAbs bind to the same or distinct epitopes of DENV4 NS1. The results (data not shown) confirmed that all three MAbs (3H7A9, 6D4B10 and 8A6F2) bind to distinct non-overlapping regions and can be used to develop sandwich immunodiagnostic assays. The distinctness of these three MAbs was further verified by sequencing the three complementary determining regions (CDR1, CFR2, and CDR3) of the MAbs. MAb 3H7A9 was DENV4 serotype-specific, but had weak affinity to DENV4, and was, therefore, not used for assay development. MAbs 6D4B10 and 8A6F2 were chosen to develop a NS1 capture ELISA. In order to use biotin-streptavidin based capture ELISA format, different pairs of unbiotinylated and biotinylated MAbs were evaluated. Subsequently, a match pair of unbiotinylated 8A6F2 as a capture antibody and biotinylated (B)-6D4B10 as a detection antibody provided the most robust results compared to 6D4B10 as the capture antibody and (B)-8A6F2 as the detector antibody. The reason for the poor performance of the later matched pair of MAbs may be due to: (i) the denaturation/random orientation of 6D4B10 as a result of direct binding to the microtiter plate, (ii) biotin molecules binding to the antigen binding region of 8A6F2, or (iii) a combination of (i) and (ii). Nevertheless, a direct ELISA (data not shown), in which microtiter plate-wells were coated with DENV4 rNS1 and detected by (B)-8A6F2), showed reactivity of the biotinylated 8A6F2 to DENV4 fNSA1 protein, suggesting the loss of antigen-antibody binding in the NS1 capture ELISA format (captured with 6D4B10 and detected with (B)-8A6F2) was not due to the biotinlyation. As such, this MAb pair (6D4B10/(B)-8A6F2) may function efficiently if one avoids direct binding of 6D4B10 to the surface of the microplate.

By using lower affinity capture Mab, 6D4B10 immobilization method or a linker, the DENV4 NS1 specific capture ELISA was developed using 8A6F2 as a capture antibody and (B)-6D4B10 as detection antibody. The DENV4 serotype-specific ELISA was assessed using rNS1 of Flaviviruses, including all four DENV serotypes and culture supernatants from Vero cell-infected with all four DENV serotypes. The results confirmed that these MAbs specifically bound to DENV4 in the NS1 capture ELISA.

The inventors sought to develop a DENV4 ELISA because prior NS1 tests for detecting DNV4 infections have limited sensitivity. Recent studies using retrospective samples from South America demonstrate lower DENV4 sensitivity for seven commercially available NS1 Ag tests, as compared to the other three serotypes. Also, a meta-analysis for DENV detection in Asia also demonstrated that the lowest sensitivity of commercial NS1 Ag tests is for the DENV4 detection. Furthermore, studies conducted in Brazil demonstrated the lower sensitivity of Platelia NS1 Ag ELISA (Bio-Rad®, Hercules, California, USA) for DENV4 detection. Collectively, these data suggest the need for development of new NS1 Ag detection test with higher sensitivity to DENV4.

Another factor that could have contributed to the poor sensitivity of NS1 Ag detection tests for DENV4 is the low level of expression of NS1 in DENV4-infected patients, as compared to dengue patients infected with the other three serotypes. An NS1 capture ELISA specific to DENV4 could improve the detection of DENV4 cases and a serotype-specific NS1 Ag test can identify dengue and the infecting DENV serotype. NS1 ELISAs for each one of the four DENV serotypes have been previously described. However, none of these ELISAs are commercially available. As a result, the only commonly used laboratory methods to determine DENV serotype currently is RT-PCR. There are two main advantages in identifying the DENV serotype: (i) risk factors for severe dengue have associated to more pathogenic DENV serotypes, and (ii) the sequence of infection of DENV serotype in primary and secondary infections is also believed to be a risk factor for severe disease. Taken together, there is a need for a DENV4 serotype-specific NS1 tests that can detect NS1 in the serum of DENV4-infected patients at the lowest possible LOD.

The three DENV4-specific MAbs directed against SUMO\*-DENV4 rNS1 fusion protein were generated. Based on characterization results and competition ELISA, the NS1 capture ELISA for potential early detection DENV4 infection was established using a combination of two highly sensitive MAbs (8A6F2 as coating antibody and biotinylated 6D4B10 as detection antibody) and an optimized protocol was developed. The assay was sensitive and specific to DENV4 with no cross-reactivity to the three other DENV serotypes and other heterologous Flaviviruses. The Examples of the present disclosure indicate that the developed MAbs are useful reagents for the development of immunodiagnostic assays (such as, ELISAs and lateral flow assays) that specifically detect DENV4 infection. The DENV serotype-specific MAbs described herein have the potential to change the way we detect dengue by providing tests that are user friendly to resource poor regions to adopt them for diagnosing dengue. Given that the current commercial NS1 tests are less sensitivity to DENV4, the present test/assay could also provide an alternative test in regions where DENV4 circulates.

Specific Embodiments:

According to an aspect, the present disclosure provides an antibody or antigen-binding fragment thereof that binds specifically to Dengue virus serotype 4 (DENV4), wherein the antibody or antigen-binding fragment comprises: a heavy chain variable region that comprises at least one CDR amino acid sequence selected from the group consisting of: SGYNWH (SEQ ID NO: 1), YIHYSGGTNYNPSLKS (SEQ ID NO: 2), RTGTVPFAY (SEQ ID NO: 3), SYVMH (SEQ ID NO: 4), YLNPYNDDTKYNEKFKG (SEQ ID NO: 5), and GPPYALDY (SEQ ID NO: 6).

In any aspect or embodiment described herein, the antigen-binding fragment is selected from the group consisting of a Fab fragment, a F(ab)', a F(ab)'2 fragment, or a single-chain variable fragments (scFvs).

In any aspect or embodiment described herein, the antibody or antigen-binding fragment thereof is specific for the DENV4 Non-structural protein 1 (NS1).

In certain embodiments, the antibody or antigen binding fragment thereof comprises: a heavy chain variable region that comprises at least one CDR amino acid sequence selected from the group consisting of: SGYNWH (SEQ ID NO: 1), YIHYSGGTNYNPSLKS (SEQ ID NO: 2), RTGTVPFAY (SEQ ID NO: 3), SYVMH (SEQ ID NO: 4), YLNPYNDDTKYNEKFKG (SEQ ID NO: 5), GPPYALDY (SEQ ID NO: 6). DTYMH (SEQ ID NO: 37), YLNPYNDDTKYNEKFKG (SEQ ID NO: 38), and GGI-FYYYGSSYSYAMDY (SEQ ID NO: 39).

In any aspect or embodiment described herein, the antibody or antigen-binding fragment thereof of further comprises a light chain variable region that comprises at least one CDR amino acid sequence selected from the group consisting of: SVSSSISSSNLH (SEQ ID NO: 7), GTSN-LAS (SEQ ID NO: 8), QQWSSYPLT (SEQ ID NO: 9), RASQDISNYLN (SEQ ID NO: 10), YTSRLHS (SEQ ID NO: 11), QQGNTLPRT (SEQ ID NO: 12), TASSSVSS-SYLH (SEQ ID NO: 40), STSNLAS (SEQ ID NO: 41), and HQYHRSPYT (SEQ ID NO: 42).

In any aspect or embodiment described herein, the CDR amino acid sequence of the heavy chain variable region is selected from the group consisting of: SGYNWH (SEQ ID NO: 1), YIHYSGGTNYNPSLKS (SEQ ID NO: 2), RTGTVPFAY (SEQ ID NO: 3); and the CDR amino acid sequence of the light chain variable region is selected from the group consisting of: SVSSSISSSNLH (SEQ ID NO: 7), GTSNLAS (SEQ ID NO: 8), and QQWSSYPLT (SEQ ID NO: 9).

In any aspect or embodiment described herein, the CDR amino acid sequence of the heavy chain variable region is selected from the group consisting of: SYVMH (SEQ ID NO: 4), YLNPYNDDTKYNEKFKG (SEQ ID NO: 5), and GPPYALDY (SEQ ID NO: 6); and the CDR amino acid sequence of the light chain variable region is selected from the group consisting of: RASQDISNYLN (SEQ ID NO: 10), YTSRLHS (SEQ ID NO: 11), and QQGNTLPRT (SEQ ID NO: 12).

In any aspect or embodiment described herein, the CDR amino acid sequence of the heavy chain variable region is selected from the group consisting of: SYVMH (SEQ ID NO: 4), YLNPYNDDTKYNEKFKG (SEQ ID NO: 5), and GPPYALDY (SEQ ID NO: 6); and the CDR amino acid sequence of the light chain variable region is selected from the group consisting of: TASSSVSSSYLH (SEQ ID NO: 40), STSNLAS (SEQ ID NO: 41), and HQYHRSPYT (SEQ ID NO: 42).

In any aspect or embodiment described herein, the CDR amino acid sequence of the heavy chain variable region is selected from the group consisting of: DTYMH (SEQ ID NO: 37), YLNPYNDDTKYNEKFKG (SEQ ID NO: 38), and GGIFYYYGSSYSYAMDY (SEQ ID NO: 39); and the CDR amino acid sequence of the light chain variable region is selected from the group consisting of: RASQDISNYLN (SEQ ID NO: 10), YTSRLHS (SEQ ID NO: 11), and QQGNTLPRT (SEQ ID NO: 12).

In any aspect or embodiment described herein, the heavy chain variable region comprises the amino acid sequence of:

```
                              (SEQ ID NO: 13)
DVQLQESGPDLVKPSQSLSLTCTVTGYSITSGYNWHWIRQFPGNKLEW
```

-continued
```
MGYIHYSGGTNYNPSLKSRISITRDTSKNQFFLQLNSVTTEDTATYYC

ARRTGTVPFAYWGQGTLVTVSA,
```

```
                                      (SEQ ID NO: 14)
EVQLQQSGPELVKPGASVKMSCKASGYTFTSYVMHWVKQKPGQGLEWI

GYLNPYNDDTKYNEKFKGKATLTSDKSSSTAYMELSSLTSEDSAVYYC

AYGPPYALDYWGQGTSVTVSS,
or
```

```
                                      (SEQ ID NO: 43)
EVQLQQSGAELVKPGASVKLSCTASGFNIKDTYMHWVKQRPEQGLEWI

GRIDPANGNTQYGPKFQGKATITADTSSNTAYLQLSSLTSEDTAVYYC

ARGGIFYYYGSSYSYAMDYWGQGTSVTVSS.
```

In any aspect or embodiment described herein, the light chain variable region comprises the amino acid sequence of:

```
                                      (SEQ ID NO: 15)
EIVLTQSPALMAASPGEKVTITCSVSSSISSSNLHWYQQKSETSPKPW

IYGTSNLASGVPVRFSGSGSGTSYSLTISSMEAEDAATYYCQQWSSYP

LTFGGGTKLEIK,
```

```
                                      (SEQ ID NO: 16)
DIQMTQTTSSLSASLGDRVTISCRASQDISNYLNWYQQKPDGTVTLLI

YYTSRLHSGVPSRFSGSGSGTDYSLTISNLEQEDIATYFCQQGNTLPR

TFGGGTKLEIK,
or
```

```
                                      (SEQ ID NO: 44)
QIVLTQSPAIMTASLGERVTMTCTASSSVSSSYLHWYQQKPGSSPKLW

IYSTSNLASGVPARFSGSGSGTSYSLTISSMEAEDAATYYCHQYHRSP

YTFGGGTKLEIK.
```

In any aspect or embodiment described herein, the heavy chain variable region comprises the amino acid sequence of DVQLQESGPDLVKPSQSLSLTCTVTGYSITSGYN-WHWIRQFPGNKLEWMGYIHYSGGTN YNPSLKSRISITRDTSKNQFFLQLNSVTTEDTATYY-CARRTGTVPFAYWGQGTLVTVSA (SEQ ID NO: 13); and the light chain variable region comprises the amino acid sequence of

```
                                      (SEQ ID NO: 15)
EIVLTQSPALMAASPGEKVTITCSVSSSISSSNLHWYQQKSETSPKPW

IYGTSNLASGVPVRFSGSGSGTSYSLTISSMEAEDAATYYCQQWSSYP

LTFGGGTKLEIK.
```

In any aspect or embodiment described herein, the heavy chain variable region comprises the amino acid sequence of EVQLQQSGPELVKPGASVKMSCKASGYTFT-SYVMHWVKQKPGQGLEWIGYLNPYNDD TKYNEKFKGKATLTSDKSSSTAYMELSSLTSED-SAVYYCAYGPPYALDYWGQGTSVTV SS (SEQ ID NO: 14); and the light chain variable region comprises the amino acid sequence of

```
                                      (SEQ ID NO: 16)
DIQMTQTTSSLSASLGDRVTISCRASQDISNYLNWYQQKPD
```

-continued
```
GTVTLLIYYTSRLHSGVPSRFSGSGSGTDYSLTISNLEQED

IATYFCQQGNTLPRTFGGGTKLEIK.
```

In some embodiments, the heavy chain variable region comprises the amino acid sequence of EVQLQQSGAEL-VKPGASVKLSCTASGFNIKDTYMHWVKQRPEQ-GLEWIGRIDPANGNT QYGPKFQGKATITADTSSN-TAYLQLSSLTSEDTAVYYCARGGIFYYYGSSYSYAM DYW GQGTSVTVSS (SEQ ID NO: 43); and the light chain variable region comprises the amino acid sequence of

```
                                      (SEQ ID NO: 16)
DIQMTQTTSSLSASLGDRVTISCRASQDISNYLNWYQQKPD

GTVTLLIYYTSRLHSGVPSRFSGSGSGTDYSLTISNLEQED

IATYFCQQGNTLPRTFGGGTKLEIK.
```

In some embodiments, the heavy chain variable region comprises the amino acid sequence of EVQLQQSGPEL-VKPGASVKMSCKASGYTFTSYVMHWVKQKPGQ-GLEWIGYLNPYNDD TKYNEKFKGKATLT-SDKSSSTAYMELSSLTSEDSAVYYCAYGPPYALDYW GQGTSVTV SS (SEQ ID NO: 14); and the light chain variable region comprises the amino acid sequence of

```
                                      (SEQ ID NO: 44)
QIVLTQSPAIMTASLGERVTMTCTASSSVSSSYLHWYQQKP

GSSPKLWIYSTSNLASGVPARFSGSGSGTSYSLTISSMEAE

DAATYYCHQYHRSPYTFGGGTKLEIK.
```

In any aspect or embodiment described herein, the antibody is 3H7A9.

In any aspect or embodiment described herein, the antibody is 6D4B10.

In any aspect or embodiment described herein, the fragment of the antibody comprises an antigen-binding site/region of 3H7A9.

In any aspect or embodiment described herein, the fragment of the antibody comprises an antigen-binding site/region of 6D4B10.

According to another aspect, the present disclosure provides a pharmaceutical composition comprising the antibody or the fragment thereof of the present disclosure and a pharmaceutically acceptable carrier.

According to a further aspect, the present disclosure provides a method of diagnosing or detecting a DENV4 infection. The method comprises: contacting a sample from a patient with the antibody or antigen-binding fragment thereof of the present disclosure; and detecting the binding of NS1; and optionally administering an effective amount of a treatment effective for ameliorating at least one symptom of DENV4 infection.

In any aspect or embodiment described herein, contacting the blood sample comprises: contacting the blood sample to an immobilized antibody or antigen-binding fragment thereof of the present disclosure; and contacting the antibody retained DENV4 virion with a second antibody or antigen-binding fragment thereof of the present disclosure.

In any aspect or embodiment described herein, the immobilized antibody or antigen-binding fragment thereof and the second antibody or fragment thereof are different antibodies.

In any aspect or embodiment described herein, the secondary antibody or antigen-binding fragment thereof is linked to (e.g., chemically or covalent linked to) a detectable label.

In any aspect or embodiment described herein, the detectable label is selected from the group consisting of an enzyme, biotin, streptavidin, a radioactive molecule, and an immunofluorescent protein or dye.

In any aspect or embodiment described herein, when the detectable label is biotin or streptavidin, the method further comprises contacting a complex comprising a NS1 and the labeled antibody with a detection molecule that comprises streptavidin or biotin, respectively, linked to an immunofluorescent protein or dye or an enzyme.

In any aspect or embodiment described herein, the antibody is linked to (e.g., chemically or covalent linked to) a detectable label and optionally a bead, particle, or nanoparticle.

In any aspect or embodiment described herein, the detectable label is selected from the group consisting of an enzyme, biotin, streptavidin, a radioactive molecule, and an immunofluorescent protein or dye.

In any aspect or embodiment described herein, when the detectable label is biotin or streptavidin, the method further comprises contacting a complex comprising a NS1 and the labeled antibody with a detection molecule that comprises streptavidin or biotin, respectively, linked to an immunofluorescent protein or dye.

In any aspect or embodiment described herein, the bead, particle, or nanoparticle is a magnetic bead.

In any aspect or embodiment described herein, wherein the method further comprises separating a complex comprising NS1 and the labeled antibody or antigen-binding fragment thereof via the bead, particle or nanoparticle for detecting the binding of NS1.

In any aspect or embodiment described herein, the sample comprises a blood or a tissue sample.

In any aspect or embodiment described herein, the method further comprises administering at least one agent selected from the group consisting of an antibody or antigen-binding fragment of the present disclosure, the pharmaceutical composition of the present disclosure, acetaminophen, an analgesic with acetaminophen, and isotonic crystalloid solution, wherein the agent is effective at ameliorating or treating at least one system of the infection.

According to yet another aspect, the present disclosure provides a method of treating a DENV4 infection in a subject. The method comprises: administering to a subject in the need thereof an effective amount of the antibody or antigen-binding fragment thereof, or the pharmaceutical composition of the present disclosure, wherein the administering is effective at treating the infection.

According to an additional aspect, the present disclosure provides a method of producing/making a DENV NS1 specific antibody or fragment thereof. The method comprises: providing a nucleic acid expressing DENV NS1 fusion protein with a solubility and stability tag; producing a multimeric DENV NS1 complex; and immunizing an animal with the multimeric DENV NS1 complex, wherein immunizing the animal produces the DENV NS1 specific antibody.

In any aspect or embodiment described herein, wherein the method further comprises preparing at least one hybridoma from spleen cells of the immunized animal.

In any aspect or embodiment described herein, the solubility and stability tag includes a secretion signal.

In any aspect or embodiment described herein, the solubility and stability tag is a small ubiquitin-like modifier (SUMO) and/or the secretion signal is gp67.

In any aspect or embodiment described herein, providing the nucleic acid expressing DENV NS1 fusion protein comprises inserting the Dengue virus NS1 into a vector comprising the solubility and stability tag and optionally, the secretion signal.

In any aspect or embodiment described herein, the DENV NS1 is DENV4 NS1.

In any aspect or embodiment described herein, producing the multimeric DENV NS1 complex is performed with a eukaryotic expression system.

In any aspect or embodiment described herein, producing a multimeric DENV NS1 complex includes a host cell comprising a vector that expresses a serotype specific DENV NS1 antibody.

In any aspect or embodiment described herein, the host cell is a eukaryotic cell.

In any aspect or embodiment described herein, the eukaryotic cell is a Chinese hamster ovary (CHO) cell, a NS0 murine myeloma cell, PER.C6® human cells, an insect cell line, Sf9, or Sf21.

In any aspect or embodiment described herein, the eukaryotic expression system is a baculovirus expression system or a vaccinia virus expression system.

In any aspect or embodiment described herein, producing a multimeric DENV NS1 complex comprises infecting eukaryotic cells with a baculavirus expressing the DENV NS1 fusion protein.

In any aspect or embodiment described herein, the baculavirus expressing the DENV NS1 fusion protein is prepared by at least one of: transforming a bacteria with a vector comprising the DENV NS1 fusion protein; selecting a vector-transformed bacteria; extracting/purifying the vector from the vector-transformed bacteria; transforming a bacteria comprising a baculovirus shuttle vector; selecting a bacteria with a recombinant DENV NS1 fusion protein-baculovirus vector; extracting/purifying the recombinant DENV NS1 fusion protein-baculovirus vector; transfecting a eukaryotic cell with the recombinant DENV NS1 fusion protein-baculovirus vector; or collecting cell culture supernatant comprising the baculavirus expressing the DENV NS1 fusion protein.

In any aspect or embodiment described herein, immunizing the animal with the multimeric DENV NS1 complex includes at least one of: administering the multimeric DENV NS1 complex to the animal at least two times; isolating at least one primed spleen cell from the animals; fusing the primed spleen cell with a myeloma cell; or selecting a hybridoma cell expressing the DENV NS1 specific antibody.

In any aspect or embodiment described herein, the method further comprises humanizing the DENV NS1 specific antibody.

In any aspect or embodiment described herein, the method further comprises treating the DENV NS1 specific antibody to produce an antigen-binding fragment thereof.

In any aspect or embodiment described herein, treating comprises contacting the DENV NS1 specific antibody with an agent selected from the group consisting of (i) pepsin, (ii) papain, and (iii) pepsin and β-mercaptoethanol.

According to yet an additional aspect, the present disclosure provides an antibody or antigen-binding fragment thereof that binds specifically to Dengue virus serotype 4 (DENV4), wherein the antibody is: 8A6F2 or the antigen-binding fragment comprises at least at least one heavy chain or light chain CDR amino acid sequence from an antigen-binding site/region of 8A6F2; 3H7A9 or the antigen-binding fragment comprises at least at least one heavy chain or light chain CDR amino acid sequence from an antigen-binding site/region of 3H7A9; or 6D4B10 or the antigen-binding fragment comprises at least at least one heavy chain or light chain CDR amino acid sequence from an antigen-binding site/region of 6D4B10.

While the present invention has been described in some detail for purposes of clarity and understanding, one skilled in the art will appreciate that various changes in form and detail can be made without departing from the true scope of the invention. All figures, tables, and appendices, as well as patents, applications, and publications, referred to above, are hereby incorporated by reference.

REFERENCES

Alcon, S., A. Talarmin, M. Debruyne, A. Falconar, V. Deubel, and M. Flamand. 2002. 'Enzyme-linked immunosorbent assay specific to Dengue virus type 1 nonstructural protein NS1 reveals circulation of the antigen in the blood during the acute phase of disease in patients experiencing primary or secondary infections', *J Clin Microbiol,* 40:376-81.

Allonso, D., M. da Silva Rosa, D. R. Coelho, S. M. da Costa, R. M. Nogueira, F. A. Bozza, F. B. Santos, A. M. de Barcelos Alves, and R. Mohana-Borges. 2011. 'Polyclonal antibodies against properly folded Dengue virus NS1 protein expressed in *E. coli* enable sensitive and early dengue diagnosis', *J Virol* Methods, 175:109-16.

Allonso, D., M. D. Meneses, C. A. Fernandes, D. F. Ferreira, and R. Mohana-Borges. 2014. 'Assessing positivity and circulating levels of NS1 in samples from a 2012 dengue outbreak in Rio de Janeiro, Brazil', *PLoS One,* 9: e113634.

Amorim, J. H., B. F. Porchia, A. Balan, R. C. Cavalcante, S. M. da Costa, A. M. de Barcelos Alves, and L. C. de Souza Ferreira. 2010. 'Refolded dengue virus type 2 NS1 protein expressed in *Escherichia coli* preserves structural and immunological properties of the native protein', *J Virol Methods,* 167:186-92.

Aryati, A., H. Trimarsanto, B. Yohan, P. Wardhani, S. Fahri, and R. T. Sasmono. 2013. 'Performance of commercial dengue NS1 ELISA and molecular analysis of NS1 gene of dengue viruses obtained during surveillance in Indonesia', *BMC Infect Dis,* 13:611.

Bessoff, K., M. Delorey, W. Sun, and E. Hunsperger. 2008. 'Comparison of two commercially available dengue virus (DENV) NS1 capture enzyme-linked immunosorbent assays using a single clinical sample for diagnosis of acute DENV infection', *Clinical & Vaccine Immunology: CVI,* 15:1513-8.

Butt, T. R., S. C. Edavettal, J. P. Hall, and M. R. Mattern. 2005. 'SUMO fusion technology for difficult-to-express proteins', *Protein Expr Purif,* 43:1-9.

Chan, L. C., P. R. Young, C. Bletchly, and S. Reid. 2002. 'Production of the baculovirus-expressed dengue virus glycoprotein NS1 can be improved dramatically with optimised regimes for fed-batch cultures and the addition of the insect moulting hormone, 20-Hydroxyecdysone', *J Virol Methods,* 105:87-98.

Colombo, T. E., D. Vedovello, C. S. Araki, H. Cogo-Moreira, I. N. dos Santos, A. F. Reis, F. R. Costa, L. E. Cruz, L. Casagrande, L. J. Regatieri, J. F. Junior, R. V. Bronzoni, D. J. Schmidt, and M. L. Nogueira. 2013. 'Dengue-4 false negative results by Panbio® Dengue Early ELISA assay in Brazil', *J Clin Virol,* 58:710-2.

da Costa, V. G., A. C. Marques-Silva, and M. L. Moreli. 2014. 'A meta-analysis of the diagnostic accuracy of two commercial NS1 antigen ELISA tests for early dengue virus detection', *PLoS One,* 9: e94655.

Das, D., S. Mongkolaungkoon, and M. R. Suresh. 2009. 'Super induction of dengue virus NS1 protein in *E. coli'*, *Protein Expression & Purification,* 66:66-72.

Ding, X., D. Hu, Y. Chen, B. Di, J. Jin, Y. Pan, L. Qiu, Y. Wang, K. Wen, M. Wang, and X. Che. 2011. 'Full serotype- and group-specific NS1 capture enzyme-linked immunosorbent assay for rapid differential diagnosis of dengue virus infection', *Clin Vaccine Immunol,* 18:430-4.

Falconar, A. K., P. R. Young, and M. A. Miles. 1994. 'Precise location of sequential dengue virus subcomplex and complex B cell epitopes on the nonstructural-1 glycoprotein', *Arch Virol,* 137:315-26.

Flamand, M., F. Megret, M. Mathieu, J. Lepault, F. A. Rey, and V. Deubel. 1999. 'Dengue virus type 1 nonstructural glycoprotein NS1 is secreted from mammalian cells as a soluble hexamer in a glycosylation-dependent fashion', *J Virol,* 73:6104-10.

Gelanew, T., B. K. Poole-Smith, and E. Hunsperger. 2015. 'Development and characterization of mouse monoclonal antibodies against monomeric dengue virus non-structural glycoprotein 1 (NS1)', *J Virol* Methods, 222:214-23.

Guzman, M. G., T. Jaenisch, R. Gaczkowski, V. T. Ty Hang, S. D. Sekaran, A. Kroeger, S. Vazquez, D. Ruiz, E. Martinez, J. C. Mercado, A. Balmaseda, E. Harris, E. Dimano, P. S. Leano, S. Yoksan, E. Villegas, H. Benduzu, I. Villalobos, J. Farrar, and C. P. Simmons. 2010. 'Multicountry evaluation of the sensitivity and specificity of two commercially-available NS1 ELISA assays for dengue diagnosis', *PLoS Negl Trop Dis,* 4.

Hermann, L. L., B. Thaisomboonsuk, Y. Poolpanichupatam, R. G. Jarman, S. Kalayanarooj, A. Nisalak, I. K. Yoon, and S. Fernandez. 2014. 'Evaluation of a dengue NS1 antigen detection assay sensitivity and specificity for the diagnosis of acute dengue virus infection', *PLoS Negl Trop Dis,* 8: e3193.

Hunsperger, E. A., S. Yoksan, P. Buchy, V. C. Nguyen, S. D. Sekaran, D. A. Enria, S. Vazquez, E. Cartozian, J. L. Pelegrino, H. Artsob, M. G. Guzman, P. Olliaro, J. Zwang, M. Guillerm, S. Kliks, S. Halstead, R. W. Peeling, and H. S. Margolis. 2014. 'Evaluation of commercially available diagnostic tests for the detection of dengue virus NS1 antigen and anti-dengue virus IgM antibody', *PLoS Negl Trop Dis,* 8: e3171.

Leblois, H., and P. R. Young. 1995. 'Maturation of the dengue-2 virus NS1 protein in insect cells: effects of downstream NS2A sequences on baculovirus-expressed gene constructs', *J Gen Virol,* 76 (Pt 4): 979-84.

Lemos, G., I. Guillen, J. R. Fernandez, T. Diaz, A. B. Colarte, and M. E. F. de Cassio. 2013. 'Expression and purification of a full length recombinant NS1 protein from dengue 2 serotype viral isolate', Biotecnologia Aplicada, 30:187-93.

Lima Mda, R., R. M. Nogueira, A. M. Filippis, P. C. Nunes, C. S. Sousa, M. H. Silva, and F. B. Santos. 2014. 'A simple heat dissociation method increases significantly the ELISA detection sensitivity of the nonstructural-1 glycoprotein in patients infected with DENV type-4*', J Virol Methods,* 204:105-8.

Lima Mda, R., R. M. Nogueira, H. G. Schatzmayr, and F. B. dos Santos. 2010. 'Comparison of three commercially available dengue NS1 antigen capture assays for acute diagnosis of dengue in Brazil', *PLoS Negl Trop Dis,* 4: e738.

Marblestone, J. G., S. C. Edavettal, Y. Lim, P. Lim, X. Zuo, and T. R. Butt. 2006. 'Comparison of SUMO fusion

53 technology with traditional gene fusion systems: enhanced expression and solubility with SUMO', *Protein Sci,* 15:182-9.

Masrinoul, P., M. O. Diata, S. Pambudi, K. Limkittikul, K. Ikuta, and T. Kurosu. 2011. 'Highly conserved region 141168 of the NS1 protein is a new common epitope region of dengue virus', *Jpn J Infect Dis,* 64:109-15.

Osorio, L., M. Ramirez, A. Bonelo, L. A. Villar, and B. Parra. 2010. 'Comparison of the diagnostic accuracy of commercial NS1-based diagnostic tests for early dengue infection', *Virol J,* 7:361.

Pal, S., A. L. Dauner, I. Mitra, B. M. Forshey, P. Garcia, A. C. Morrison, E. S. Halsey, T. J. Kochel, and S. J. Wu. 2014. 'Evaluation of dengue NS1 antigen rapid tests and ELISA kits using clinical samples', *PLoS One,* 9: e113411.

Pal, S., A. L. Dauner, A. Valks, B. M. Forshey, K. C. Long, B. Thaisomboonsuk, G. Sierra, V. Picos, S. Talmage, A. C. Morrison, E. S. Halsey, G. Comach, C. Yasuda, M. Loeffelholz, R. G. Jarman, S. Fernandez, U. S. An, T. J. Kochel, L. E. Jasper, and S. J. Wu. 2015. 'Multi-country prospective clinical evaluation of two ELISAs and two rapid diagnostic tests for diagnosing dengue fever', *J Clin Microbiol.*

Panavas, T., C. Sanders, and T. R. Butt. 2009. 'SUMO fusion technology for enhanced protein production in prokaryotic and eukaryotic expression systems', *Methods Mol Biol,* 497:303-17.

Puttikhunt, C., T. Prommool, U. thainual N, P. Ong-ajchaowlerd, K. Yoosook, C. Tawilert, T. Duangchinda, A. Jairangsri, N. Tangthawornchaikul, P. Malasit, and W. Kasinrerk. 2011. 'The development of a novel serotyping-NS1-ELISA to identify serotypes of dengue virus', *Journal of Clinical Virology,* 50:314-9.

Qian, W., D. Yao, F. Yu, B. Xu, R. Zhou, X. Bao, and Z. Lu. 2000. 'Immobilization of antibodies on ultraflat polystyrene surfaces', *Clin Chem,* 46:1456-63.

Qiu, Li-Wen, Biao Di, Kun Wen, Xin-shuai Wang, Wei-hua Liang, Ya-di Wang, Yu-xian Pan, Ming Wang, Yan-qing Ding, and Xiao-yan Che. 2009. 'Development of an antigen capture immunoassay based on monoclonal antibodies specific for dengue virus serotype 2 nonstructural protein 1 for early and rapid identification of dengue virus serotype 2 infections', Clinical & Vaccine Immunology: CVI, 16:88-95.

Rozen-Gagnon, K., N. J. Moreland, C. Ruedl, and S. G. Vasudevan. 2012. 'Expression and immunoaffinity purification of recombinant dengue virus 2 NS1 protein as a cleavable SUMOstar fusion', *Protein Expr Purif,* 82:20-5.

Sabin, A. B. 1952. Research on Dengue during world war II. *Am. J. Trop. Med. Hyg.* 1:30-50.

Sea, V. R., A. C. Cruz, R. Q. Gurgel, B. T. Nunes, E. V. Silva, S. S. Dolabella, and R. L. dos Santos. 2013. 'Underreporting of Dengue-4 in Brazil due to low sensitivity of the NS1 Ag test in routine control programs', *PLoS One,* 8: e64056.

Shan, X., X. Wang, Q. Yuan, Y. Zheng, H. Zhang, Y. Wu, and J. Yang. 2015. 'Evaluation of the diagnostic accuracy of nonstructural protein 1 Ag-based tests for dengue virus in Asian population: a meta-analysis', *BMC Infect Dis,* 15:360.

Vashist, S. K. 2012. 'Effect of antibody modifications on its biomolecular binding as determined by surface plasmon resonance', *Anal Biochem,* 421:336-8.

Xu, H., B. Di, Y. X. Pan, L. W. Qiu, Y. D. Wang, W. Hao, L. J. He, K. Y. Yuen, and X. Y. Che. 2006. 'Serotype 1-specific monoclonal antibody-based antigen capture immunoassay for detection of circulating nonstructural protein NS1: Implications for early diagnosis and serotyping of dengue virus infections', Journal of Clinical Microbiology, 44:2872-78.

Young, P. R., P. A. Hilditch, C. Bletchly, and W. Halloran. 2000. 'An antigen capture enzyme-linked immunosorbent assay reveals high levels of the dengue virus protein NS1 in the sera of infected patients', *J Clin Microbiol,* 38:1053-7.

Zuo, X., M. R. Mattern, R. Tan, S. Li, J. Hall, D. E. Sterner, J. Shoo, H. Tran, P. Lim, S. G. Sarafianos, L. Kazi, S. Navas-Martin, S. R. Weiss, and T. R. Butt. 2005. 'Expression and purification of SARS coronavirus proteins using SUMO-fusions', *Protein Expr Purif,* 42:100-10.

The invention claimed is:

1. An antibody or antigen-binding fragment thereof that binds specifically to Dengue virus serotype 4 (DENV4), wherein the antibody or antigen-binding fragment comprises:

(A)

a heavy chain variable region that comprises complementarity determining region (CDR) 1 that comprises the amino acid sequence of SYVMH (SEQ ID NO: 4), CDR2 that comprises the amino acid sequence of YLNPYNDDTKYNEKFKG (SEQ ID NO: 5), and CDR3 that comprises the amino acid sequence of GPPYALDY (SEQ ID NO: 6), and a light chain variable region that comprises CDR1 that comprises the amino acid sequence of SVSSSIS-SSNLH (SEQ ID NO: 40), CDR2 that comprises the amino acid sequence of GTSNLAS (SEQ ID NO: 41), and CDR3 that comprises the amino acid sequence of QQWSSYPLT (SEQ ID NO: 42); or (B)

a heavy chain variable region that comprises CDR1 that comprises the sequence of DTYMH (SEQ ID NO: 37), CDR2 that comprises the sequence of YLNPYNDDT-KYNEKFKG (SEQ ID NO: 38), and CDR3 that comprises the sequence of GGIFYYYGSSYSYAMDY (SEQ ID NO: 39); and a light chain variable region that comprises CDR1 that comprises the sequence of RASQDISNYLN (SEQ ID NO: 10), CDR2 that comprises the sequence of YTSRLHS (SEQ ID NO: 11), and CDR3 that comprises the sequence of QQGNTLPRT (SEQ ID NO: 12).

2. The antibody or antigen-binding fragment thereof according to claim 1, wherein the antigen-binding fragment is selected from the group consisting of a Fab fragment, a F(ab)', a F(ab)'2 fragment, or a single-chain variable fragments (scFvs).

3. The antibody or antigen-binding fragment thereof according to claim 1, wherein the antibody or antigen-binding fragment thereof is specific for the DENV4 Non-structural protein 1 (NS1).

4. The antibody or antigen-binding fragment thereof according to claim 1, wherein the heavy chain variable region comprises the amino acid sequence of:

```
                                    (SEQ ID NO: 14)
EVQLQQSGPELVKPGASVKMSCKASGYTFTSYVMHWVKQKPGQGLEWIG

YLNPYNDDTKYNEKFKGKATLTSDKSSSTAYMELSSLTSEDSAVYYCAY

GPPYALDYWGQGTSVTVSS, or (SEQ ID NO: 43)
EVQLQQSGAELVKPGASVKLSCTASGFNIKDTYMHWVKQRPEQGLEWIG

RIDPANGNTQYGPKFQGKATITADTSSNTAYLQLSSLTSEDTAVYYCAR

GGIFYYYGSSYSYAMDYWGQGTSVTVSS.
```

5. The antibody or antigen-binding fragment thereof according to claim 1, wherein the light chain variable region comprises the amino acid sequence of:

```
                                    (SEQ ID NO: 16)
DIQMTQTTSSLSASLGDRVTISCRASQDISNYLNWYQQKPDGTVTLLIY

YTSRLHSGVPSRFSGSGSGTDYSLTISNLEQEDIATYFCQQGNTLPRTF

GGGTKLEIK, or (SEQ ID NO: 44)
QIVLTQSPAIMTASLGERVTMTCTASSSVSSSYLHWYQQKPGSSPKLWI

YSTSNLASGVPARFSGSGSGTSYSLTISSMEAEDAATYYCHQYHRSPYT

FGGGTKLEIK.
```

6. The antibody or antigen-binding fragment thereof according to claim 1, wherein:

the heavy chain variable region comprises the amino acid sequence of EVQLQQSGAELVKPGASVKLSC-TASGFNIKDTYMHWVKQRPEQGLEWIGRIDPA NGNTQYGPKFQGKATITADTSSNTAYLQLSSLT-SEDTAVYYCARGGIFYYYGSSYSYAM DYWGQGTSVTVSS (SEQ ID NO: 43); and the light chain variable region comprises the amino acid sequence of

```
                                    (SEQ ID NO: 16)
DIQMTQTTSSLSASLGDRVTISCRASQDISNYLNWYQQKPDGTVTLLI

YYTSRLHSGVPSRFSGSGSGTDYSLTISNLEQEDIATYFCQQGNTLPR

TFGGGTKLEIK.
```

7. The antibody or antigen-binding fragment thereof according to claim 1, wherein:

the heavy chain variable region comprises the amino acid sequence of EVQLQQSGPELVKPGASVKMSCK-ASGYTFTSYVMHWVKQKPGQGLEWIGYLNP YNDDTKYNEKFKGKATLT-SDKSSSTAYMELSSLTSEDSAVYYCAYGPPY-ALDYWGQGT SVTVSS (SEQ ID NO: 14); and the light chain variable region comprises the amino acid sequence of

```
                                    (SEQ ID NO: 44)
QIVLTQSPAIMTASLGERVTMTCTASSSVSSSYLHWYQQKPGSSPKLW

IYSTSNLASGVPARFSGSGSGTSYSLTISSMEAEDAATYYCHQYHRSP

YTFGGGTKLEIK.
```

8. A pharmaceutical composition comprising the antibody or the fragment thereof of claim 1, and a pharmaceutically acceptable carrier.

9. A method of detecting a DENV4 infection, the method comprising:

contacting a blood sample from a patient with the antibody or antigen-binding fragment thereof according to claim 1; and detecting the binding of NS1.

10. The method according to claim 9, wherein the contacting the blood sample comprises:

contacting the blood sample with an immobilized antibody or antigen-binding fragment thereof according to claim 1; and contacting the antibody retained DENV4 virion with a second antibody or antigen-binding fragment thereof according to claim 1.

11. The method according to claim 10, wherein the immobilized antibody or antigen-binding fragment thereof and the second antibody or fragment thereof are different antibodies; or wherein the secondary antibody or antigen-binding fragment thereof is linked to a detectable label.

12. The method according to claim 11, where the detectable label is selected from the group consisting of an enzyme, biotin, streptavidin, a radioactive molecule, and an immunofluorescent protein or dye.

13. The method according to claim 12, wherein when the detectable label is biotin or streptavidin, the method further comprises contacting a complex comprising a NS1 and the labeled antibody with a detection molecule that comprises streptavidin or biotin, respectively, linked to an immunofluorescent protein or dye or an enzyme; or the method further comprises contacting a complex comprising a NS1 and the labeled antibody with a detection molecule that comprises streptavidin or biotin, respectively, linked to an immunofluorescent protein or dye.

14. The method according to claim 8, wherein the antibody is linked to a detectable label and optionally a bead, particle, or nanoparticle.

15. The method according to claim 14, wherein the bead, particle, or nanoparticle is a magnetic bead.

16. The method according to claim 15, further comprising separating a complex comprising NS1 and the labeled antibody or antigen-binding fragment thereof via the bead, particle or nanoparticle for detecting the binding of NS1.

\* \* \* \* \*